United States Patent
Bruno Quinta De Souza Leal

(10) Patent No.: US 11,946,050 B2
(45) Date of Patent: Apr. 2, 2024

(54) POLYNUCLEOTIDE COMPOSITIONS AND METHODS FOR GENE EXPRESSION REGULATIONS

(71) Applicant: Aptah Bio, Inc., San Carlos, CA (US)

(72) Inventor: Caio Bruno Quinta De Souza Leal, Florianópolis-SC (BR)

(73) Assignee: APTAH BIO, INC., San Carlos, CA (US)

( * ) Notice: Subject to any disclaimer, the term of this patent is extended or adjusted under 35 U.S.C. 154(b) by 0 days.

(21) Appl. No.: 17/867,446

(22) Filed: Jul. 18, 2022

(65) Prior Publication Data
US 2023/0047776 A1 Feb. 16, 2023

Related U.S. Application Data

(60) Provisional application No. 63/222,741, filed on Jul. 16, 2021.

(51) Int. Cl.
| | | |
|---|---|---|
| C07H 21/04 | (2006.01) | |
| C12N 15/11 | (2006.01) | |
| C12N 15/113 | (2010.01) | |
| C12N 15/90 | (2006.01) | |

(52) U.S. Cl.
CPC .......... *C12N 15/113* (2013.01); *C12N 15/111* (2013.01); *C12N 15/90* (2013.01); *C12N 2310/11* (2013.01); *C12N 2310/315* (2013.01); *C12N 2310/321* (2013.01); *C12N 2310/3519* (2013.01); *C12N 2310/531* (2013.01); *C12N 2320/33* (2013.01)

(58) Field of Classification Search
None
See application file for complete search history.

(56) References Cited

U.S. PATENT DOCUMENTS

2020/0231969 A1   7/2020   Vorechovsky et al.

FOREIGN PATENT DOCUMENTS

| WO | WO-2004094593 A2 | 11/2004 |
|---|---|---|
| WO | WO-2005003294 A2 | 1/2005 |
| WO | WO-2015021432 A1 | 2/2015 |
| WO | WO-2015157555 A2 | 10/2015 |
| WO | WO-2015157555 A8 | 3/2016 |
| WO | WO-2017106767 A1 | 6/2017 |
| WO | WO-2019014262 A1 | 1/2019 |
| WO | WO-2019014267 A1 | 1/2019 |
| WO | WO-2023288111 A2 | 1/2023 |

OTHER PUBLICATIONS

Youssef et al. ("Dynamic interactions within sub-complexes of the H/ACA pseudouridylation guide RNP." Nucleic acids research 35.18 (2007): 6196-6206).*

Adachi et al. Insight into the mechanisms and functions of spliceosomal snRNA pseudouridylation. World J. Biol. Chem. 5:398-408 (2014).
Bai et al. Effects of RNA Splicing Inhibitors on Amyloid Precursor Protein Expression. ACS Omega 3(3):2798 (2018).
Bai et al. Integrated Approaches for Analyzing U1-70K Cleavagein Alzheimer's Disease. J Proteome Res. 13(11):4526-4534 (2014).
Bai et al. U1 small nuclear ribonucleoprotein complex and RNA splicing alterations in Alzheimer's disease. PNAS USA 110(41):16562-16567 (2013).
Bishof et al. RNA-binding proteins with basic-acidic dipeptide (BAD) domains self-assemble and aggregate in Alzheimer's disease. J Biol Chem 293(28):11047 (2018).
Boelens et al. The human U1 snRNP-specific U1A protein inhibits polyadenylation of its own pre-mRNA. Cell 72:881-892 (1993).
Chen et al. METTL4 is an snRNA m6Am methyltransferase that regulates RNA splicing. Cell Res. 30:544-547 (2020).
Chow et al. An amazing sequence arrangement at the 5' ends of adenovirus 2 messenger RNA. Cell 12:1-8 (1977).
Chu et al. Role of the central junction in folding topology of the protein-free human U2-U6 snRNA complex. RNA 26:836-850 (2020).
Darzacq et al. Cajal body-specific small nuclear RNAs: a novel class of 2'-O-methylation and pseudouridylation guide RNAs. EMBO J. 21:2746-2756 (2002).
De Gruyter et al. Modifications in small nuclear RNAs and their roles in spliceosome assembly and function. Biol. Chem. 399:1265-1276 (2018).
De Zoysa et al. Posttranscriptional RNA Pseudouridylation. The Enzymes 41:151-167 (2017).
Deryusheva et al. Dual nature of pseudouridylation in U2 snRNA: Pus1p-dependent and Pus1p-independent activities in yeasts and higher eukaryotes. RNA 23:1060-1067 (2017).
Deryusheva et al. "Lost and Found": snoRNA Annotation in the Xenopus Genome and Implications for Evolutionary Studies. Mol. Biol. Evol. 37:149-166 (2020).
Deryusheva et al. Orchestrated positioning of post-transcriptional modifications at the branch point recognition region of U2 snRNA. RNA 24:30-42 (2018).
Deryusheva et al. Post-transcriptional modification of spliceosomal RNAs is normal in SMN-deficient cells. RNA 18:31-36 (2012).
Grainger et al. Binding of U1A protein to the 3' untranslated region of its pre-mRNA. J. Mol. Biol. 288:585-594 (1999).
Gunderson et al. The human U1A snRNP protein regulates polyadenylation via a direct interaction with poly(A) polymerase. Cell 76:531-541 (1994).
Hsieh et al. Tau-Mediated Disruption of the Spliceosome Triggers Cryptic RNA Splicing and Neurodegeneration in Alzheimer's Disease. Cell Reports 29(2):301-316.e10 (2019).

(Continued)

*Primary Examiner* — Kimberly Chong
(74) *Attorney, Agent, or Firm* — WILSON SONSINI GOODRICH & ROSATI

(57) ABSTRACT

This disclosure concerns an engineered polynucleotide that interacts with a pre-mRNA and a spliceosome to regulate gene expression. The engineered polynucleotide may have stem-loop structure that recruits the spliceosome and targeting sequences that are complementary to a target sequence at an exon-intron splice junction and may include nucleotides with 2' modifications and phorphorothioate linkages.

28 Claims, 16 Drawing Sheets

Specification includes a Sequence Listing.

(56) References Cited

OTHER PUBLICATIONS

Jutzi et al., Aberrant interaction of FUS with the U1 snRNA provides a molecular mechanism of FUS induced amyotrophic lateral sclerosis. Nat Commun. 11(1):6341. doi: 10.1038/s41467-020-20191-3 [1-14] (2020).
Kneynsberg et al. Axonal degeneration in tauopathies: Disease relevance and underlying mechanisms. Front Neurosc 11:572 (2017).
Lacadie et al. Cotranscriptional spliceosome assembly dynamics and the role of U1 snRNA:5'ss base pairing in yeast. Mol. Cell 19:65-75 (2005).
Ma et al. Non-snRNP U1A levels decrease during mammalian B-cell differentiation and release the IgM secretory poly(A) site from repression. RNA 12:122-132 (2006).
Meier. RNA modification in Cajal bodies. RNA Biol. 14:693-700 (2017).
Morais et al. Spliceosomal snRNA Epitranscriptomics. Front. Genet. 12:652129 (2021).
Muto et al. The structure and biochemical properties of the human spliceosomal protein U1C. J. Mol. Biol. 341:185-198 (2004).
Nachtergaele et al. The emerging biology of RNA post-transcriptional modifications. RNA Biol. 14:156-163 (2017).
Nelissen et al. The association of the U1-specific 70K and C proteins with U1 snRNPs is mediated in part by common U snRNP proteins. EMBO J. 13:4113-4125 (1994).
Nilsen et al. Expansion of the eukaryotic proteome by alternative splicing. Nature 463:457-463 (2010).
Oh et al. U1 snRNP regulates cancer cell migration and invasion in vitro. Nat Commun. 11(1):1 (2020).
Roundtree et al. Dynamic RNA Modifications in Gene Expression Regulation. Cell 169:1187-1200 (2017).
Singh et al. Gamma-monomethyl phosphate: a cap structure in spliceosomal U6 small nuclear RNA. PNAS USA 86:8280-8283 (1989).
Spraggon et al. U1 snRNP-Dependent Suppression of Polyadenylation: Physiological Role and Therapeutic Opportunities in Cancer. Int J Cell Biol. 2013:846510 (2013).
Séraphin et al. A U1 snRNA: pre-mRNA base pairing interaction is required early in yeast spliceosome assembly but does not uniquely define the 5' cleavage site. EMBO J. 7:2533-2538 (1988).
Tang et al., Characterization of yeast U1 snRNP A protein: identification of the N-terminal RNA binding domain (RBD) binding site and evidence that the C-terminal RBD functions in splicing. RNA 2(10):1058-1070 (1996).
Turunen et al. The significant other: splicing by the minor spliceosome. Wiley Interdiscip. Rev. RNA 4:61-76 (2013).
Wahl et al. The spliceosome: design principles of a dynamic RNP machine. Cell 136:701-718 (2009).
Wang et al. Alternative isoform regulation in human tissue transcriptomes. Nature 456:470-476 (2008).
Wiener et al. The epitranscriptome beyond m6A. Nat. Rev. Genet. 22:119-131 (2021).
Zhu et al. Effects of U1 Small Nuclear Ribonucleoprotein Inhibition on the Expression of Genes Involved in Alzheimer's Disease. ACS Omega 5(39):25306-25311 (2020).
PCT/US2022/037391 Invitation to Pay Additional Fees dated Jan. 9, 2023.
PCT/US2022/037391 International Search Report and Written Opinion dated Mar. 20, 2023.

* cited by examiner

FIG. 6

FIG. 10A
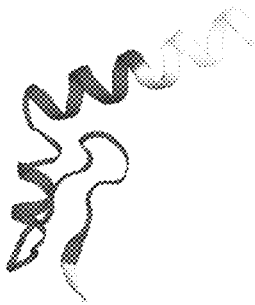
FIG. 10B
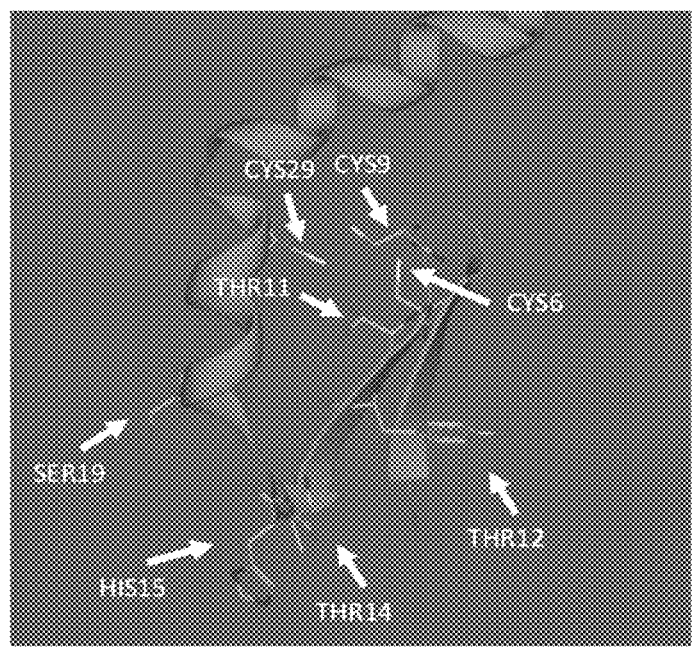
FIG. 10C
```
          10         20         30         40         50
MPKIFCDYCD FNIFHDSFSY RKTHCTGRNH RDNVKYYQK  WMEEQAQHLI
          60         70         80         90        100
DATTAAFKAG KITNNPFAGG PGGAPPKPAG VSIPPPNMGA PPRPGMPGMP
         110        120        130        140
YMPPLMNPMM GMRPPPIMNP MAMMGPPPPL GTIPGVRPGI MNGPK
```
SEQ ID NO: 21

ASMO-2
SEQ ID NO: 24

| Statistics: | |
|---|---|
| % A | 15.00 [3] |
| % A+T | 45.00 [9] |
| % Ambiguous | 0.00 [0] |
| % C | 30.00 [6] |
| % G | 25.00 [5] |
| % G+C | 55.00 [11] |
| % T | 30.00 [6] |
| % dCG | 5.26 [1] |
| Total number of bases | 20 |
| % AA | 0.00 [0] |
| % AC | 5.26 [1] |
| % AG | 5.26 [1] |
| % AT | 5.26 [1] |
| % CA | 10.53 [2] |
| % CC | 5.26 [1] |
| % CG | 5.26 [1] |
| % CT | 10.53 [2] |
| % GA | 0.00 [0] |
| % GC | 10.53 [2] |
| % GG | 5.26 [1] |
| % GT | 5.26 [1] |
| % TA | 5.26 [1] |
| % TC | 10.53 [2] |
| % TG | 5.26 [1] |
| % TT | 10.53 [2] |

Phosphorothioate (Thiol)

2'-O-methyl (2'-O-Me)

POLYNUCLEOTIDE COMPOSITIONS AND METHODS FOR GENE EXPRESSION REGULATIONS

CROSS REFERENCE

This application claims the benefit of U.S. Provisional Application No. 63/222,741, filed on Jul. 16, 2021, which application is incorporated herein by reference in its entirety for all purposes.

SEQUENCE LISTING

The instant application contains a Sequence Listing which has been submitted electronically in XML format and is hereby incorporated by reference in its entirety. Said XML copy, created on Sep. 9, 2022, is named 61572-701_201_SL.xml and is 65,321 bytes in size.

BACKGROUND

Genetic editing with Clustered Regularly Interspaced Short Palindromic Repeats (CRISPR) technology can introduce permanent deoxyribonucleic acid (DNA) mutation(s) and hence presents off-target issues, e.g., in therapeutic applications. Efficiency of gene regulations at ribonucleic acid (RNA) levels remain limited. Accordingly, there is a need for developing polynucleotide compositions and methods for regulating gene expression and activity, e.g., at therapeutically efficacious and safe levels.

SUMMARY

Described herein, in some aspects, is an engineered polynucleotide comprising: one or more targeting moiety configured to specifically bind a pre-messenger ribonucleic acid (pre-mRNA) at a target sequence therein; and a recruiting moiety configured to recruit a post-transcriptional regulating moiety (e.g., a spliceosomal moiety), wherein, when associated with said pre-mRNA and said engineered polynucleotide, said post-transcriptional regulating moiety alters said pre-mRNA in or in proximity to said target sequence. In some embodiments, a targeting moiety of said one or more targeting moiety is sufficiently identical or complementary to a consensus sequence in said target sequence of a target gene. In some embodiments, said one or more targeting moiety comprises a first targeting moiety configured to specifically bind a first targeted sequence in said target sequence of said pre-mRNA, and a second targeting moiety configured to specifically bind a second targeted sequence in said target sequence of said pre-mRNA. In some embodiments, said first targeted sequence comprises a consensus sequence in said target sequence. In some embodiments, said second targeted sequence comprises a consensus sequence in said target sequence. In some embodiments, said first and second targeted sequences are apart in said target sequence by a spacing sequence of no more than five nucleotides (e.g., one or two nucleotides). In some embodiments, said target sequence comprises an exon-intron boundary in said pre-mRNA. In some embodiments, said first and second targeted sequences are both 5' or 3' with respect to said exon-intron boundary. In some embodiments, one of said first and second targeted sequences is 5' with respect to said exon-intron boundary; and wherein the other of said first and second targeted sequences is 3' with respect to said exon-intron boundary. In some embodiments, said target sequence comprises a splice site in said pre-mRNA. In some embodiments, said first or second targeted sequence comprises a splice site (e.g., 5' ss) in said pre-mRNA. In some embodiments, one of said first and second targeting moieties is 5' with respect to said recruiting moiety, and the other of said first and second targeting moieties is 3' with respect to said recruiting moiety In some embodiments, said first targeting moiety or said second targeting moiety comprises a sequence identical or complementary to a sequence set forth in Table 1. In some embodiments, said first targeting moiety comprises a sequence identical or complementary to a sequence selected from the 5'-targeting moiety sequences column of Table 1; and wherein said second targeting moiety comprises a sequence identical or complementary to a sequence set forth in the 3'-targeting moiety sequences column of Table 1. In some embodiments, said first targeting moiety comprises a sequence identical or complementary to a sequence set forth in the 3'-targeting moiety sequences column of Table 1; and wherein said second targeting moiety comprises a sequence identical or complementary to a sequence set forth in the 5'-targeting moiety sequences column of Table 1. In some embodiments, said first targeting moiety or said second targeting moiety comprises a sequence identical or complementary to a consensus sequence of an intron donor site (e.g., selected from GU, GT, GC, and CA). In some embodiments, said first targeting moiety or said second targeting moiety comprises a sequence identical or complementary to a consensus sequence of an exon donor site (e.g., G). In some embodiments, said first targeting moiety or said second targeting moiety comprises a sequence identical or complementary to a consensus sequence selected from GU, GC, G, and CA. In some embodiments, said spliceosomal moiety is selected from a spliceosomal ribonucleoprotein complex, a spliceosomal small nuclear ribonucleic acid (snRNA), a spliceosomal protein, a functional variant thereof, or a functional fragment thereof. In some embodiments, said spliceosomal moiety comprises U1 snRNA and a spliceosomal protein. In some embodiments, said spliceosomal snRNA is selected from U1, U2, U4, U5, U6, U11, U12, U14atac, U6atac, and combinations thereof. In some embodiments, said spliceosomal protein is selected from Sm, U1-70 k, U1A, U1C, and combinations thereof. In some embodiments, said recruiting moiety comprises a nucleotide sequence that is at least 70%, 80%, 85%, or 90% identical or complementary to a sequence set forth in Tables 2-3. In some embodiments, said recruiting moiety comprises a nucleotide sequence that is identical or complementary to a sequence set forth in Tables 2-3. In some embodiments, said engineered polynucleotide comprises a (e.g., secondary) structural feature. In some embodiments, said engineered polynucleotide comprises an apical loop, an upper stem, an internal loop, a lower stem, or a combination thereof. In some embodiments, said engineered polynucleotide comprises a loop (e.g., an internal loop) adjacent to a stem (e.g., a lower stem or an upper stem) comprising two complementary stem sequences. In some embodiments, a stem sequence of said stem (e.g., said lower stem or said upper stem) comprises no more than about five, four, or three nucleotides. In some embodiments, said loop is an internal loop adjacent to said stem (e.g., said lower stem) and a further stem (e.g., an upper stem) comprising two complementary stem sequences. In some embodiments, said internal loop comprises a nucleic acid sequence of no more than 10, 9, or 8 nucleotides. In some embodiments, a stem sequence of said further stem (e.g., said upper stem) comprises no more than about five, four, or three nucleotides. In some embodiments, said engineered polynucleotide further comprises an apical loop. In some embodiments, said apical loop comprises a nucleic acid sequence of no more than 10, 9, 8, 7, 6, or 5 nucleotides. In some embodiments, said engineered polynucleotide does not comprise any intramolecular disulfide bond. In some embodiments, the engineered polynucleotide, when associated with said spliceosomal moiety, said pre-mRNA exhibits substantially no base pairing with an RNA binding domain (RBD) of U1 snRNA. In some embodiments, the engineered polynucleotide, when associated with said spliceosomal moiety, said pre-mRNA exhibits substantially no base-specific interaction with U1-C protein. In some embodiments, said engineered polynucleotide is configured to specifically interact with zinc-finger of U1-C protein. In some embodiments, a 5'-targeting moiety of said engineered polynucleotide is configured to specifically interact with zinc-finger of U1-C protein. In some embodiments, said engineered polynucleotide (is configured to covalently interact (e.g., via disulfide bonding) with zinc-finger of U1-C protein. In some embodiments, said engineered polynucleotide is configured to non-covalently interact (e.g., via hydrogen bonding) with zinc-finger of U1-C protein. In some embodiments, said engineered polynucleotide comprises a nucleotide sequence complementary to a partial sequence of Stem-Loop II (SL2) of U1 snRNA. In some embodiments, a side of a stem-loop structure of said engineered polynucleotide comprises a nucleotide sequence complementary to a partial sequence of Stem-Loop II (SL2) of U1 snRNA. In some embodiments, said partial sequence comprises the sequence corresponding to 5'-GGCCU-3' of SL2 of U1 snRNA. In some embodiments, said partial sequence does not comprise the sequence corresponding to 5'-CACGUUA-3' of SL2 of U1 snRNA. In some embodiments, said engineered polynucleotide exhibits substantially no base pairing with an anchoring sequence of SL2 of U1 snRNA. In some embodiments, an internal loop of said engineered polynucleotide exhibits substantially no base pairing with said anchoring sequence of said SL2 of U1 snRNA. In some embodiments, a lower stem of said engineered polynucleotide exhibits substantially no base pairing with said anchoring sequence of said SL2 of U1 snRNA. In some embodiments, said anchoring sequence comprises the sequence corresponding to 5'-CACGUUA-3'. In some embodiments, said engineered polynucleotide exhibits substantially no base pairing with H helix of U1 snRNA. In some embodiments, said engineered polynucleotide comprises at least one chemical modification. In some embodiments, said engineered polynucleotide comprises at least one 2'-modified (e.g., 2'-methoxy, 2'-methoxymethyl, or 2'-methoxyethyl) nucleotides. In some embodiments, at least about 50%, 60%, 70%, 80%, or 90% nucleotides of said engineered polynucleotide are chemically modified nucleotides. In some embodiments, at least about 50%, 60%, 70%, 80%, or 90% nucleotides of said engineered polynucleotide are 2'-modified (e.g., 2'-methoxy, 2'-methoxymethyl, or 2'-methoxyethyl) nucleotides. In some embodiments, said engineered polynucleotide comprises at least one phosphorothioate internucleotide bond. In some embodiments, at least about 50%, 60%, 70%, 80%, or 90% internucleotide linkages of said engineered polynucleotide are chemically modified. In some embodiments, at least about 50%, 60%, 70%, 80%, or 90% internucleotide linkages are phosphorathioate. In some embodiments, said engineered polynucleotide comprises about 10 to about 40 nucleotides, about 10 to about 35 nucleotides, about 10 to about 30 nucleotides, or about 10 to about 25 nucleotides. In some embodiments, said recruiting moiety comprises about 10 to about 30 nucleotides, or about 10 to about 20 nucleotides. In some embodiments, said one or more targeting moiety each independently comprises about 2 to about 15 nucleotides, about 2 nucleotides to about 10 nucleotides, or about 2 nucleotides to about 8 nucleotides. In some embodiments, one of said first and second targeting moieties comprises about 2 nucleotides, and the other of said first and second targeting moieties comprises about 5 or 6 nucleotides. In some embodiments, when associated with said engineered polynucleotide and said pre-mRNA, said spliceosomal moiety cleaves or splices said pre-mRNA in said target sequence. In some embodiments, said spliceosomal moiety further facilitates modification of a cleaved pre-mRNA.

Described herein, in some aspects, is an engineered polynucleotide comprising a nucleotide sequence that is at least 70%, 80%, 85%, or 90% identical or complementary to a sequence set forth in Tables 2-3, which engineered polynucleotide is characterized by a (e.g., secondary) structural feature. In some embodiments, said nucleotide sequence is identical or complementary to a sequence set forth in Tables 2-3. In some embodiments, said structural feature comprises one or more stem-loop structures. In some embodiments, said structural feature comprises an apical loop, an upper stem, an internal loop, a lower stem, or a combination thereof. In some embodiments, said engineered polynucleotide comprises a loop (e.g., an internal loop) adjacent to a stem (e.g., a lower stem or an upper stem) comprising two complementary stem sequences. In some embodiments, a stem sequence of said stem (e.g., said lower stem or said upper stem) comprises no more than about five, four, or three nucleotides. In some embodiments, said loop is an internal loop adjacent to said stem (e.g., said lower stem) and a further stem (e.g., an upper stem) comprising two complementary stem sequences. In some embodiments, said internal loop comprises a nucleic acid sequence of no more than 10, 9, or 8 nucleotides. In some embodiments, a stem sequence of said further stem (e.g., said upper stem) comprises no more than about five, four, or three nucleotides. In some embodiments, said engineered polynucleotide further comprises an apical loop. In some embodiments, said apical loop comprises a nucleic acid sequence of no more than 10, 9, 8, 7, 6, or 5 nucleotides. In some embodiments, said engineered polynucleotide further comprises one or more targeting moiety sufficiently identical or complementary to a target sequence of a target gene. In some embodiments, a targeting moiety of said one or more targeting moiety is sufficiently identical or complementary to a consensus sequence in said target sequence of said target gene. In some embodiments, said target gene is microtubule associated protein tau (MAPT). In some embodiments, said engineered polynucleotide comprises at least one chemical modification. In some embodiments, said engineered polynucleotide comprises at least one phosphorothioate internucleotide bond. In some embodiments, at least about 50%, 60%, 70%, 80%, or 90% internucleotide linkages of said engineered polynucleotide are chemically modified. In some embodiments, at least about 50%, 60%, 70%, 80%, or 90% internucleotide linkages are phosphorathioate. In some embodiments, said engineered polynucleotide comprises at least one 2'-modified (e.g., 2'-methoxy, 2'-methoxymethyl, or 2'-methoxyethyl) nucleotides. In some embodiments, at least about 50%, 60%, 70%, 80%, or 90% nucleotides of said engineered polynucleotide are chemically modified nucleotides. In some embodiments, at least about 50%, 60%, 70%, 80%, or 90% nucleotides of said engineered polynucleotide are 2'-modified (e.g., 2'-methoxy, 2'-methoxymethyl, or 2'-methoxyethyl) nucleotides. In some embodiments, said engineered polynucleotide comprises about 10 to about 40 nucleotides, about 10 to about 35 nucleotides, about 10 to about 30 nucleotides, or about 10 to about 25 nucleotides.

Described herein, in some aspects, is a method for altering a pre-messenger ribonucleic acid (pre-mRNA) in a cell, the method comprising contacting said cell with an engineered polynucleotide that comprises one or more targeting moiety and a recruiting moiety, wherein said one or more targeting moiety binds to said pre-mRNA at a target sequence therein, and said recruiting moiety recruits a post-transcriptional regulating moiety (e.g., a spliceosomal moiety) within proximity of said target sequence of said pre-mRNA to alter said pre-mRNA in said cell, thereby yielding one or more altered pre-mRNA. In some embodiments, a targeting moiety of said one or more targeting moiety is sufficiently identical or complementary to a consensus sequence in said target sequence of a target gene. In some embodiments, said pre-mRNA corresponds to a target gene. In some embodiments, said target gene is microtubule associated protein tau (MAPT). In some embodiments, the method alters an expression or activity of said target gene. In some embodiments, prior to said contacting, said cell exhibits an aberrant messenger ribonucleic acid (mRNA) or protein corresponding to said target gene.

Described herein, in some aspects, is a set of engineered polynucleotides each independently comprise: one or more targeting moiety configured to bind a pre-messenger ribonucleic acid (pre-mRNA) at a target sequence; and a recruiting moiety configured to recruit a post-transcriptional regulating moiety (e.g., a spliceosomal moiety), wherein said set of engineered polynucleotides are configured to specifically bind said pre-mRNA at a plurality of target sequences comprising said target sequence.

Another embodiment described herein is an engineered polynucleotide comprising a first targeting moiety configured to specifically bind a pre-messenger ribonucleic acid (pre-mRNA) at a first targeted sequence therein, a recruiting moiety configured to recruit a spliceosomal moiety, and a second targeting moiety configured to specifically bind the pre-mRNA at a second targeted sequence therein; wherein said recruiting moiety comprises an apical loop, an upper stem adjacent to said apical loop, a lower stem, and an internal loop situated between said upper stem and said lower stem, and wherein said spliceosomal moiety alters said pre-mRNA in a target sequence comprising said first targeted sequence and said second targeted sequence when associated with said pre-mRNA and said engineered polynucleotide. In some aspects, the first targeted sequence and second targeted sequences are separated in said target sequence by a spacing sequence of no more than five nucleotides. In some aspects, the target sequence comprises an exon-intron boundary in said pre-mRNA. In some aspects, the first targeted sequences is 5' of said exon-intron boundary and said second targeted sequence is 3' of said exon-intron boundary. In some aspects, the first targeting moiety comprises a sequence identical to or complementary to a sequence set forth in the exon sequence column of Table 1; and said second targeting moiety comprises a sequence identical to or complementary to a sequence set forth in the intron sequence column of Table 1. In some aspects, the spliceosomal moiety comprises a U1 snRNA and a U1-C protein. In some aspects, the upper stem or said lower stem comprises two complementary sequences and each of the two complementary sequences comprises no more than 5 nucleotides; the internal loop comprises two nucleic acid sequences and each of said two nucleic acid sequence comprises no more than 5 nucleotides; and the apical loop comprises a nucleic acid sequence of no more than 8 nucleotides. In other aspects the pre-mRNA exhibits substantially no base pairing with an RNA binding domain (RBD) of U1 snRNA when associated with said engineered polynucleotide and the spliceosomal moiety exhibits substantially no base-specific interaction with a U1-C protein when associated with said engineered polynucleotide and said spliceosomal moiety. In another aspect, a 5'-targeting moiety of said engineered polynucleotide is configured to specifically interact with a zinc-finger of U1-C protein. In another aspect, the recruiting moiety comprises a nucleotide sequence complementary to at least 4 nucleotides of a sequence of Stem-Loop II (SL2) of U1 snRNA. In another aspect, sequence of SL2 of U1 snRNA comprises 5'-GGCCU-3'. The engineered polynucleotide nay have a 2'-modified nucleotide. At least 50% of the nucleotides of said engineered polynucleotide may be 2'-modified nucleotides. The 2'-modified nucleotides may be 2'-methoxy nucleotides. In another aspect, the engineered polynucleotide comprises nucleotides connected by internucleotide linkages and at least one of said internucleotide linkages does not comprise a phosphate. At least one or 50%, 60%, 70% 80% or 90% of the internucleotide linkages may be a phosphorothioate.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The patent or application file contains at least one drawing executed in color. Copies of this patent or patent application with color drawing(s) will be provided by the Office upon request and payment of the necessary fee.

FIGS. 2A-3B illustrate an example engineered polynucleotide described herein comprising: (1) a 3'-targeting moiety: 3'-GC-5'; (2) a lower stem: 3'-GA-5'/5'-CT3'; (3) an internal loop: 3'-CC-5'/5'-AA-3'; (4) an upper stem: 3'-GGA-5'/5'-CCT-3'; (5) an apical loop: 3'-CTT-5'; and (6) a 5'-targeting moiety: 5'-GTCCA-3'.

FIGS. 3A-3B illustrate the anchoring taking place through the engineered polynucleotide "Stem 5'/3'" (a.k.a., 5'-targeting moiety or/and 3'-targeting moiety), which is designed to interact with conserved moieties present in the constitutive donor site. FIG. 3A. Stem 5'/3' (GTCCA and CG) such as phosphorothioate internucleotide bonds and substitutions of 2' O-methyl (2' O-ME) for molecular sugar increases resistance to endonucleases and increases molecular strength of interaction between the bases of the Stem 5'/3' with conserved regions from constitutive donor. FIG. 3B. Interaction of an engineered polynucleotide described herein with constitutive donor splicing and silencing of the RNA binding moiety (RBD) of U1 snRNA with constitutive donor splicing-exon. Figure discloses SEQ ID NOS 12-13, respectively, in order of appearance.

FIG. 5 illustrates U1 snRNP binding to the 5' exon-intron junction of pre-mRNA and thus playing a crucial role at an early stage of pre-mRNA splicing. Two crystal structures of engineered U1 sub-structures are shown, which together reveal at atomic resolution an almost complete network of protein-protein and RNA-protein interactions within U1 snRNP and show how the 5' splice site of pre-mRNA is recognized by U1 snRNP. The zinc-finger of U1-C interacts with the duplex between pre-mRNA and the 5'-end of U1 snRNA. The binding of the RNA duplex is stabilized by hydrogen bonds and electrostatic interactions between U1-C and the RNA backbone around the splice junction, but U1-C makes no base-specific contacts with pre-mRNA. The structure, together with RNA binding assays, shows that the selection of 5'-splice site nucleotides by U1 snRNP is achieved predominantly through base pairing with U1 snRNA whilst U1-C fine-tunes relative affinities of mismatched 5'-splice sites.

FIG. 6 illustrates U1-70 k in complex with U1 snRNA stem-loops and U1-A RRM in complex with stem-loop 2, stabilized through the U1-C zinc finger. Figure discloses SEQ ID NOS 16-17, respectively, in order of appearance.

FIG. 10A illustrates Fingerprint Z1 U1-C snRNP, represented by 36 amino acid residues in blue color. FIG. 10B illustrates Z1 finger moiety of U1-C snRNP, presenting the main residues that interact with the pre-mRNA/ASMO1 duplex in the 5' constitutive donor region. FIG. 10C illustrates representative sequence of U1-C snRNP containing 145-aa, with the 36-aa highlighted in green refer to the Zinc Finger moiety. Figure discloses SEQ ID NO: 21.

Figure 1:
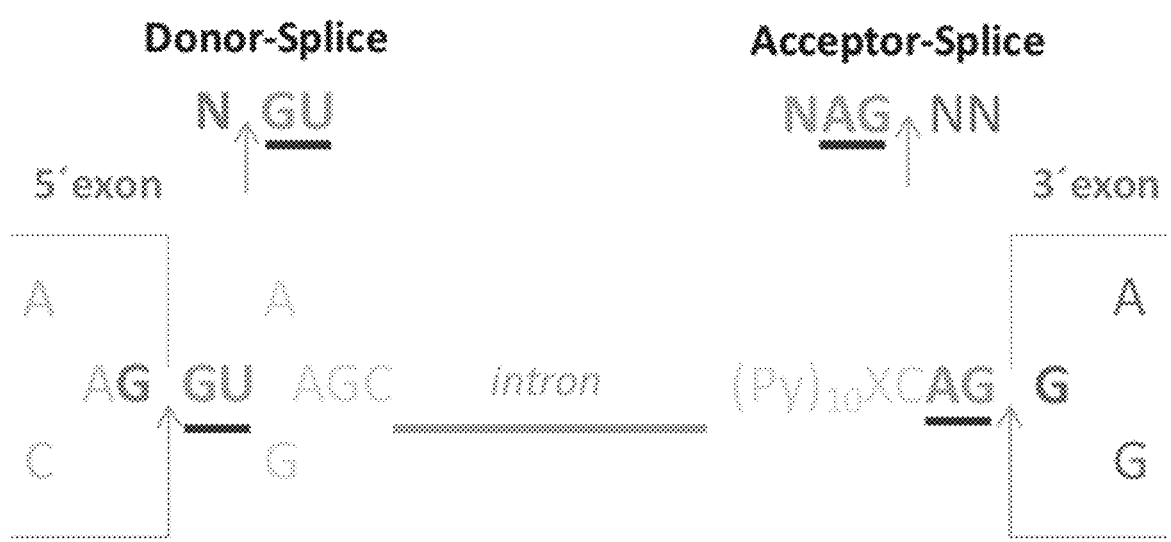
FIG. 1 illustrates a schematic diagram for identification of splice-donor and splice-acceptor sites. An example consensus sequence for messenger ribonucleic acid (mRNA) splicing in animals and plants is "GU_AG," where "GU" is an example splice donor sequence and "AG" is an example splice acceptor sequence. A longer splice donor consensus sequence in mammals may be "GUrAGU," where "r" represents either "G" or "A." Usually, an expression of "GU_AG" means that only the 5' and 3' terminal two nucleotides of the sequence are invariable as "GU" and "AG," respectively, and that a sequence represented by the underscore can be any sequences. However, described herein this expression indicates that the sequence represented by the underscore can be any sequences except for sequences that do not match any of the other consensus sequences. The splice acceptor consensus sequence is preceded by a branch point sequence, which contains an adenine, which is ligated to the 5' splice site ribonucleotide to form the intron lariat, and a polypyrimidine tract (C or U), which is between the branch point and the splice acceptor sequence. While the short GU_AG consensus sequence of introns is clearly not sufficient to differentiate amongst the multitude of alternative splicing events, surprisingly little is known about what other sequence information is required to regulate alternative RNA splicing. The flanking one or two nucleotides on either side of the intron are also often conserved, and they are included in our supplementary tables, but they will not be discussed further in this paper so that we can focus our analyses on consensus sequences at the ends of the introns. In this sense, the rational design of an engineered polynucleotide logically identifies the splice's intronic consensus sequences (GU_AG). Then, making it possible to determine conserved regions of the donor site (5' exon and intron downstream) and acceptor (3' exon and intron downstream). It is important to note that the conserved and consensus regions are located within the same site of constitutive splice donor or acceptor. The recognition of the consensus regions determines a 5' splicing site, that is, the limit of junction between the exon and intron. Meanwhile, the recognition of the conserved regions identifies the identity of the transcript chosen for modulation. Figure discloses SEQ ID NO: 26.

The novel features of the disclosure are set forth with particularity in the appended claims. A better understanding of the features and advantages of the present disclosure will be obtained by reference to the following detailed description that sets forth illustrative embodiments.

DETAILED DESCRIPTION

Described herein are (e.g., engineered) polynucleotides, and (e.g., pharmaceutical) compositions and methods for utilizing the same, e.g., for modulating gene expression or activity.
Engineered Polynucleotide(s)

In some embodiments described herein, the engineered polynucleotide comprises: (i) one or more targeting moiety configured to (e.g., specifically) bind a ribonucleic acid (RNA) (e.g., a messenger ribonucleic acid (mRNA), such as a pre-messenger ribonucleic acid (pre-mRNA)) at a target sequence therein. The engineered polynucleotide may further comprise (ii) a recruiting moiety configured to recruit a post-transcriptional regulating moiety (e.g., a spliceosomal moiety) such that, when associated with the RNA (e.g., the mRNA, such as the pre-mRNA) and the engineered polynucleotide, the post-transcriptional regulating moiety alters the RNA (e.g., the mRNA, such as the pre-mRNA) in or in proximity to the target sequence. In some embodiments, the RNA (e.g., the mRNA, such as the pre-mRNA) encodes a target gene.

An engineered polynucleotide or an engineered polynucleotide as described herein can include various moieties. A "moiety" can refer to a region of an engineered polynucleotide. In some cases, a moiety can be described in terms of a function of the moiety. For instance, a "targeting moiety" can refer to a region of the engineered polynucleotide that can be at least partially complementary to a target RNA; a "recruiting moiety" can refer to a moiety that can recruit any one of the regulating moiety described herein; and a "spacing sequence" can refer to a moiety that provides space between other moieties. In some instances, recitation of a moiety name does not limit the moiety to a particular function. For example, a "targeting moiety" that can be at least partially complementary to a target RNA can in some instances recruit a regulating moiety.

Targeting Moieties

In some embodiments of the engineered polynucleotide described herein, a targeting moiety of the one or more targeting moiety is sufficiently identical or complementary to a consensus sequence in the target sequence of a target gene. Targeting moieties can be found at the 5' end and 3' end of an engineered polynucleotide and are also known as lower stems or legs. Without wishing to be bound by theory, stable binding of one or two targeting moieties to a constitutive donor 5' of a target pre-mRNA allows the interaction with the conserved site of the constitutive donor and silences the U1 snRNA RNA-binding domain.

A consensus sequence can be determined based on identification of genetic variants of unknown significance (VUS). Any exonic or intronic VUS can be spliceogenic by disrupting the cis DNA sequences that define exons, introns, and regulatory sequences necessary for a correct RNA splicing process. The cis DNA elements can include: exon-intron boundary core consensus nucleotides (e.g., GT at +1 and +2 of the 5'donor site and AG at −1 and −2 of the 3'acceptor site); or intronic and exonic nucleotides adjacent to these invariable nucleotides that are also highly conserved and have been found to be involved for splice site selection (e.g., CAG/GUAAGU in donor sites and NYAG/G in acceptor sites). A nucleotide change in any of these elements can lead to incorrect splice site recognition, creating a new splice site or activating a cryptic splice site, resulting in aberrant transcripts or non-functional proteins associated with a disease or condition. In some embodiments, at least one targeting moiety of the one or more targeting moiety is sufficiently identical or complementary to a consensus sequence in the target sequence of a target gene. In some embodiments, the consensus sequence comprises about 2 to about 15 nucleotides, about 2 nucleotides to about 10 nucleotides, or about 2 nucleotides to about 8 nucleotides. In some embodiments, at least two targeting moieties of the one or more targeting moiety are sufficiently identical or complementary to at least two consensus sequences in the target sequence of a target gene. In some embodiments, the one or more targeting moiety are each independently sufficiently identical or complementary to a consensus sequence in the target sequence of a target gene.

In some embodiments of the engineered polynucleotide described herein, the one or more targeting moiety each independently comprises about 2 to about 15 nucleotides, about 2 nucleotides to about 10 nucleotides, or about 2 nucleotides to about 8 nucleotides. In some embodiments of the engineered polynucleotide described herein, the one or more targeting moiety each independently comprises 2, 3, 4, 5, 6, 7, 8, 9, or 10 nucleotides In some embodiments of the engineered polynucleotide described herein, the one or more targeting moiety comprises (1) a first targeting moiety configured to specifically bind a first targeted sequence in the target sequence of the RNA (e.g., the mRNA, such as the pre-mRNA), and (2) a second targeting moiety configured to specifically bind a second targeted sequence in the target sequence of the RNA (e.g., the mRNA, such as the pre-mRNA). In some embodiments, the first targeted sequence comprises a consensus sequence in the target sequence. In some embodiments, the consensus sequence of the first targeted sequence comprises about 2 to about 15 nucleotides, about 2 nucleotides to about 10 nucleotides, or about 2 nucleotides to about 8 nucleotides. In some embodiments, the consensus sequence of the first targeted sequence comprises 2-3, 3-4, 4-5, 5-6, 6-7, 7-8, or 8-10 nucleotides. In some embodiments, the second targeted sequence comprises a consensus sequence in the target sequence. In some embodiments, the consensus sequence of the second targeted sequence comprises about 2 to about 15 nucleotides, about 2 nucleotides to about 10 nucleotides, or about 2 nucleotides to about 8 nucleotides. In some embodiments, the consensus sequence of the second targeted sequence comprises 2-3, 3-4, 4-5, 5-6, 6-7, 7-8, or 8-10 nucleotides. In some embodiments, the consensus sequence of the first targeted sequence and the consensus sequence of the second targeted sequence are of different nucleotide lengths. In some embodiments, one of the consensus sequences of the first and second targeted sequences comprises about 1 to about 5 nucleotides, and the other of the consensus sequences of the first and second targeted sequences comprises about 4 to about 8 nucleotides. In some embodiments, one of the consensus sequences of the first and second targeted sequences comprises at least about 2 nucleotides, and the other of the consensus sequences of the first and second targeted sequences comprises at least about 5 or 6 nucleotides. In some embodiments, one of the consensus sequences of the first and second targeted sequences comprises about 2 nucleotides, and the other of the consensus sequences of the first and second targeted sequences comprises about 5 or 6 nucleotides.

In some embodiments of the engineered polynucleotide described herein, a first targeting moiety and a second targeting moiety are of different nucleotide lengths. In some embodiments, one of a first targeting moiety and a second targeting moiety comprises about 1 to about 5 nucleotides, and the other of a first targeting moiety and a second targeting moiety comprises about 4 to about 8 nucleotides. In some embodiments, one of a first targeting moiety and a second targeting moiety comprises at least about 2 nucleotides, and the other of a first targeting moiety and a second targeting moiety comprises at least about 5 or 6 nucleotides. In some embodiments, one of a first targeting moiety and a second targeting moiety comprises about 2 nucleotides, and the other of a first targeting moiety and a second targeting moiety comprises about 5 or 6 nucleotides.

In some embodiments, a (e.g., first or second) targeting moiety comprises a nucleic acid sequence having at least one, two, three, four, five, six, seven, eight, nine, ten, or more nucleotides. In some embodiments, a (e.g., first or second) targeting moiety comprises a nucleic acid sequence having at most ten, nine, eight, seven, six, five, four, three, or two nucleotides. In some embodiments, a (e.g., first or second) targeting moiety comprises a nucleic acid sequence having one, two, three, four, five, six, seven, eight, nine, or ten nucleotides, or a range between any two foregoing values.

In some embodiments, the (e.g., first or second) targeting moiety comprises a nucleic acid sequence targeting the nucleotides in an exon. In some embodiments, the (e.g., first or second) targeting moiety comprises a nucleic acid sequence targeting the nucleotides in an exon that are immediately adjacent to an intron. In some embodiments, the (e.g., first or second) targeting moiety comprises a nucleic acid sequence targeting the nucleotides in an exon that are adjacent to or immediately adjacent to an intron that is at the 3' end of the exon. In some embodiments, the (e.g., first or second) targeting moiety comprises a nucleic acid sequence targeting the nucleotides in an exon that are adjacent to or immediately adjacent to an intron that is at the 5' end of the exon. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the exon. In some embodiments, the (e.g., first or second) targeting moiety comprises a nucleic acid sequence targeting the nucleotides in an exon that is immediately adjacent to an intron that is at the 5' end of the exon. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the exon that is adjacent to the an intron. In some embodiments, the (e.g., first or second) targeting moiety comprises a nucleic acid sequence targeting the nucleotides in an exon that is immediate adjacent to an intron that is at the 5' end of the exon. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the exon that is at the 5' of an intron. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the exon that is at the 3' of an intron. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the exon that is not immediately adjacent to an intron.

In some embodiments, the (e.g., first or second) targeting moiety comprises a nucleic acid sequence targeting the nucleotides in intron. In some embodiments, the (e.g., first or second) targeting moiety comprises a nucleic acid sequence targeting the nucleotides in an intron that are adjacent to or immediately adjacent to the exon. In some embodiments, the (e.g., first or second) targeting moiety comprises a nucleic acid sequence targeting the nucleotides in an intron that are adjacent to or immediately adjacent to the exon that is at the 5' end of the intron. In some embodiments, the (e.g., first or second) targeting moiety comprises a nucleic acid sequence targeting the nucleotides in an intron that are adjacent to or immediately adjacent to the exon that is at the 5' end of the intron. In some embodiments, the (e.g., first or second) targeting moiety comprises a nucleic acid sequence targeting the nucleotides that are located entirely within an intron. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in an intron that is adjacent to the exon. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the intron and immediately adjacent to the exon that is at the 5' end of the intron. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the intron and immediately adjacent to the exon that is at the 3' end of the intron. In some embodiments, the (e.g., first or second) targeting moiety comprises a nucleic acid sequence comprising 5'-AA-3', 5'-AT-3', 5'-AC-3', 5'-AG-3', 5'-TA-3', 5'-TT-3', 5'-TC-3', 5'-TG-3', 5'-CA-3', 5'-CT-3', 5'-CC-3', 5'-CG-3', 5'-GA-3', 5'-GT-3', 5'-GC-3', or 5'-GG-3' targeting the nucleotides that are in the intron that is not adjacent to an exon.

In some embodiments of the engineered polynucleotide described herein, a (e.g., first or second) targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence set forth in Table 1. In some embodiments of the engineered polynucleotide described herein, a (e.g., first or second) targeting moiety comprises a sequence identical or complementary to a sequence set forth in Table 1. In some embodiments, a (e.g., first or second) targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence selected from the 5'-targeting moiety sequences column of Table 1 and the 3'-targeting moiety sequences column of Table 1. In some embodiments, a (e.g., first or second) targeting moiety comprises a sequence identical or complementary to a sequence selected from the 5'-targeting moiety sequences column of Table 1 and the 3'-targeting moiety sequences column of Table 1.

In some embodiments, a first targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence selected from the 5'-targeting moiety sequences column of Table 1; and a second targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence set forth in the 3'-targeting moiety sequences column of Table 1. In some embodiments, a first targeting moiety comprises a sequence identical or complementary to a sequence set forth in the 3'-targeting moiety sequences column of Table 1. In some embodiments, a first targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence set forth in the 3'-targeting moiety sequences column of Table 1; and a second targeting moiety comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to a sequence set forth in the 5'-targeting moiety sequences column of Table 1. In some embodiments, a first targeting moiety comprises a sequence identical or complementary to a sequence set forth in the 3'-targeting moiety sequences column of Table 1; and a second targeting moiety comprises a sequence identical or complementary to a sequence set forth in the 5'-targeting moiety sequences column of Table 1. In some embodiments, a (e.g., first or second) targeting moiety comprises a sequence identical or complementary to a consensus sequence of an intron donor site (e.g., selected from GU, GT, GC, and CA). In some embodiments, a (e.g., first or second) targeting moiety comprises a sequence identical or complementary to a consensus sequence of an exon donor site (e.g., G). In some embodiments, a (e.g., first or second) targeting moiety comprises a sequence identical or complementary to a consensus sequence selected from GU, GC, G, and CA.

TABLE 1

Examples of MAPT gene Exon-Intron junction sequences targeted by the 5' and 3'-targeting moieties of engineered polynucleotides and the distance between the two target sequences

| Exon | Exon sequence | Spacer | Intron sequence |
| --- | --- | --- | --- |
| Exon 1 | 5'-CAGGT-3' | 2 nt | 3'-CG-5' |
| Exon 2 | 5'-AAGGT-3' | 2 nt | 3'-TG-5' |
| Exon 3 | 5'-AAGGT-3' | 2 nt | 3'-CG-5' |
| Exon 4 | 5'-CAGGT-3' | 2 nt | 3'-GG-5' |
| Exon 5 | 5'-AAGGT-3' | 2 nt | 3'-TG-5' |
| Exon 6a | 5'-AAGGT-3' | 2 nt | 3'-TG-5' |
| Exon 6b | 5'-AAGGT-3' | 2 nt | 3'-TG-5' |
| Exon 7 | 5'-AAGGT-3' | 2 nt | 3'-CG-5' |
| Exon 8 | 5'-AAGGT-3' | 2 nt | 3'-GG-5' |
| Exon 9 | 5'-CTGGT-3' | 1 nt | 3'-AG-5' |
| Exon 10 | 5'-CTGGT-3' | 2 nt | 3'-AG-5' |
| Exon 11 | 5'-AGTGT-3' | 2 nt | 3'-TG-5' |
| Exon 12 | 5'-CAGGT-3' | 1 nt | 3'-CG-5' |
| Exon 13 | 5'-AAGGT-3' | 3 nt | 3'-GG-5' |
| Exon 14 | 5'-AAGGT-3' | 2 nt | 3'-CC-5 |
| Exon 1 | 5'-AAAAG-3' | 3 nt | 3'-CGA-5' |
| Exon 2 | 5'-AAAAG-3' | 3 nt | 3'-TGA-'5 |
| Exon 3 | 5'-GGAAG-3' | 3 nt | 3'-GGG-'5 |

TABLE 1-continued

Examples of MAPT gene Exon-Intron junction sequences targeted by the 5' and 3'-targeting moieties of engineered polynucleotides and the distance between the two target sequences

| Exon | Exon sequence | Spacer | Intron sequence |
|---|---|---|---|
| Exon 4 | 5'-CACAG-3' | 3 nt | 3'-GGA-5' |
| Exon 5 | 5'-CCAAG-3' | 3 nt | 3'-TGA-5' |
| Exon 6a | 5'-CAAAG-3' | 3 nt | 3'-TGT-5' |
| Exon 6b | 5'-CAAAG-3' | 3 nt | 3'-TGT-5' |
| Exon 7 | 5'-CCAAG-3' | 3 nt | 3'-CGT-5' |
| Exon 8 | 5'-TCAAG-3' | 3 nt | 3'-GGA-5' |
| Exon 9 | 5'-CTCTG-3' | 3 nt | 3'-AGA-5' |
| Exon 10 | 5'-GGAAG-3' | 3 nt | 3'-AGA-5' |
| Exon 11 | 5'-GGCAG-3' | 3 nt | 3'-AGA-5' |
| Exon 12 | 5'-AACAG-3' | 2 nt | 3'-CGA-5' |
| Exon 13 | 5'-AAAAG-3' | 3 nt | 3'-GAA-5' |
| Exon 14 | 5'-TTAAA-3' | 2 nt | 3'-GGA-5' |

Example consensus sequences include: (e.g., 5'-) intron donor site #1: GU; (e.g., 5'-) intron donor site #2: GC; (e.g., 5'-) exon donor site #1: G; and (e.g., 5'-) intron donor site #3: CA.

Target Sequence

In some embodiments of the engineered polynucleotide described herein, a first targeted sequence and a second targeted sequence are apart in the target sequence by a spacing sequence of no more than five, four, or three nucleotides (e.g., one or two nucleotides).

In some embodiments of the engineered polynucleotide described herein, a first targeted sequence and a second targeted sequence are contiguous or adjacent to each other.

In some embodiments, when a spacing sequence in the target sequence is adjacent to a 5'- or 3'-end of a targeted sequence of the target sequence, the spacing sequence may not be complementary to a targeting moiety of the engineered polynucleotide. In some embodiments, when a spacing sequence in the target sequence is adjacent to a 5'- or 3'-end of a targeted sequence of the target sequence, the spacing sequence may not be complementary to any targeting moiety of the engineered polynucleotide.

In some embodiments, the spacing sequence separate a first targeted sequence and a second targeted sequence described herein. In some embodiments, the spacing sequence is not complementary and does not bind to a targeting moiety of the engineered polynucleotide. In some embodiments, the spacing sequence is not complementary and does not bind to all targeting moieties of the engineered polynucleotide.

In some embodiments of the engineered polynucleotide described herein, the target sequence may comprise an exon-intron boundary in the RNA (e.g., the mRNA, such as the pre-mRNA). In some embodiments, a first targeted sequence and a second targeted sequence are both 5' or 3' with respect to the exon-intron boundary. In some embodiments, one of a first targeted sequence and a second targeted sequence is 5' with respect to the exon-intron boundary, and the other of a first targeted sequence and a second targeted sequence is 3' with respect to the exon-intron boundary.

In some embodiments of the engineered polynucleotide described herein, the target sequence comprises a splice site in the RNA (e.g., the mRNA, such as the pre-mRNA). In some embodiments, a (e.g., first or second) targeted sequence comprises a splice site (e.g., 5' ss) in the RNA (e.g., the mRNA, such as the pre-mRNA).

In some embodiments, two targeted sequences (e.g., a first targeted sequences and a second targeted sequence) are part of a single nucleic acid molecule (i.e., the RNA, e.g., the mRNA, such as the pre-mRNA). In some embodiments, the first and second targeted sequences are spanned apart on the single nucleic acid molecule. In some embodiments, the first and second targeted sequences span an exon-intron boundary of the single nucleic acid molecule. In some embodiments, the first and second targeted sequences do not span an exon-intron boundary of the single nucleic acid molecule. In some embodiments, the first and second targeted sequences are adjacent to an exon-intron boundary of the single nucleic acid molecule. In some embodiments, the first and second targeted sequences both target an intron of the single nucleic acid molecule. In some embodiments, the first and second targeted sequences span a splice site in the single nucleic acid molecule. In some embodiments, the first and second targeted nucleic acid sequences do not span a splice site in the single nucleic acid molecule.

In some embodiments of the engineered polynucleotide described herein, a consensus sequence in the target sequence comprises about 2 to about 15 nucleotides, about 2 nucleotides to about 10 nucleotides, or about 2 nucleotides to about 8 nucleotides.

In some embodiments, the engineered polynucleated in complementary and binds to a target sequence. In some embodiments, at least a portion of the engineered polynucleotide binds to a target sequence. In some embodiments, the target sequence encodes a target gene. Non-limiting example of the target gene can include microtubule associated protein tau (MAPT).

In some embodiments, the target sequence comprises an RNA sequence. In some embodiments, the RNA is a nuclear RNA, a cytoplasmic RNA, or a mitochondrial RNA. In some embodiments, the target RNA sequence comprises a messenger RNA (mRNA), a pre-messenger RNA (pre-mRNA), a transfer RNA (tRNA), a ribosomal RNA (rRNA), a ribozyme, a recombinant polynucleotide, a branched polynucleotide, an isolated RNA, an guide RNA, an oligonucleotide, a nucleic acid probe, a primer, an snRNA, a long non-coding RNA, a small RNA, a snoRNA, a siRNA, a miRNA, a tRNA-derived small RNA (tsRNA), an antisense RNA, an shRNA, or a small rDNA-derived RNA (srRNA). In some embodiments, the target RNA sequence is a pre-mRNA. In some embodiments, the engineered polynucleotide is not an antisense oligonucleotide.

In some embodiments, the target RNA sequence comprises at least one exon. In some embodiments, the target RNA sequence comprises at least one intron. In some embodiments, the target RNA sequence comprises at least one exon or at least one intron. In some embodiments, the target RNA sequence comprises at least one exon-intron boundary.

In some embodiments, the target sequence is an endogenous nucleic acid molecule. In some embodiments, the binding of the engineered polynucleotide to the target sequence by base pairing such as Watson-Crick base pairing.

Recruiting Moiety

A recruiting moiety comprises a hairpin structure. The hairpin may be a full hairpin or may be intercalated by internal loops. The hairpin structure may consist of 13 to 17 nucleotides. The recruiting moiety may interact with stem-loop II of the U1 snRNA. U1-A also can bind to stem-loop II of the U1 snRNA. Hydrogen bridges of stem-loop II with the hairpin/internal loop region can indirectly modulate polyadenylation and acetylation signaling by U1-A. The recruiting moiety may not silence the anchoring domain of U1-A in stem-loop II. This interaction can modulate gene expression and acetylation.

In some embodiments of the engineered polynucleotide described herein, the recruiting moiety comprises a nucleotide sequence that is at least 70%, 80%, 85%, or 90% identical or complementary to a sequence set forth in Table 2. In some embodiments, the recruiting moiety comprises a nucleotide sequence that is identical or complementary to a sequence set forth in Table 2. In some embodiments, the engineered polynucleotide comprises a nucleotide sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical or complementary to any sequence selected from SEQ ID NOs: 1-4. In some embodiments, the engineered polynucleotide comprises a nucleotide sequence that is at least 70%, 80%, 85%, or 90% identical or complementary to any sequence selected from SEQ ID NOs: 1-4. In some embodiments, the engineered polynucleotide comprises a nucleotide sequence that is identical or complementary to any sequence selected from SEQ ID NOs: 1-4.

TABLE 2

Example recruiting moieties of engineered polynucleotides described herein

| SEQ ID No. | Sequence | Nucleotide length | | |
|---|---|---|---|---|
| 1 | ctaacctttcaggccag | 17 nt | ASMO1 | (DNA) |
| 2 | cuaaccuuucaggccag | 17 nt | ASMO1 | (RNA) |
| 3 | atcgtcagcttac | 13 nt | ASMO2 | (DNA) |
| 4 | aucgucagcuuac | 13 nt | ASMO2 | (RNA) |

In some embodiments described herein, the engineered polynucleotide (e.g., the recruiting moiety) comprises a (e.g., secondary) structural feature (see FIGS. 2A-2D). In some embodiments, the engineered polynucleotide (e.g., the recruiting moiety) comprises an apical loop, an upper stem, an internal loop, a lower stem, or a combination thereof. In some embodiments, the engineered polynucleotide (e.g., the recruiting moiety) comprises a loop (e.g., an internal loop) adjacent to a stem (e.g., a lower stem or an upper stem) comprising two complementary stem sequences. In some embodiments, a stem sequence of the stem (e.g., the lower stem or the upper stem) comprises no more than about five, four, or three nucleotides. In some embodiments, the loop is an internal loop adjacent to the stem (e.g., the lower stem) and a further stem (e.g., an upper stem) comprising two complementary stem sequences. In some embodiments, the internal loop comprises a nucleic acid sequence of no more than 10, 9, or 8 nucleotides. In some embodiments, a stem sequence of the further stem (e.g., the upper stem) comprises no more than about five, four, or three nucleotides. In some embodiments, the engineered polynucleotide (e.g., the recruiting moiety) further comprises an apical loop. In some embodiments, the apical loop comprises a nucleic acid sequence of no more than 10, 9, 8, 7, 6, or 5 nucleotides.

In some embodiments of the engineered polynucleotide described herein, the recruiting moiety comprises about 10 to about 30 nucleotides, about 10 to about 25 nucleotides, or about 10 to about 20 nucleotides.

In some embodiments, the recruiting moiety is partially complementary to a post-transcriptional regulating moiety (or a regulating moiety) (e.g., a spliceosomal moiety) comprising a ribonucleoprotein complex. For example, the recruiting moiety can be partially complementary to a regulating moiety comprising a spliceosomal ribonucleoprotein complex, where the spliceosomal ribonucleoprotein complex comprises a small nuclear ribonucleic acid (snRNA). In some embodiments, the recruiting moiety is not complementary and does not bind to a target sequence described herein. For example, the recruiting moiety is not complementary and does not bind to a pre-mRNA described herein.

Structural Configurations

In some embodiments of the engineered polynucleotide described herein, one of the first and second targeting moieties is 5' with respect to the recruiting moiety, and the other of the first and second targeting moieties is 3' with respect to the recruiting moiety.

In some embodiments, the engineered polynucleotide has a structural arrangement from 5'-terminus to 3'-terminus as follows: a first targeting moiety, a recruiting moiety, and a second targeting moiety. In some embodiments, the engineered polynucleotide has a structural arrangement from 5'-terminus to 3'-terminus as follows: a second targeting moiety, a recruiting moiety, and a first targeting moiety.

Example Polynucleotides

In some embodiments of the engineered polynucleotide described herein, the engineered polynucleotide comprises about 10 to about 40 nucleotides, about 10 to about 35 nucleotides, about 10 to about 30 nucleotides, or about 10 to about 25 nucleotides. In some embodiments, the engineered polynucleotide comprises a length of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more nucleotides. In some embodiments, the engineered polynucleotide comprises a length of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or less nucleotides. In some embodiments, the engineered polynucleotide comprises a length of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50 nucleotides, or a range between any two foregoing values.

In some embodiments of the engineered polynucleotide described herein, the recruiting moiety comprises a nucleotide sequence that is at least 70%, 80%, 85%, or 90% identical or complementary to a sequence set forth in Table 3. In some embodiments, the recruiting moiety comprises a nucleotide sequence that is identical or complementary to a sequence set forth in Table 3.

TABLE 3

Example sequences of engineered polynucleotides comprising recruiting moieties and targeting moieties

| SEQ ID No. | Sequence | Nucleotide length | |
|---|---|---|---|
| 5 | gtccactaacctttcaggccagcg | 24 nt | ASMO1 |
| 6 | guccacuaaccuuucaggccagcg | 24 nt | ASMO1 |
| 7 | gcatcgtcagcttaccttgg | 20 nt | ASMO2 |
| 8 | gcaucgucagcuuaccuugg | 20 nt | ASMO2 |

In some embodiments, the engineered polynucleotide can be produced from a precursor of the engineered polynucleotide. In some cases, a precursor of the engineered polynucleotide can be linear. For example, a precursor of the engineered polynucleotide can be a linear polynucleotide transcribed from a plasmid. In another example, a precursor of the engineered polynucleotide can be constructed to be a linear polynucleotide with moieties such as a ribozyme moiety and a ligation moiety that allow for circularization of the engineered polynucleotide in a cell. The linear engineered polynucleotide with the ligation and ribozyme moieties can be transfected into a cell, where it can be circularized. In some cases, the engineered polynucleotide can be circular. In some cases, the engineered polynucleotide comprises DNA, RNA or both. In some cases, a precursor of the engineered polynucleotide comprises a precursor of the engineered polynucleotide. In some cases, a precursor of the engineered polynucleotide can be used to produce an engineered polynucleotide.

In some embodiments, the engineered polynucleotide comprises at least one secondary structure (such as those described anywhere herein). For example, the engineered polynucleotide comprises at least one, two, three, four, or more secondary structures, where the secondary structures can be any one or any combination of an apical loop, a stem, a stem loop, or an internal loop. In some embodiments, the recruiting moiety of the polynucleotide comprises at least one, two, three, four, or more secondary structures. In some embodiments, the targeting moiety does not have a secondary structure. In some embodiments, the secondary structure is an apical loop comprising at least two, three, four, five, six, seven, eight, nine, 10, or more nucleotides. In some embodiments, the apical loop is complementary and binds to the regulating moiety. In some embodiments, the apical loop is not complementary and does not bind to the regulating moiety. In some embodiments, the secondary structure is at least one stem. In some embodiments, the engineered polynucleotide comprises two stems, where one is an upper stem that is close to the apical loop and the other is a lower stem closer to the targeting moiety. In some embodiments, the upper stem comprises at least two, four, six, eight, 10, or more nucleotides, where the nucleotides are paired to form the upper stem. In some embodiments, the upper stem is complementary and binds to the regulating moiety. In some embodiments, the upper stem is not complementary and does not bind to the regulating moiety. In some embodiments, the secondary structure is a lower stem, where the lower stem comprises at least two, four, six, eight, 10, or more nucleotides, where the nucleotides are paired to form the lower stem. In some embodiments, the lower stem is complementary and binds to the regulating moiety. In some embodiments, the lower stem is not complementary and does not bind to the regulating moiety. In some embodiments, the engineered polynucleotide comprises an internal loop between the upper stem and the lower stem. In some embodiments, the internal loop comprises at least two, three, four, five, six, seven, eight, nine, 10, or more nucleotides. In some embodiments, the internal loop is complementary and binds to the regulating moiety. In some embodiments, the internal loop is not complementary and does not bind to the regulating moiety. In some embodiments, the engineered polynucleotide comprises secondary structures comprising an apical loop, an upper stem, an internal loop, and a lower stem, where the upper stem and the internal loop are at least partially complementary and bind to the regulating moiety. In some embodiments, the upper stem and the internal loop are complementary and bind to the regulating moiety comprising snRNA. In some embodiments, the snRNA is U1 snRNA such as US-A snRNA. In some embodiments, the snRNA is U2 snRNA.

In some embodiments, the nucleic acid sequence of the at least one secondary structure is partially complementary to the regulating moiety comprising the ribonucleoprotein complex. In some embodiments, the nucleic acid sequence of the at least one secondary structure is not complementary to the targeted nucleic acid sequence. In some embodiments, the engineered polynucleotide comprises at least one secondary structure of the nucleic acid. In some embodiments, the engineered polynucleotide comprises at least one, two, three, four, or more secondary structure of the nucleic acid. In some embodiments, the at least one secondary structure increases the binding between the recruiting moiety and the regulating moiety. In some embodiments, the at least one secondary structure stabilizes the assembly of the regulating moiety. In some embodiments, the at least one secondary structure stabilizes the assembly of the regulating moiety with other additional moiety. In some embodiments, the at least one secondary structure increases the efficiency of modulating the expression or activity of the gene encoding by the target sequence. In some embodiments, the at least one secondary structure increases the specificity of modulating the expression or activity of the gene encoding by the target sequence. In some embodiments, the at least one secondary structure increases the resistance of the engineered polynucleotide to degradation by hydrolysis. In some embodiments, the at least one secondary structure increases the resistance of the engineered polynucleotide to degradation by nuclease digestion. In some embodiments, the at least one secondary structure increases half-life of the engineered polynucleotide. In some embodiments, the at least one secondary structure decreases immunogenicity induced by the engineered polynucleotide.

In some embodiments, the engineered polynucleotide is characterized by a secondary structure. In some embodiments, the secondary structure comprises one or more stem-loop structures. In some embodiments, the secondary structure comprises an apical loop, an upper stem, an internal loop, and a lower stem. In some embodiments, the engineered polynucleotide comprises at least one secondary structure. In some embodiments, the first or second targeting moiety is not part of the secondary structure. In some embodiments, the engineered polynucleotide comprises at least one, two, three, four, or more secondary structure. In some embodiments, the engineered polynucleotide comprises a secondary structure comprising a stem-loop, a cruciform, a toe hold, a mismatch bulge, or any combination thereof. In some embodiments, the engineered polynucleotide comprises a secondary structure comprising an apical loop, an upper stem, an internal loop, or a lower stem. In some embodiments, the engineered polynucleotide comprises a secondary structure comprising an apical loop, an upper stem, an internal loop, and a lower stem. In some cases, a secondary structure can comprise a stem, a hairpin loop, a pseudoknot, a bulge, an internal loop, a multiloop, a G-quadruplex, or any combination thereof. In some embodiments, an engineered polynucleotide can adopt an A-form, a B-form, a Z-form, or any combination thereof. In some embodiments, the secondary structure is formed based on, at least partially, the nucleotide sequence of the engineered polynucleotide. In some embodiments, the secondary structure is formed within the nucleotide sequence of the engineered polynucleotide.

In some embodiments, the at least one secondary structure increases the binding between the recruiting moiety and the regulating moiety. In some embodiments, the at least one secondary structure increases the binding between the recruiting moiety and the regulating moiety by at least 10%, 20%, 30%, 40%, 50%, 60%, 70%, 80%, 90%, 2 fold, 3 fold, 4 fold, 5 fold, 10 fold, or more compared to the binding between the recruiting moiety without the secondary structure to the regulating moiety.

In some embodiments, the at least one chemical modification increases the binding between the recruiting moiety and the regulating moiety. In some embodiments, the at least one chemical modification increases the binding between the recruiting moiety and the regulating moiety by at least 10%, 20%, 30%, 40%, 50%, 60%, 70%, 80%, 90%, 2 fold, 3 fold, 4 fold, 5 fold, 10 fold, or more compared to the binding between the recruiting moiety without the chemical modification to the regulating moiety.

In some embodiments, the at least one chemical modification of the engineered polynucleotide stabilizes the assembly of the spliceosome comprising the regulating moiety, when the regulating moiety is associated with the target sequence. In some embodiments, the assembly of the spliceosome comprising the regulating moiety is at least 10%, 20%, 30%, 40%, 50%, 60%, 70%, 80%, 90%, 2 fold, 3 fold, 4 fold, 5 fold, 10 fold, or more stabilized by the engineered polynucleotide comprising the chemical modification compared to a comparable polynucleotide without the chemical modification. In some embodiments, the regulating moiety is U1 (U1SNP), U2 (U2SNP), U4, U5, U6, U11, U12, U14, or U16 of the spliceosome. In some embodiments, the regulating moiety is U1 SNP of the spliceosome. In some embodiments, the regulating moiety is U1-A of the spliceosome. In some embodiments, the regulating moiety is U2SNP of the spliceosome. In some embodiments, the at least one chemical modification of the engineered polynucleotide stabilizes the assembly of the spliceosome comprising the regulating moiety and at least one additional moiety. For example, the at least one chemical modification of the engineered polynucleotide stabilizes the assembly of the spliceosome comprising the regulating moiety comprising U1-A and at least one additional moiety comprising U1-70K, UC-1, SmD1, SmD2, SmD3, SmE, SmF, or SmG. In some embodiments, the at least one additional moiety is U4, U5, U6, U11, U12, U14, or U16 of the spliceosome.

In some embodiments, the at least one chemical modification increases the efficiency of the engineered polynucleotide modulating the expression or activity of the gene encoding by the target sequence compared to a comparable polynucleotide without the chemical modification. In some embodiments, the efficiency of the engineered polynucleotide modulating the expression or activity of the gene encoding by the target sequence is increased by at least 10%, 20%, 30%, 40%, 50%, 60%, 70%, 80%, 90%, 2 fold, 3 fold, 4 fold, 5 fold, 10 fold, or more compared to the efficient of the comparable polynucleotide without the chemical modification modulating the expression or activity of the gene encoding by the target sequence.

In some embodiments, the at least one chemical modification increases the specificity of the engineered polynucleotide modulating the expression or activity of the gene encoding by the target sequence compared to a comparable polynucleotide without the chemical modification. In some embodiments, the specificity of the engineered polynucleotide modulating the expression or activity of the gene encoding by the target sequence is increased by at least 10%, 20%, 30%, 40%, 50%, 60%, 70%, 80%, 90%, 2 fold, 3 fold, 4 fold, 5 fold, 10 fold, or more compared to the efficient of the comparable polynucleotide without the chemical modification modulating the expression or activity of the gene encoding by the target sequence.

In some embodiments, the at least one chemical modification increases the resistance of the engineered polynucleotide to degradation by hydrolysis. In some embodiments, the at least one chemical modification increases the resistance of the engineered polynucleotide to degradation by hydrolysis compared to a resistance of a comparable engineered polynucleotide without the chemical modification. In some embodiments, the resistance to degradation by hydrolysis of the engineered polynucleotide comprising the at least one chemical modification is increased by at least 10%, 20%, 30%, 40%, 50%, 60%, 70%, 80%, 90%, 2 fold, 3 fold, 4 fold, 5 fold, 10 fold, or more compared to the resistance of the comparable engineered polynucleotide without the chemical modification.

In some embodiments, the at least one chemical modification increases the resistance of the engineered polynucleotide to degradation by nuclease digestion. In some embodiments, the at least one chemical modification increases the resistance of the engineered polynucleotide to degradation by nuclease digestion compared to a resistance of a comparable engineered polynucleotide without the chemical modification. In some embodiments, the resistance to degradation by nuclease digestion of the engineered polynucleotide comprising the at least one chemical modification is increased by at least 10%, 20%, 30%, 40%, 50%, 60%, 70%, 80%, 90%, 2 fold, 3 fold, 4 fold, 5 fold, 10 fold, or more compared to the resistance of the comparable engineered polynucleotide without the chemical modification.

In some embodiments, the at least one chemical modification increases half-life of the engineered polynucleotide compared to a half-life of a comparable engineered polynucleotide without the chemical modification. In some embodiments, the half-life of the engineered polynucleotide comprising the at least one chemical modification is increased by at least 10%, 20%, 30%, 40%, 50%, 60%, 70%, 80%, 90%, 2 fold, 3 fold, 4 fold, 5 fold, 10 fold, or more compared to the half-life of the comparable engineered polynucleotide without the chemical modification.ne chemical modification increases half-life of the engineered polynucleotide.

In some embodiments, the at least one chemical modification decreases immunogenicity induced by the engineered polynucleotide. In some embodiments, the at least one chemical modification decreases immunogenicity induced by the engineered polynucleotide compared to an immunogenicity of a comparable engineered polynucleotide without the chemical modification. In some embodiments, the immunogenicity of the engineered polynucleotide comprising the at least one chemical modification is decreased by at least 10%, 20%, 30%, 40%, 50%, 60%, 70%, 80%, 90%, 2 fold, 3 fold, 4 fold, 5 fold, 10 fold, or more compared to the immunogenicity of the comparable engineered polynucleotide without the chemical modification.

Chemical Modification(s)

In some embodiments described herein, the engineered polynucleotide comprises at least one chemical modification.

In some embodiments, all nucleotides of a targeting moiety are linked by phosphorothioate bonds. In some embodiments, all nucleotides of a targeting moiety comprise a 2' O-methyl modification. 2' modifications can prevent nuclease degradation and/or increase the affinity of the targeting moiety to a pre-mRNA target.

In some embodiments, all nucleotides of a recruiting moiety are linked by phosphorothioate bonds. In some embodiments, three nucleotides of a recruiting moiety comprise a 2' O-methyl modification. The 2' modifications can induce a change in the molecular dynamics of the recruiting moiety, thereby facilitating a conformational alteration of stem-loop II of U1-snRNA and binding of the recruiting moiety to U1-snRNA.

In some embodiments, the engineered polynucleotide comprises at least one 2'-modified (e.g., 2'-methoxy, 2'-methoxymethyl, or 2'-methoxyethyl) nucleotides. In some embodiments, at least about 50%, 60%, 70%, 80%, or 90% nucleotides of the engineered polynucleotide are chemically modified nucleotides. In some embodiments, at least about 50%, 60%, 70%, 80%, or 90% nucleotides of the engineered polynucleotide are 2'-modified (e.g., 2'-methoxy, 2'-methoxymethyl, or 2'-methoxyethyl) nucleotides. In some embodiments, the engineered polynucleotide comprises at least one phosphorothioate internucleotide bond. In some embodiments, at least about 50%, 60%, 70%, 80%, or 90% internucleotide linkages of the engineered polynucleotide are chemically modified. In some embodiments, at least about 50%, 60%, 70%, 80%, or 90% internucleotide linkages are phosphorathioate.

In some embodiments, the engineered polynucleotide comprises at least one chemical modification of the nucleic acid. In some embodiments, the engineered polynucleotide comprises at least one, two, three, four, or more chemical modification of the nucleic acid. In some embodiments, the at least one chemical modification increases the binding between the recruiting moiety and the regulating moiety. In some embodiments, the at least one chemical modification stabilizes the assembly of the regulating moiety. In some embodiments, the at least one chemical modification stabilizes the assembly of the regulating moiety with other additional moiety. In some embodiments, the at least one chemical modification increases the efficiency of modulating the expression or activity of the gene encoding by the target sequence. In some embodiments, the at least one chemical modification increases the specificity of modulating the expression or activity of the gene encoding by the target sequence. In some embodiments, the at least one chemical modification increases the resistance of the engineered polynucleotide to degradation by hydrolysis. In some embodiments, the at least one chemical modification increases the resistance of the engineered polynucleotide to degradation by nuclease digestion. In some embodiments, the at least one chemical modification increases half-life of the engineered polynucleotide. In some embodiments, the at least one chemical modification decreases immunogenicity induced by the engineered polynucleotide.

In some embodiments, the chemical modifications of the engineered polynucleotide comprise at least one substitution of one or both of non-linking phosphate oxygen atoms in a phosphodiester backbone linkage of the engineered polynucleotide. In some embodiments, the at least one chemical modification of the engineered polynucleotide comprises a substitution of one or more of linking phosphate oxygen atoms in a phosphodiester backbone linkage of the engineered polynucleotide. A non-limiting example of a chemical modification of a phosphate oxygen atom is a sulfur atom. Additional non-limiting examples are included in Table 3. In some embodiments, the chemical modifications of the engineered polynucleotide comprise at least one chemical modification to a sugar of a nucleotide of the engineered polynucleotide. In some embodiments, the chemical modifications of the engineered polynucleotide comprise at least one chemical modification to the sugar of the nucleotide, where the chemical modification comprises at least one locked nucleic acid (LNA). In some embodiments, the chemical modifications of the engineered polynucleotide comprise at least one chemical modification to the sugar of the nucleotide of the engineered polynucleotide comprising at least one unlocked nucleic acid (UNA). In some embodiments, the chemical modifications of the engineered polynucleotide comprise at least one chemical modification to the sugar comprising a modification of a constituent of the sugar, where the sugar is a ribose sugar. In some embodiments, the chemical modifications of the engineered polynucleotide comprise at least one chemical modification to the constituent of the ribose sugar of the nucleotide of the engineered polynucleotide comprising a 2'-O-Methyl group. In some embodiments, the chemical modification, instead of 2'-O-Methyl group modification, comprises a 2'-F-RNA. In such case, the 2'-F-RNA and pre-mRNA duplexes does not activate RNase H (degradation by nuclease digestion) and are more stable as determined by higher melting temperature (Tm) than 2'-O-methyl-RNA and pre-mRNA duplex.

In some embodiments, the chemical modifications of the engineered polynucleotide comprise at least one chemical modification comprising replacement of a phosphate moiety of the engineered polynucleotide with a dephospho linker. In some embodiments, the chemical modifications of the engineered polynucleotide comprise at least one chemical modification of a phosphate backbone of the engineered polynucleotide. In some embodiments, the engineered polynucleotide comprises a phosphothioate group. In some embodiments, the chemical modifications of the engineered polynucleotide comprise at least one chemical modification comprising a modification to a base of a nucleotide of the engineered polynucleotide. In some embodiments, the chemical modifications of the engineered polynucleotide comprise at least one chemical modification comprising an unnatural base of a nucleotide. In some embodiments, the chemical modifications of the engineered polynucleotide comprise at least one chemical modification comprising a morpholino group, a cyclobutyl group, pyrrolidine group, or peptide nucleic acid (PNA) nucleoside surrogate. In some embodiments, the chemical modifications of the engineered polynucleotide comprise at least one chemical modification comprising at least one stereopure nucleic acid. In some embodiments, the at least one chemical modification can be positioned proximal to a 5' end of the engineered polynucleotide. In some embodiments, the at least one chemical modification can be positioned proximal to a 3' end of the engineered polynucleotide. In some embodiments, the at least one chemical modification can be positioned proximal to both 5' and 3' ends of the engineered polynucleotide.

In some embodiments, the at least one chemical modification of the engineered polynucleotide comprises a modification of any one of or any combination of: modification of one or both of the non-linking phosphate oxygens in the phosphodiester backbone linkage; modification of one or more of the linking phosphate oxygens in the phosphodiester backbone linkage; modification of a constituent of the ribose sugar; Replacement of the phosphate moiety with "dephospho" linkers; modification or replacement of a naturally occurring nucleobase; modification of the ribose-phosphate backbone; modification of 5' end of polynucleotide; modification of 3' end of polynucleotide; modification of the deoxyribose phosphate backbone; substitution of the phosphate group; modification of the ribophosphate backbone; modifications to the sugar of a nucleotide; modifications to the base of a nucleotide; or stereopure of nucleotide. Example chemical modification to the engineered polynucleotide can be seen in Table 4.

phate oxygens in the phosphodiester backbone linkage or modification of one or more of the linking phosphate oxygens in the phosphodiester backbone linkage. As used herein, "alkyl" is meant to refer to a saturated hydrocarbon group which is straight-chained or branched. Example alkyl groups include methyl (Me), ethyl (Et), propyl (e.g., n-propyl or isopropyl), butyl (e.g., n-butyl, isobutyl, or t-butyl), or pentyl (e.g., n-pentyl, isopentyl, or neopentyl). An alkyl group can contain from 1 to about 20, from 2 to about 20, from 1 to about 12, from 1 to about 8, from 1 to about 6, from 1 to about 4, or from 1 to about 3 carbon atoms. As used herein, "aryl" refers to monocyclic or polycyclic (e.g., having 2, 3, or 4 fused rings) aromatic hydrocarbons such as, for example, phenyl, naphthyl, anthracenyl, phenanthrenyl, indanyl, or indenyl. In some embodiments, aryl groups have from 6 to about 20 carbon atoms. As used herein, "alkenyl"

TABLE 4

Example Chemical Modification

| Modification of engineered polynucleotide | Example(s) |
| --- | --- |
| Modification of one or both of the non-linking phosphate oxygens in the phosphodiester backbone linkage | sulfur (S), selenium (Se), BR3 (wherein R can be, e.g., hydrogen, alkyl, or aryl), C (e.g., an alkyl group, an aryl group, and the like), H, NR2, wherein R can be, e.g., hydrogen, alkyl, or aryl, or wherein R can be, e.g., alkyl or aryl |
| Modification of one or more of the linking phosphate oxygens in the phosphodiester backbone linkage | sulfur (S), selenium (Se), BR3 (wherein R can be, e.g., hydrogen, alkyl, or aryl), C (e.g., an alkyl group, an aryl group, and the like), H, NR2, wherein R can be, e.g., hydrogen, alkyl, or aryl, or wherein R can be, e.g., alkyl or aryl |
| Replacement of the phosphate moiety with "dephospho" linkers | methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, or methyleneoxymethylimino |
| Modification or replacement of a naturally occurring nucleobase | Nucleic acid analog |
| Modification of the ribose-phosphate backbone | phosphorothioate, phosphonothioacetate, phosphoroselenates, boranophosphates, borano phosphate esters, hydrogen phosphonates, phosphonocarboxylate, phosphoroamidates, alkyl or aryl phosphonates, phosphonoacetate, or phosphotriesters |
| Modification of 5' end of polynucleotide | 5' cap or modification of 5' cap-OH |
| Modification of 3' end of polynucleotide | 3' tail or modification of 3' end-OH |
| Modification of the deoxyribose phosphate backbone | phosphorothioate, phosphonothioacetate, phosphoroselenates, borano phosphates, borano phosphate esters, hydrogen phosphonates, phosphoroamidates, alkyl or aryl phosphonates, or phosphotriesters |
| Substitution of the phosphate group | methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, or methyleneoxymethylimino. |
| Modification of the ribophosphate backbone | morpholino, cyclobutyl, pyrrolidine, or peptide nucleic acid (PNA) nucleoside surrogates |
| Modifications to the sugar of a nucleotide | Locked nucleic acid (LNA), unlocked nucleic acid (UNA), or bridged nucleic acid (BNA) |
| Modification of engineered polynucleotide | Example(s) |
| Modification of a constituent of the ribose sugar | 2'-O-methyl, 2'-O-methoxy-ethyl (2'-M0E), 2'-fluoro, 2'-aminoethyl, 2'-deoxy-2'-fuloarabinou-cleic acid, 2'-deoxy, 2'-O-methyl, 3'-phosphorothioate, 3'-phosphonoacetate (PACE), or 3'-phosphonothioacetate (thioPACE) |
| Modifications to the base of a nucleotide | Modification of A, T, C, G, or U |
| Stereopure of nucleotide | S conformation of phosphorothioate or R conformation of phosphorothioate |

Modification of Phosphate Backbone

In some embodiments, the chemical modification comprises modification of one or both of the non-linking phosrefers to an aliphatic group containing at least one double bond. As used herein, "alkynyl" refers to a straight or branched hydrocarbon chain containing 2-12 carbon atoms and characterized in having one or more triple bonds. Examples of alkynyl groups can include ethynyl, propargyl, or 3-hexynyl. "Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. "Cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl. "Heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl. "Heteroaryl" refers to a monovalent radical of a heteroaromatic ring system. Examples of heteroaryl moieties can include imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

In some embodiments, the phosphate group of a chemically modified nucleotide can be modified by replacing one or more of the oxygens with a different substituent. In some embodiments, the chemically modified nucleotide can include replacement of an unmodified phosphate moiety with a modified phosphate as described herein. In some embodiments, the modification of the phosphate backbone can include alterations that result in either an uncharged linker or a charged linker with unsymmetrical charge distribution. Examples of modified phosphate groups can include phosphorothioate, phosphonothioacetate, phosphoroselenates, boranophosphates, boranophosphate esters, hydrogen phosphonates, phosphoroamidates, alkyl or aryl phosphonates and phosphotriesters. In some embodiments, one of the non-bridging phosphate oxygen atoms in the phosphate backbone moiety can be replaced by any of the following groups: sulfur (S), selenium (Se), BR3 (wherein R can be, e.g., hydrogen, alkyl, or aryl), C (e.g., an alkyl group, an aryl group, and the like), H, NR2 (wherein R can be, e.g., hydrogen, alkyl, or aryl), or (wherein R can be, e.g., alkyl or aryl). The phosphorous atom in an unmodified phosphate group can be achiral. However, replacement of one of the non-bridging oxygens with one of the above atoms or groups of atoms can render the phosphorous atom chiral. A phosphorous atom in a phosphate group modified in this way is a stereogenic center. The stereogenic phosphorous atom can possess either the "R" configuration (herein Rp) or the "S" configuration (herein Sp). In some cases, the engineered polynucleotide comprises stereopure nucleotides comprising S conformation of phosphorothioate or R conformation of phosphorothioate. In some embodiments, the chiral phosphate product is present in a diastereomeric excess of 50%, 60%, 70%, 80%, 90%, or more. In some embodiments, the chiral phosphate product is present in a diastereomeric excess of 95%. In some embodiments, the chiral phosphate product is present in a diastereomeric excess of 96%. In some embodiments, the chiral phosphate product is present in a diastereomeric excess of 97%. In some embodiments, the chiral phosphate product is present in a diastereomeric excess of 98%. In some embodiments, the chiral phosphate product is present in a diastereomeric excess of 99%. In some embodiments, both non-bridging oxygens of phosphorodithioates can be replaced by sulfur. The phosphorus center in the phosphorodithioates can be achiral which precludes the formation of oligoribonucleotide diastereomers. In some embodiments, modifications to one or both non-bridging oxygens can also include the replacement of the non-bridging oxygens with a group independently selected from S, Se, B, C, H, N, and OR (R can be, e.g., alkyl or aryl). In some embodiments, the phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either or both of the linking oxygens.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino ($-CH_2-N(CH_3)-O-CH_2-$), thiodiester ($-O-C(O)-S-$), thionocarbamate ($-O-C(O)(NH)-S-$); siloxane ($-O-Si(H)_2-O-$); and N,N'-dimethylhydrazine ($-CH_2-N(CH_3)-N(CH_3)$). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and can be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like.

In some cases, backbone modification comprises replacing the phosphodiester linkage with an alternative moiety such as an anionic, neutral or cationic group. Examples of such modifications include: anionic internucleotide linkage; N3' to P5' phosphoramidate modification; boranophosphate DNA; prooligonucleotides; neutral internucleotide linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos. A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleotide linkages, mixed heteroatom and alkyl or cycloalkyl internucleotide linkages, or one or more short chain heteroatomic or heterocyclic internucleotide linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. It is also understood in a nucleotide substitute that both the sugar and the phosphate moieties of the nucleotide can be replaced, by for example an amide type linkage (aminoethylglycine) (PNA). It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1-di-O-hexadecyl-rac-glycero-S—H-phosphonate, a polyamine or a polyethylene glycol chain, or adamantane acetic acid, a palmityl moiety, or an octadecylamine or hexylamino-carbonyl-oxycholesterol moiety.

In some embodiments, the chemical modification described herein comprises modification of a phosphate backbone. In some embodiments, the engineered polynucleotide described herein comprises at least one chemically modified phosphate backbone. Example chemically modification of the phosphate group or backbone can include replacing one or more of the oxygens with a different substituent. Furthermore, the modified nucleotide present in the engineered polynucleotide can include the replacement of an unmodified phosphate moiety with a modified phosphate as described herein. In some embodiments, the modification of the phosphate backbone can include alterations resulting in either an uncharged linker or a charged linker with unsymmetrical charge distribution. Example modified phosphate groups can include, phosphorothioate, phosphonothioacetate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp). In such case, the chemically modified engineered polynucleotide can be stereopure (e.g. S or R confirmation). In some cases, the chemically modified engineered polynucleotide comprises stereopure phosphate modification. For example, the chemically modified engineered polynucleotide comprises S conformation of phosphorothioate or R conformation of phosphorothioate.

Phosphorodithioates have both non-bridging oxygens replaced by sulfur. The phosphorus center in the phosphorodithioates is achiral which precludes the formation of oligoribonucleotide diastereomers. In some embodiments, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of Phosphate Moiety

In some embodiments, at least one phosphate group of the engineered polynucleotide can be chemically modified. In some embodiments, the phosphate group can be replaced by non-phosphorus containing connectors. In some embodiments, the phosphate moiety can be replaced by dephospho linker. In some embodiments, the charge phosphate group can be replaced by a neutral group. In some cases, the phosphate group can be replaced by methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In some embodiments, nucleotide analogs described herein can also be modified at the phosphate group. Modified phosphate group can include modification at the linkage between two nucleotides with phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates (e.g. 3'-amino phosphoramidate and aminoalkylphosphoramidates), thionophosphoramidates, thionoalkylphosphonates, thionoalkylphosphotriesters, and boranophosphates. The phosphate or modified phosphate linkage between two nucleotides can be through a 3'-5' linkage or a 2'-5' linkage, and the linkage contains inverted polarity such as 3'-5' to 5'-3' or 2'-5' to 5'-2'.

Substitution of Phosphate Group

In some embodiments, the chemical modification described herein comprises modification by replacement of a phosphate group. In some embodiments, the engineered polynucleotide described herein comprises at least one chemically modification comprising a phosphate group substitution or replacement. Example phosphate group replacement can include non-phosphorus containing connectors. In some embodiments, the phosphate group substitution or replacement can include replacing charged phosphate group can by a neutral moiety. Example moieties which can replace the phosphate group can include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Modification of the Ribophosphate Backbone

In some embodiments, the chemical modification described herein comprises modifying ribophosphate backbone of the engineered polynucleotide. In some embodiments, the engineered polynucleotide described herein comprises at least one chemically modified ribophosphate backbone. Example chemically modified ribophosphate backbone can include scaffolds that can mimic nucleic acids can also be constructed wherein the phosphate linker and ribose sugar are replaced by nuclease resistant nucleoside or nucleotide surrogates. In some embodiments, the nucleobases can be tethered by a surrogate backbone. Examples can include morpholino, cyclobutyl, pyrrolidine and peptide nucleic acid (PNA) nucleoside surrogates.

Modification of Sugar

In some embodiments, the chemical modification described herein comprises modifying of sugar. In some embodiments, the engineered polynucleotide described herein comprises at least one chemically modified sugar. Example chemically modified sugar can include 2' hydroxyl group (OH) modified or replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom. Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH2CH_2OR$, wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In some embodiments, the "oxy"-2' hydroxyl group modification can include (LNA, in which the 2' hydroxyl can be connected, e.g., by a $C_{i-6}$ alkylene or Cj-6 heteroalkylene bridge, to the 4' carbon of the same ribose sugar, where example bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the "oxy"-2' hydroxyl group modification can include the methoxyethyl group (MOE), ($OCH_2CH_2OCH_3$, e.g., a PEG derivative). In some cases, the deoxy modifications can include hydrogen (i.e. deoxyribose sugars, e.g., at the overhang portions of partially dsRNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH2CH_2$-amino (wherein amino can be, e.g., as described herein), NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which can be optionally substituted with e.g., an amino as described herein. In some instances, the sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the I' position on the sugar, e.g., alpha-nucleosides. The modified nucleic acids can also include "abasic" sugars, which lack a nucleobase at C—. The abasic sugars can also be further modified at one or more of the constituent sugar atoms. The modified nucleic acids can also include one or more sugars that are in the L form, e.g. L-nucleosides. In some aspects, the engineered polynucleotide described herein includes the sugar group ribose, which is a 5-membered ring having an oxygen. Example modified nucleosides and modified nucleotides can include replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6-or 7-membered ring having an additional carbon or heteroatom, such as for example, anhydrohexitol, altritol, mannitol, cyclohexanyl, cyclohexenyl, and morpholino that also has a phosphoramidate backbone). In some embodiments, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid. In some embodiments, the modifications to the sugar of the engineered polynucleotide comprises modifying the engineered polynucleotide to include locked nucleic acid (LNA), unlocked nucleic acid (UNA), or bridged nucleic acid (BNA).

Modification of a Constituent of the Ribose Sugar

In some embodiments, the engineered polynucleotide described herein comprises at least one chemical modification of a constituent of the ribose sugar. In some embodiments, the chemical modification of the constituent of the ribose sugar can include 2'-O-methyl, 2'-O-methoxy-ethyl (2'-MOE), 2'-fluoro, 2'-aminoethyl, 2'-deoxy-2'-fuloarabinou-cleic acid, 2'-deoxy, 2'-O-methyl, 3'-phosphorothioate, 3'-phosphonoacetate (PACE), or 3'-phosphonothioacetate (thioPACE). In some embodiments, the chemical modification of the constituent of the ribose sugar comprises unnatural nucleic acid. In some instances, the unnatural nucleic acids include modifications at the 5'-position and the 2'-position of the sugar ring, such as 5'-$CH_2$-substituted 2'-O-protected nucleosides. In some cases, unnatural nucleic acids include amide linked nucleoside dimers have been prepared for incorporation into oligonucleotides wherein the 3' linked nucleoside in the dimer (5' to 3') comprises a 2'-$OCH_3$ and a 5'-(S)—$CH_3$. Unnatural nucleic acids can include 2'-substituted 5'-$CH_2$ (or 0) modified nucleosides. Unnatural nucleic acids can include 5'-methylenephosphonate DNA and RNA monomers, and dimers. Unnatural nucleic acids can include 5'-phosphonate monomers having a 2'-substitution and other modified 5'-phosphonate monomers. Unnatural nucleic acids can include 5'-modified methylenephosphonate monomers. Unnatural nucleic acids can include analogs of 5' or 6'-phosphonate ribonucleosides comprising a hydroxyl group at the 5' and/or 6'-position. Unnatural nucleic acids can include 5'-phosphonate deoxyribonucleoside monomers and dimers having a 5'-phosphate group. Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/ or 2' substituent groups; bridging of two ring atoms to form bicyclic nucleic acids; replacement of the ribosyl ring oxygen atom with S, N(R), or C(R$_1$)(R$_2$) (R═H, C$_1$-C$_{12}$ alkyl or a protecting group); and combinations thereof.

In some instances, the engineered polynucleotide described herein comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety can be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy-or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol-like ribonucleosides.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S-or N-alkynyl; or O-alkyl-O-alkyl, wherein the alkyl, alkenyl and alkynyl can be substituted or unsubstituted C$_1$ to C$_{10}$, alkyl or C$_2$ to C$_{10}$ alkenyl and alkynyl. 2' sugar modifications also include but are not limited to-O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$ONH$_2$, and —O(CH$_2$)$_n$ON[(CH$_2$)n CH$_3$)]$_2$, where n and m are from 1 to about 10. Other chemical modifications at the 2' position include but are not limited to: C$_1$ to C$_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Chemically modified sugars also include those that contain modifications at the bridging ring oxygen, such as CH$_2$ and S. Nucleotide sugar analogs can also have sugar mimetics such as cyclobutyl moieties in place of the pentofuranosyl sugar. Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—(C$_1$-C$_{10}$ alkyl), OCF$_3$, O(CH$_2$)$_2$SCH$_3$, O(CH$_2$)$_2$—O—N(R$_m$)(R$_n$), and O—CH$_2$—C(═O)—N(R$_m$) (R$_n$), where each R$_m$ and R$_n$ is, independently, H or substituted or unsubstituted C$_1$-C$_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH (CH$_2$OCH$_3$)—O-2', and analogs thereof; 4'-C(CH$_3$)(CH$_3$)—O-2'and analogs thereof.

Modifications on the Base of Nucleotide

In some embodiments, the chemical modification described herein comprises modification of the base of nucleotide (e.g. the nucleobase). Example nucleobases can include adenine (A), thymine (T), guanine (G), cytosine (C), and uracil (U). These nucleobases can be modified or replaced to in the engineered polynucleotide described herein. The nucleobase of the nucleotide can be independently selected from a purine, a pyrimidine, a purine or pyrimidine analog. In some embodiments, the nucleobase can be naturally occurring or synthetic derivatives of a base.

In some embodiments, the chemical modification described herein comprises modifying an uracil. In some embodiments, the engineered polynucleotide described herein comprises at least one chemically modified uracil. Example chemically modified uracil can include pseudouridine, pyridin-4-one ribonucleoside, 5-aza-uridine, 6-aza-uridine, 2-thio-5-aza-uridine, 2-thio-uridine, 4-thio-uridine, 4-thio-pseudouridine, 2-thio-pseudouridine, 5-hydroxy-uridine, 5-aminoallyl-uridine, 5-halo-uridine (e.g., 5-iodo-uridine or 5-bromo-uridine), 3-methyl-uridine, 5-methoxy-uridine, uridine 5-oxyacetic acid, uridine 5-oxyacetic acid methyl ester, 5-carboxymethyl-uridine, 1-carboxymethyl-pseudouridine, 5-carboxyhydroxymethyl-uridine, 5-carboxyhydroxymethyl-uridine methyl ester, 5-methoxycarbonylmethyl-uridine, 5-methoxycarbonylmethyl-2-thio-uridine, 5-aminomethyl-2-thio-uridine, 5-methylaminomethyl-uridine, 5-methylaminomethyl-2-thio-uridine, 5-methylaminomethyl-2-seleno-uridine, 5-carbamoylmethyl-uridine, 5-carboxymethylaminomethyl-uridine, 5-carboxymethylaminomethyl-2-thio-uridine, 5-propynyl-uridine, 1-propynyl-pseudouridine, 5-taurinomethyl-uridine, 1-taurinomethyl-pseudouridine, 5-taurinomethyl-2-thio-uridine, l-taurinomethyl-4-thio-pseudouridine, 5-methyl-uridine, 1 methyl-pseudouridine, 5-methyl-2-thio-uridine, 1-methyl-4-thio-pseudouridine, 4-thio-1-methyl-pseudouridine, 3-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 5,6-dihydrouridine, 5-methyl-dihydrouridine, 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine, 1-methyl-3-(3-amino-3-carboxypropy pseudouridine, 5-(isopentenylaminomethyl) uridine, 5-(isopentenylaminomethyl)-2-thio-uridine, a-thio-uridine, 2'-O-methyl-uridine, 5,2'-O-dimethyl-uridine, 2'-O-methyl-pseudouridine, 2-thio-2'-O-methyl-uridine, 5-methoxycarbonylmethyl-2'-O-methyl-uridine, 5-carbamoylmethyl-2'-O-methyl-uridine, 5-carboxymethylaminomethyl-2'-O-methyl-uridine, 3,2'-O-dimethyl-uridine, 5-(isopentenylaminomethyl)-2'-O-methyl-uridine, 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

In some embodiments, the chemical modification described herein comprises modifying a cytosine. In some embodiments, the engineered polynucleotide described herein comprises at least one chemically modified cytosine. Example chemically modified cytosine can include 5-azacytidine, 6-aza-cytidine, pseudoisocytidine, 3-methyl-cytidine, N4-acetyl-cytidine, 5-formyl-cytidine, N4-methyl-cytidine, 5-methyl-cytidine, 5-halo-cytidine, 5-hydroxymethyl-cytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine, a-thio-cytidine, 2'-O-methyl-cytidine, 5,2'-O-dimethyl-cytidine, N4-acetyl-2'-O-methyl-cytidine, N4,2'-O-dimethyl-cytidine, 5-formyl-2'-O-methyl-cytidine, N4,N4,2'-O-trimethyl-cytidine, 1-thio-cytidine, 2'-F-ara-cytidine, 2'-F-cytidine, and 2'-OH-ara-cytidine.

In some embodiments, the chemical modification described herein comprises modifying a adenine. In some embodiments, the engineered polynucleotide described herein comprises at least one chemically modified adenine. Example chemically modified adenine can include 2-aminopurine, 2,6-diaminopurine, 2-amino-6-halo-purine (e.g., 2-amino-6-chloro-purine), 6-halo-purine (e.g., 6-chloi-purine), 2-amino-6-methyl-purine, 8-azido-adenosine, 7-deaza-adenine, 7-deaza-8-aza-adenine, 7-deaza-2-aminopurine, 7-deaza-8-aza-2-amino-purine, 7-deaza-2,6-diaminopurine, 7-deaza-8-aza-2,6-diaminopurine, 1-methyladenosine, 2-methyl-adenine, N6-methyl-adenosine, 2-methylthio-N6-methyl-adenosine, N6-isopentenyl-adenosine, 2-methylthio-N6-isopentenyl-adenosine, N6-(cis-hydroxyisopentenyl) adenosine, 2-methylthio-N6-(cis-hydroxyisopentenyl) adenosine, N6-glycinylcarbamoyl-adenosine, N6-threonylcarbamoyl-adenosine, N6-methyl-N6-threonylcarbamoyl-adenosine, 2-methylthio-N6-threonylcarbamoyl-adenosine, N6, N6-dimethyl-adenosine, N6-hydroxynorvalylcarbamoyl-adenosine, 2-methylthio-N6-hydroxynorvalylcarbamoyl-adenosine, N6-acetyl-adenosine, 7-methyl-adenine, 2-methylthio-adenine, 2-methoxy-adenine, a-thio-adenosine, 2'-O-methyl-adenosine, N6, 2'-O-dimethyl-adenosine, N6-Methyl-2'-deoxyadenosine, N6, N6, 2'-O-trimethyl-adenosine, 1,2'-O-dimethyl-adenosine, 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the chemical modification described herein comprises modifying a guanine. In some embodiments, the engineered polynucleotide described herein comprises at least one chemically modified guanine. Example chemically modified guanine can include inosine, 1-methyl-inosine, wyosine, methylwyosine, 4-demethyl-wyosine, isowyosine, wybutosine, peroxywybutosine, hydroxywybutosine, undemriodified hydroxywybutosine, 7-deaza-guanosine, queuosine, epoxyqueuosine, galactosyl-queuosine, mannosyl-queuosine, 7-cyano-7-deaza-guanosine, 7-aminomethyl-7-deaza-guanosine, archaeosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methyl-guanosine, N2-methyl-guanosine, N2, N2-dimethyl-guanosine, N2, 7-dimethyl-guanosine, N2, N2, 7-dimethyl-guanosine, 8-oxo-guanosine, 7-methyl-8-oxo-guanosine, 1-meththio-guanosine, N2-methyl-6-thio-guanosine, N2,N2-dimethyl-6-thio-guanosine, a-thio-guanosine, 2'-O-methyl-guanosine, N2-methyl-2'-O-methyl-guanosine, N2,N2-dimethyl-2'-O-methyl-guanosine, 1-methyl-2'-O-methyl-guanosine, N2, 7-dimethyl-2'-O-methyl-guanosine, 2'-O-methyl-inosine, 1, 2'-O-dimethyl-inosine, 6-O-phenyl-2'-deoxyinosine, 2'-O-ribosylguanosine, 1-thio-guanosine, 6-O-methyguanosine, $0^6$-Methyl-2'-deoxyguanosine, 2'-F-ara-guanosine, and 2'-F-guanosine.

In some cases, the chemical modification of the engineered polynucleotide can include introducing or substituting a nucleic acid analog or an unnatural nucleic acid into the engineered polynucleotide. In some embodiments, nucleic acid analog can be any one of the chemically modified nucleic acid described herein. Example nucleic acid analog can be found in PCT/US2015/025175, PCT/US2014/050423, PCT/US2016/067353, PCT/US2018/041503, PCT/US18/041509, PCT/US2004/011786, or PCT/US2004/011833, all of which are expressly incorporated by reference in their entireties. The chemically modified nucleotide described herein can include a variant of guanosine, uridine, adenosine, thymidine, and cytosine, including any natively occurring or non-natively occurring guanosine, uridine, adenosine, thymidine or cytidine that has been altered chemically, for example by acetylation, methylation, hydroxylation. Example chemically modified nucleotide can include 1-methyl-adenosine, 1-methyl-guanosine, 1-methyl-inosine, 2,2-dimethyl-guanosine, 2,6-diaminopurine, 2'-amino-2'-deoxyadenosine, 2'-amino-2'-deoxycytidine, 2'-amino-2'-deoxyguanosine, 2'-amino-2'-deoxyuridine, 2-amino-6-chloropurineriboside, 2-aminopurine-riboside, 2'-araadenosine, 2'-aracytidine, 2'-arauridine, 2'-azido-2'-deoxyadenosine, 2'-azido-2'-deoxycytidine, 2'-azido-2'-deoxyguanosine, 2'-azido-2'-deoxyuridine, 2-chloroadenosine, 2'-fluoro-2'-deoxyadenosine, 2'-fluoro-2'-deoxycytidine, 2'-fluoro-2'-deoxyguanosine, 2'-fluoro-2'-deoxyuridine, 2'-fluorothymidine, 2-methyl-adenosine, 2-methyl-guanosine, 2-methyl-thio-N6-isopenenyl-adenosine, 2'-O-methyl-2-aminoadenosine, 2'-O-methyl-2'-deoxyadenosine, 2'-O-methyl-2'-deoxycytidine, 2'-O-methyl-2'-deoxyguanosine, 2,-O-methyl-2'-deoxyuridine, 2'-O-methyl-5-methyluridine, 2'-O-methylinosine, 2'-O-methylpseudouridine, 2-thiocytidine, 2-thio-cytidine, 3-methyl-cytidine, 4-acetyl-cytidine, 4-thiouridine, 5-(carboxyhydroxymethyl)-uridine, 5,6-dihydrouridine, 5-aminoallylcytidine, 5-aminoallyl-deoxyuridine, 5-bromouridine, 5-carboxymethylaminomethyl-2-thio-uracil, 5-carboxymethylamonomethyl-uracil, 5-chloro-ara-cytosine, 5-fluoro-uridine, 5-iodouridine, 5-methoxycarbonylmethyl-uridine, 5-methoxy-uridine, 5-methyl-2-thio-uridine, 6-Azacytidine, 6-azauridine, 6-chloro-7-deaza-guanosine, 6-chloropurineriboside, 6-mercapto-guanosine, 6-methyl-mercaptopurine-riboside, 7-deaza-2'-deoxy-guanosine, 7-deazaadenosine, 7-methyl-guanosine, 8-azaadenosine, 8-bromo-adenosine, 8-bromo-guanosine, 8-mercapto-guanosine, 8-oxoguanosine, benzimidazole-riboside, beta-D-mannosyl-queosine, dihydrouridine, inosine, N1-methyladenosine, N6-([6-aminohexyl]carbamoylmethyl)-adenosine, N6-isopentenyl-adenosine, N6-methyl-adenosine, N7-methyl-xanthosine, N-uracil-5-oxyacetic acid methyl ester, puromycin, queosine, uracil-5-oxyacetic acid, uracil-5-oxyacetic acid methyl ester, wybutoxosine, xanthosine, and xylo-adenosine. In some embodiments, the chemically modified nucleic acid as described herein comprises at least one chemically modified nucleotide selected from 2-amino-6-chloropurineriboside-5'-triphosphate, 2-aminopurine-riboside-5'-triphosphate, 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl-inosine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 6-methylguanosine-5'-triphosphate, pseudouridine-5'-triphosphate, puromycin-5'-triphosphate, or xanthosine-5'-triphosphate. In some embodiments, the chemically modified nucleic acid as described herein comprises at least one chemically modified nucleotide selected from pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the artificial nucleic acid as described herein comprises at least one chemically modified nucleotide selected from 5-aza-cytidine, pseudoisocytidine, 3-methyl-cytidine, N4-acetylcytidine, 5-formyl-cytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the chemically modified nucleic acid as described herein comprises at least one chemically modified nucleotide selected from 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2, 6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, and 2-methoxy-adenine. In other embodiments, the chemically modified nucleic acid as described herein comprises at least one chemically modified nucleotide selected from inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In certain embodiments, the chemically modified nucleic acid as described herein comprises at least one chemically modified nucleotide selected from 6-aza-cytidine, 2-thio-cytidine, alpha-thio-cytidine, pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, pyrrolo-cytidine, inosine, alpha-thio-guanosine, 6-methyl-guanosine, 5-methyl-cytdine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, alpha-thio-adenosine, 8-azido-adenosine, 7-deaza-adenosine.

A modified base of a unnatural nucleic acid includes, but is not limited to, uracil-5-yl, hypoxanthin-9-yl (I), 2-amino-adenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and O-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl ($-C \equiv C-CH_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, or 2-amino-2'-deoxyadenosine.

In some cases, the at least one chemical modification can comprise chemically modifying the 5' or 3' end such as 5' cap or 3' tail of the engineered polynucleotide. In some embodiments, the engineered polynucleotide comprises a chemical modification comprising 3' nucleotides which can be stabilized against degradation, e.g., by incorporating one or more of the modified nucleotides described herein. In this embodiment, uridines can be replaced with modified uridines, e.g., 5-(2-amino) propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein. In some embodiments, deaza nucleotides, e.g., 7-deaza-adenosine, can be incorporated into the gRNA. In some embodiments, O-and N-alkylated nucleotides, e.g., N6-methyladenosine, can be incorporated into the gRNA. In some embodiments, sugar-modified ribonucleotides can be incorporated, e.g., wherein the 2' OH-group is replaced by a group selected from H,—OR,—R (wherein R can be, e.g., alkyl, cycloalkyl, aryl, aralkyl, heteroaryl or sugar), halo,—SH,—SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In some embodiments, the phosphate backbone can be modified as described herein, e.g., with a phosphothioate group. In some embodiments, the nucleotides in the overhang region of the gRNA can each independently be a modified or unmodified nucleotide including, but not limited to 2'-sugar modified, such as, 2-F 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), or any combinations thereof.

In some embodiments, all nucleotides of a targeting moiety have 2' O-methyl modifications. The 2' O-methyl modification is thought to increase the affinity of an engineered polynucleotide for its pre-mRNA targets and/or prevent degradation of an engineered polynucleotide by nucleases. In some embodiments, all nucleotides of a targeting moiety have phosphorothioate modifications.

Regulating Moiety

In some embodiments of the engineered polynucleotide described herein, the post-transcriptional regulating moiety (or the regulating moiety) (e.g., the spliceosomal moiety) is selected from a spliceosomal ribonucleoprotein complex, a spliceosomal small nuclear ribonucleic acid (snRNA), a spliceosomal protein, a functional variant thereof, or a functional fragment thereof. In some embodiments, the spliceosomal moiety comprises U1 snRNA and a spliceosomal protein. In some embodiments, the spliceosomal moiety comprises U2 snRNA and a spliceosomal protein. In some embodiments, the spliceosomal snRNA is selected from U1, U2, U4, U5, U6, U11, U12, U14atac, U6atac, and combinations thereof. In some embodiments, the spliceosomal snRNA is U1 or U2. In some embodiments, the spliceosomal protein is selected from Sm, U1-70 k, U1A, U1C, and combinations thereof. Non-limiting example of the spliceosomal moiety includes SmD1, SmD2, SmD3, SmE, SmF, SmG, U1, U2, U4, U5, U6, U11, U12, U14, or U16.

In some embodiments described herein, when associated with the engineered polynucleotide and the RNA (e.g., the mRNA, such as the pre-mRNA), the spliceosomal moiety cleaves or splices the RNA (e.g., the mRNA, such as the pre-mRNA) in the target sequence. In some embodiments, the spliceosomal moiety further facilitates modification of a cleaved RNA (e.g., a cleaved mRNA, such as a cleaved pre-mRNA).

In some embodiments, the binding of the engineered polynucleotide to the target sequence by base pairing such as Watson-Crick base pairing. The binding of the engineered polynucleotide to the recruiting moiety provided herein can be utilized to modulate expression or activity of a target gene. In some embodiments, the binding of the engineered polynucleotide to the recruiting moiety enables the recruiting moiety to splice the pre-mRNA encoding the target gene with increased specificity, thus modulating the target gene. In some embodiments, the binding of the engineered polynucleotide to the recruiting moiety enables the recruiting moiety to splice the pre-mRNA encoding the target gene with increased efficiency, thus modulating the target gene. Modulation can refer to increasing or decreasing the expression or activity of the target gene. Non-limiting example of the target gene can include microtubule associated protein tau (MAPT). In some embodiments, the expression or activity of the target gene, when the engineered polynucleotide binds to the recruiting moiety, is increased by at least 10%, 20%, 30%, 40%, 50%, 60%, 70%, 80%, 90%, 2 fold, 3 fold, 4 fold, 5 fold, 10 fold, or more compared to the expression or activity of the target gene in the absence of the engineered polynucleotide binding to the recruiting moiety. In some embodiments, the expression or activity of the target gene, when the engineered polynucleotide binds to the recruiting moiety, is decreased by at least 10%, 20%, 30%, 40%, 50%, 60%, 70%, 80%, 90%, 2 fold, 3 fold, 4 fold, 5 fold, 10 fold, or more compared to the expression or activity of the target gene in the absence of the engineered polynucleotide binding to the recruiting moiety.

In some embodiments, the modulating of the expression or activity of the target comprises correcting aberrant expression of the target gene due to splice variant. In some embodiments, the expression or activity of misfolded target gene or protein due to aberrant splice variant, when the engineered polynucleotide binds to the recruiting moiety, is decreased by at least 10%, 20%, 30%, 40%, 50%, 60%, 70%, 80%, 90%, 2 fold, 3 fold, 4 fold, 5 fold, 10 fold, or more compared to the expression or activity of misfolded target gene or protein due to aberrant splice variant in the absence of the engineered polynucleotide binding to the recruiting moiety. In some embodiments, the amount of misfolded protein aggregate due to aberrant splice variant, when the engineered polynucleotide binds to the recruiting moiety, is decreased by at least 10%, 20%, 30%, 40%, 50%, 60%, 70%, 80%, 90%, 2 fold, 3 fold, 4 fold, 5 fold, 10 fold, or more compared to the amount of misfolded protein aggregate due to aberrant splice variant in the absence of the engineered polynucleotide binding to the recruiting moiety. In some embodiments, the amount of plaques comprising the misfolded protein due to aberrant splice variant, when the engineered polynucleotide binds to the recruiting moiety, is decreased by at least 10%, 20%, 30%, 40%, 50%, 60%, 70%, 80%, 90%, 2 fold, 3 fold, 4 fold, 5 fold, 10 fold, or more compared to the amount of plaques comprising the misfolded protein due to aberrant splice variant in the absence of the engineered polynucleotide binding to the recruiting moiety.

Molecular Interaction(s)

Figure 2A:
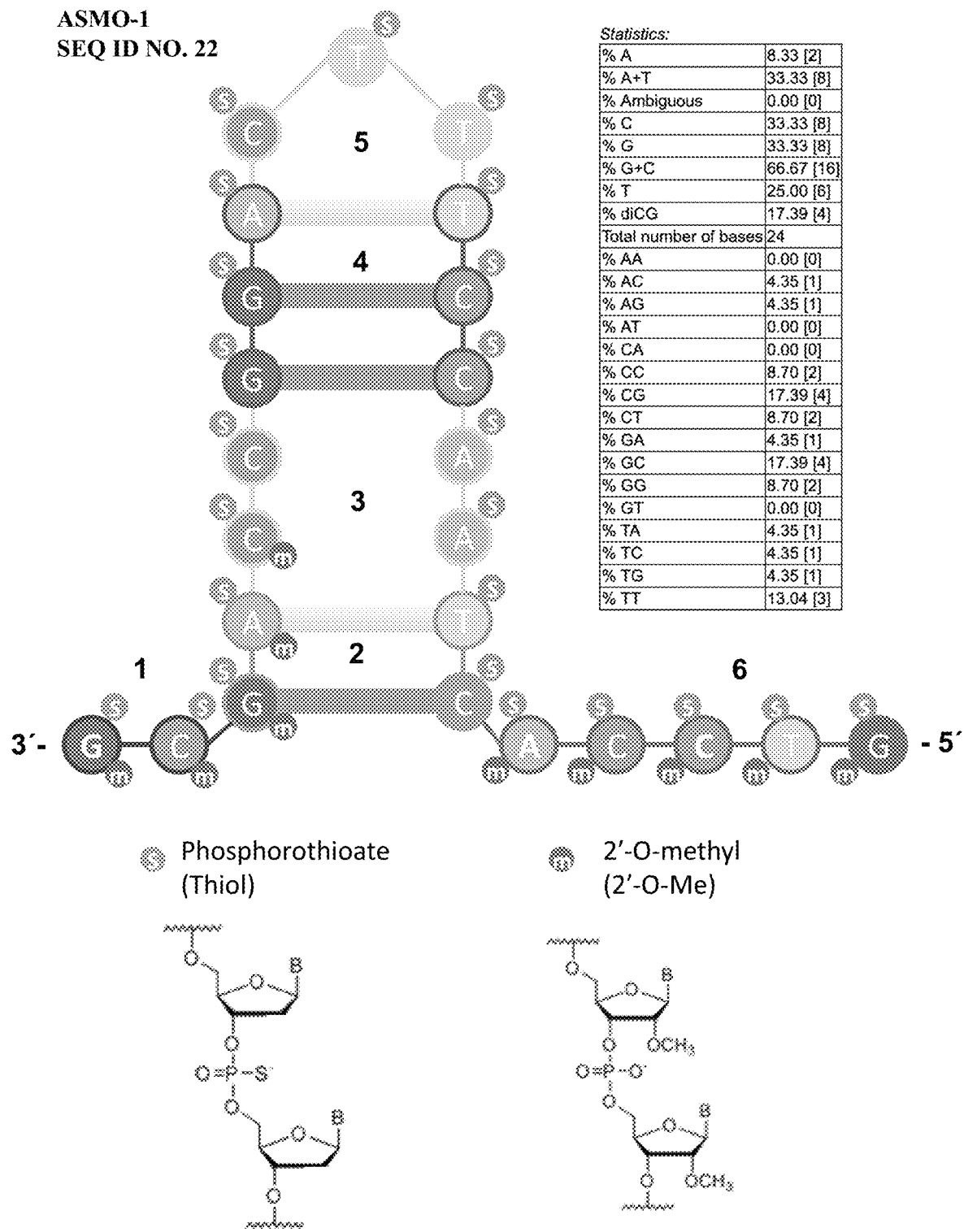
Figure 2B:
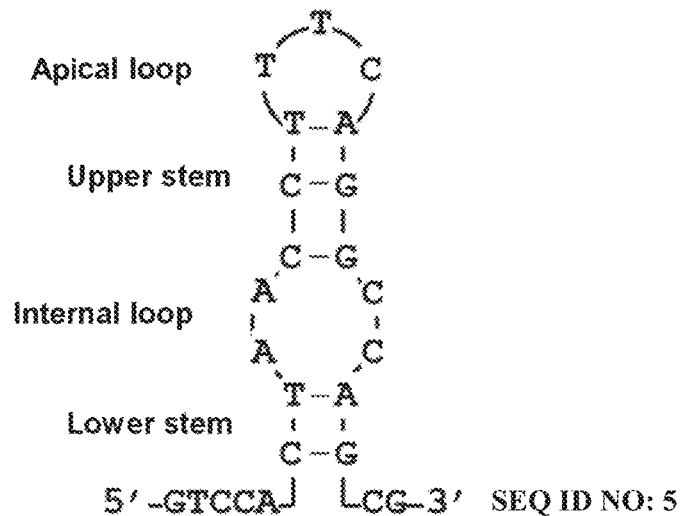
Figure 2C:
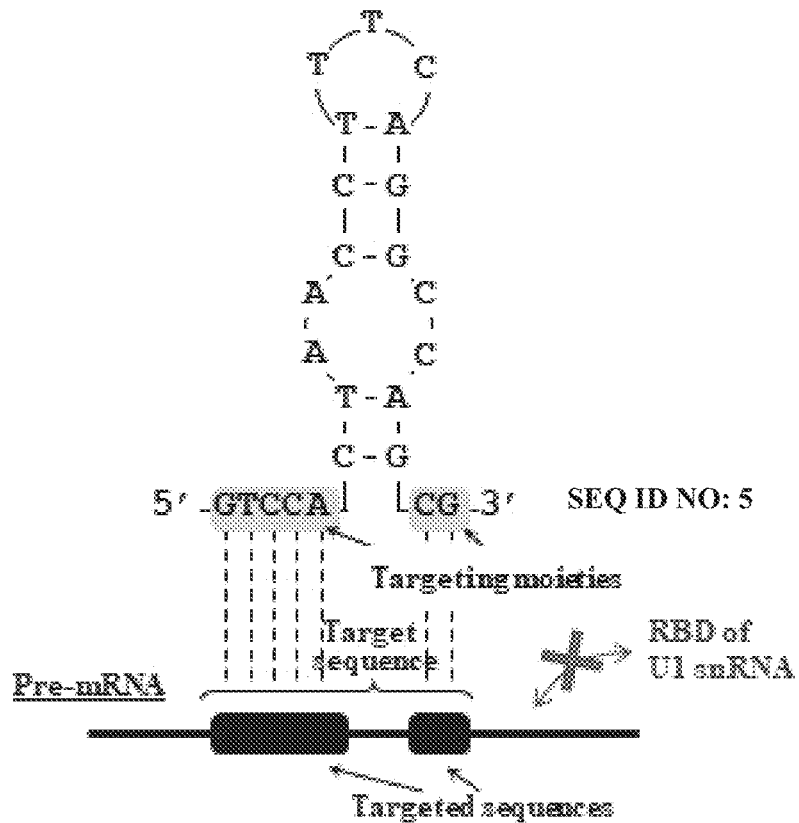
FIG. 2C illustrates interactions of the example engineered polynucleotide with a target pre-mRNA sequence.
Figure 2D:
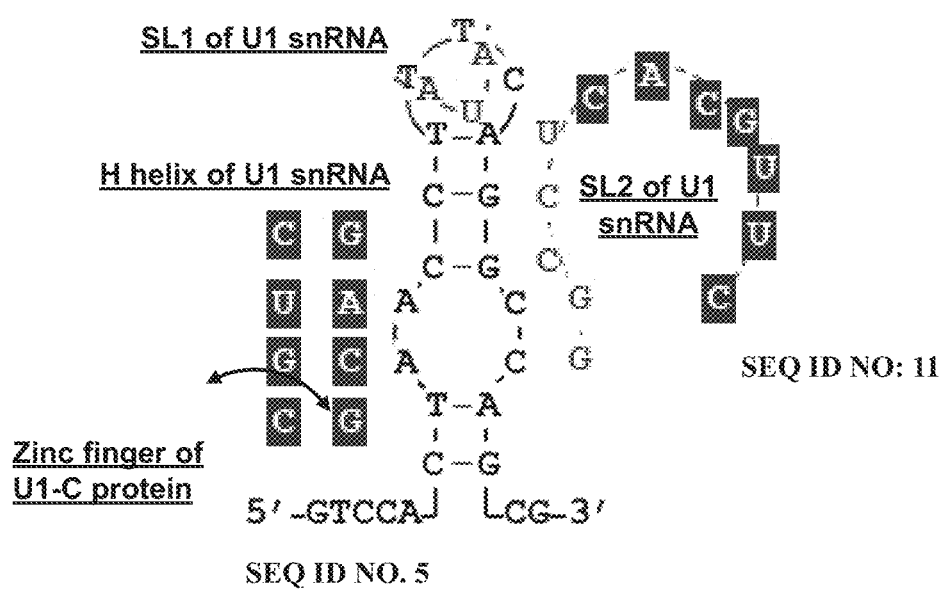
FIG. 2D illustrates interactions of the example engineered polynucleotide with various components of a U1 RNP complex. Figure discloses SEQ ID NOS 22, 5, 5, 5, and 11, respectively, in order of appearance.
Figure 7:
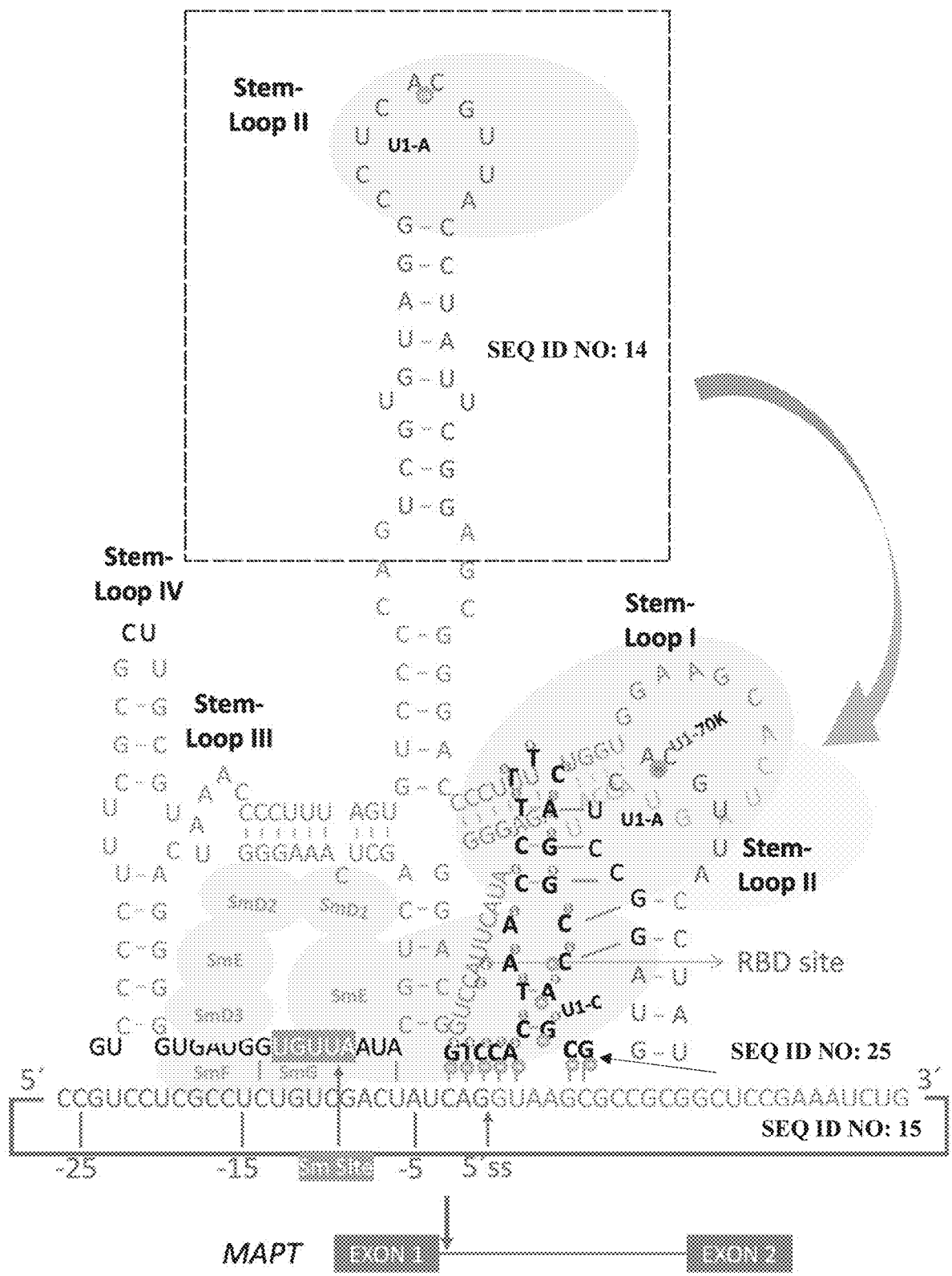
FIG. 7 illustrates a diagrammatic representation of the modulation of spliceosome machinery by an engineered polynucleotide (ASMO1) described herein. The anchoring of the targeting moieties ("Step 5'/3'") (5'-GTCCA-3' and 5'-CG-3') allows interaction with the conserved site of constitutive donor, through the silencing of the RNA binding moiety (RBD) of U1 snRNA. Stabilization of the U1 snRNP complex can be observed through the strong ionic attraction of the Zinc Finger of U1-C, induced by disulfide bridges with thiol of the ASMO1 Stem 5'/3'. The pre-mRNA/ASMO1 duplex bond is stabilized by hydrogen bonds and electrostatic interactions between U1-C and the backbone of the pre-mRNA around the seam joint, but U1-C does not make base-specific contacts with pre-mRNA. The structure demonstrates that the selection of nucleotides of 5'-splices by U1 snRNP is achieved predominantly through the interaction between Stem 5'/3' with pre-mRNA. Meanwhile, U1-C adjusts relative affinities of incompatible sites of 5'-splices and stabilizes the central core of spliceosome machinery by the interaction bridge between U1-70 KDa and the Sm ring. An electrostatic interaction and hydrogen bridges of Stem-Loop II with specific base (5'-AGGCC-3') of an upper stem (a.k.a. "Hairpin-2"; see FIG. 2B) (3'-GGA-5'/5'-CCT-3') and Internal loop: (3'-mCC-5'/5'-AA-3'); can be observed, associated with modulation of the polyadenylation signal and acetylation by U1-A. It is noted that the anchoring moiety of U1-A in Stem-Loop II (5'-CAACGUUA-3') is not silenced by the upper stem, inducing the modulation of the levels of genic expression and acetylation. In addition, the presence of 2'-OME groups induces a change in the molecular dynamics of the medium facilitating the conformational alteration of U1-snRNA and approximation of Stem-loop II to ASMO1, where the ASMO1 targeting or recruiting moiety are distinct from the U1-A protein decreasing the likelihood of premature interruption of the reading frame by deregulation of the polyadenylation signal. Figure discloses SEQ ID NOS 14, 25, 23 and 18, respectively, in order of appearance.
Figure 8:
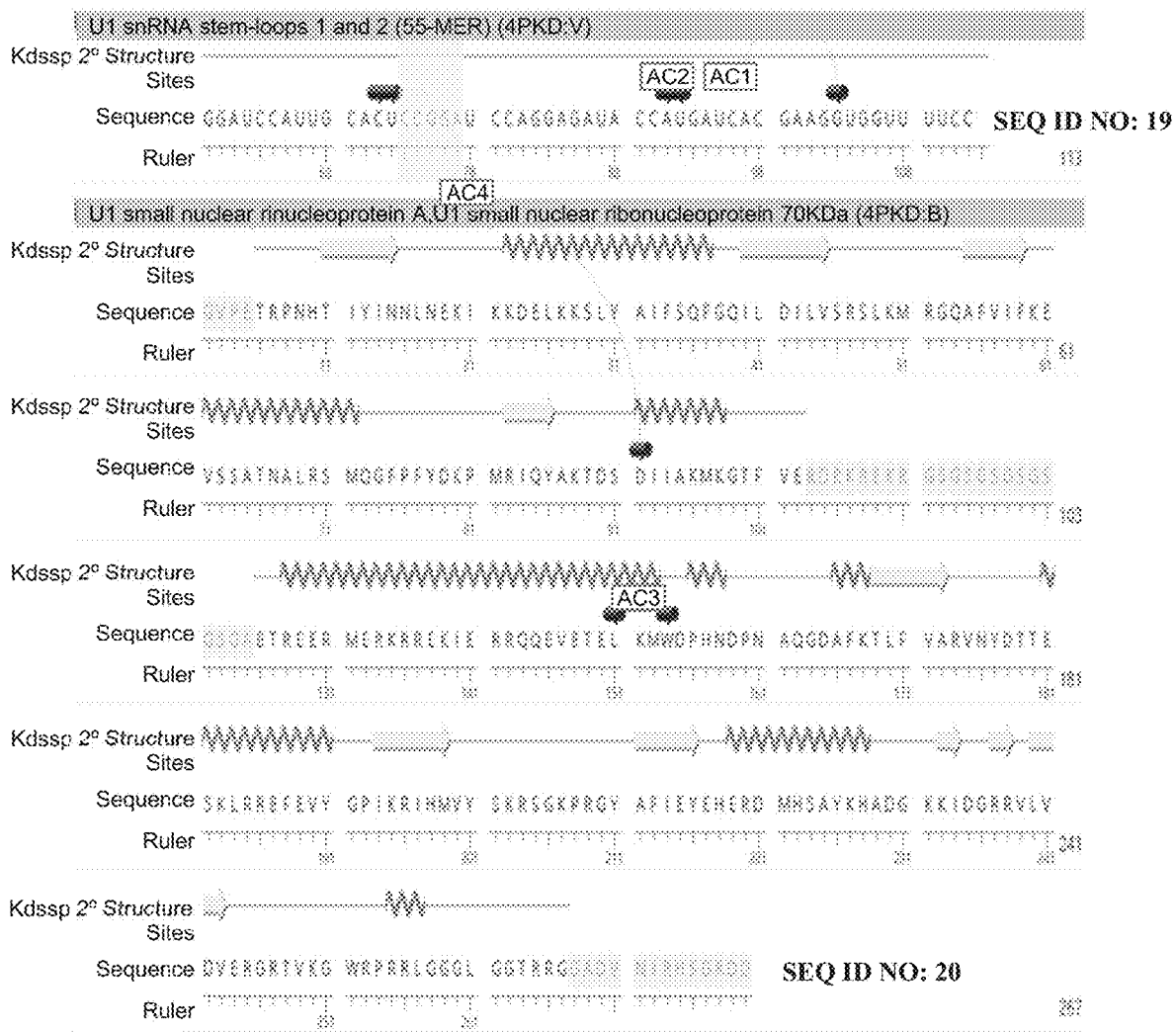
FIG. 8 illustrates U1-70 k in complex with U1 snRNA stem-loops and U1-A RRM in complex with stem-loop 2, stabilized through the U1-C zinc finger. An electrostatic interaction and hydrogen bridges of Stem-Loop II with specific base (3'-CCGGA-5') of an upper stem (3'-GGA-5'/5'-CCT-3') and Internal loop: (3'-mCC-5'/5'-AA-3'); can be observed, associated with modulation of the polyadenylation signal and acetylation by U1-A. It is noted that the anchoring moiety of U1-A in Stem-Loop II (5'-CAACGUUA-3') is not silenced by the upper stem, inducing the modulation of the levels of genic expression and acetylation. In addition, the presence of 2'-OME groups induces a change in the molecular dynamics of the medium facilitating the conformational alteration of U1-snRNA and approximation of Stem-loop II to the engineered polynucleotide described herein (ASMO1). Figure discloses SEQ ID NOS 19-20, respectively, in order of appearance.
Figure 9A:
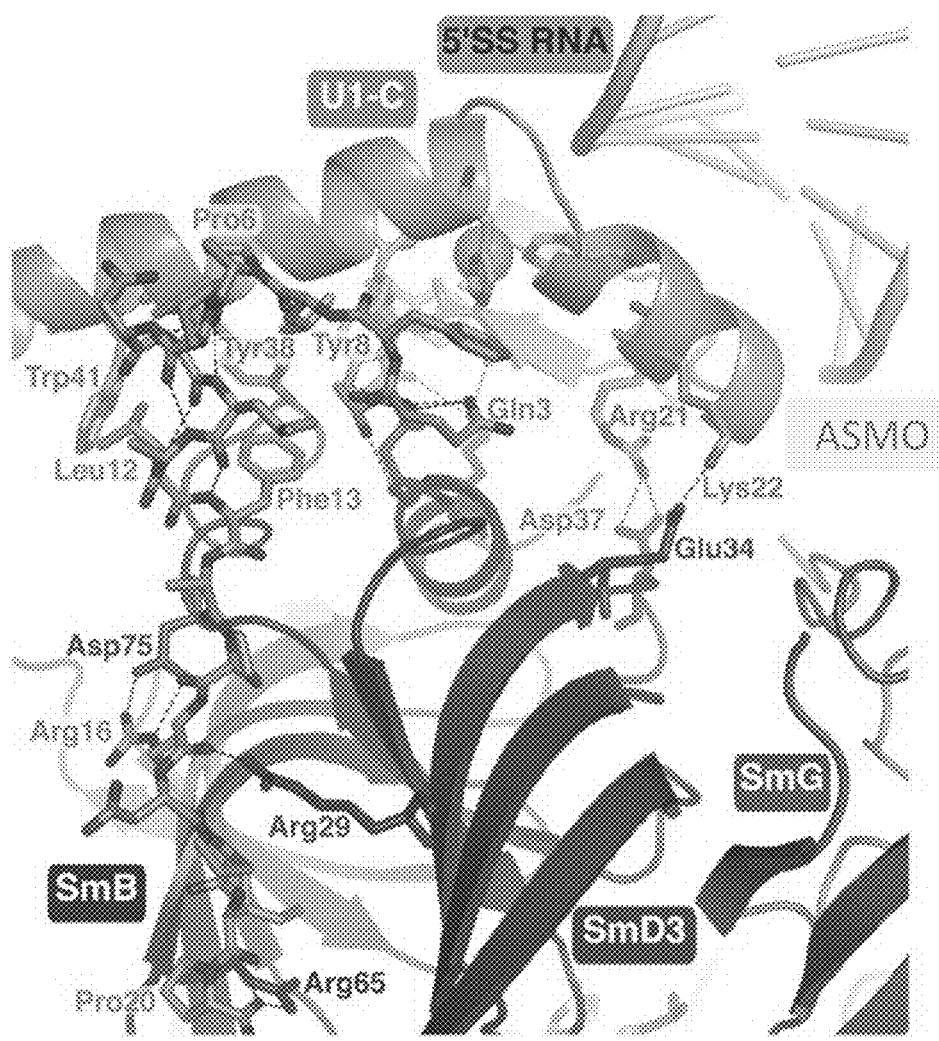
FIG. 9A illustrates U1-C sitting on SmD3 and its binding can be stabilized by the N-terminus of U1-70 k.
Figure 9B:
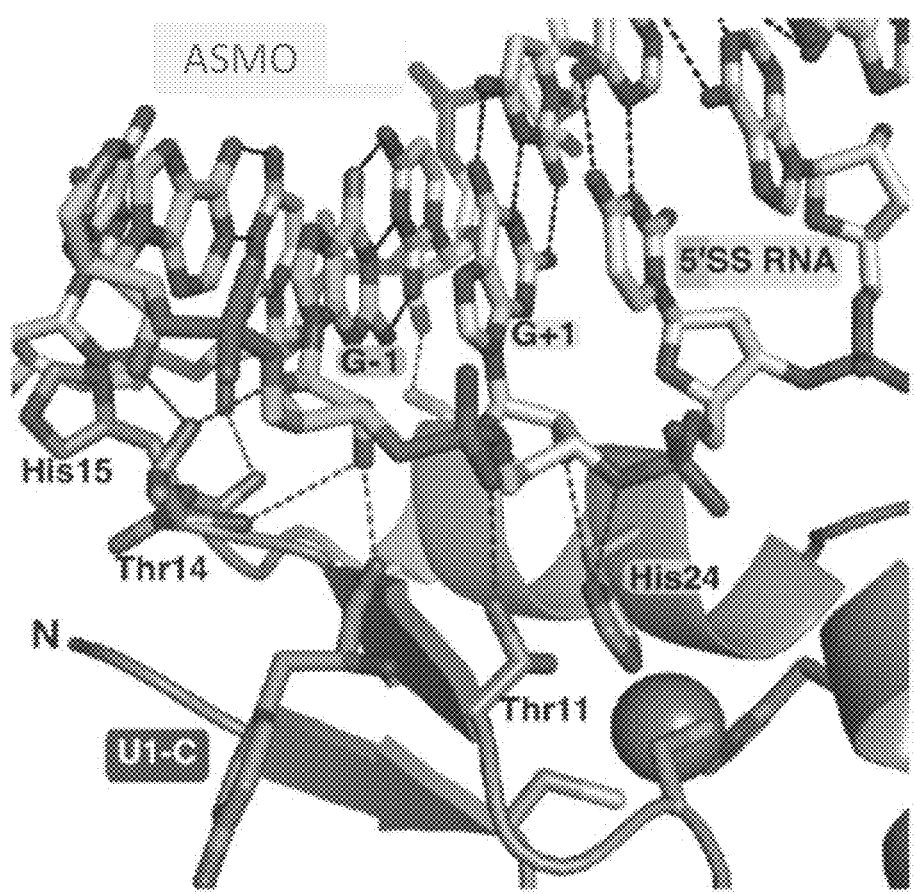
FIG. 9B illustrates U1-C forming hydrogen bonds with the sugar-phosphate backbone atoms but making no contact with RNA bases. On the 5'SS strand, nucleotides are colored teal for exonic and fawn for intronic sequence.
Figure 9C:
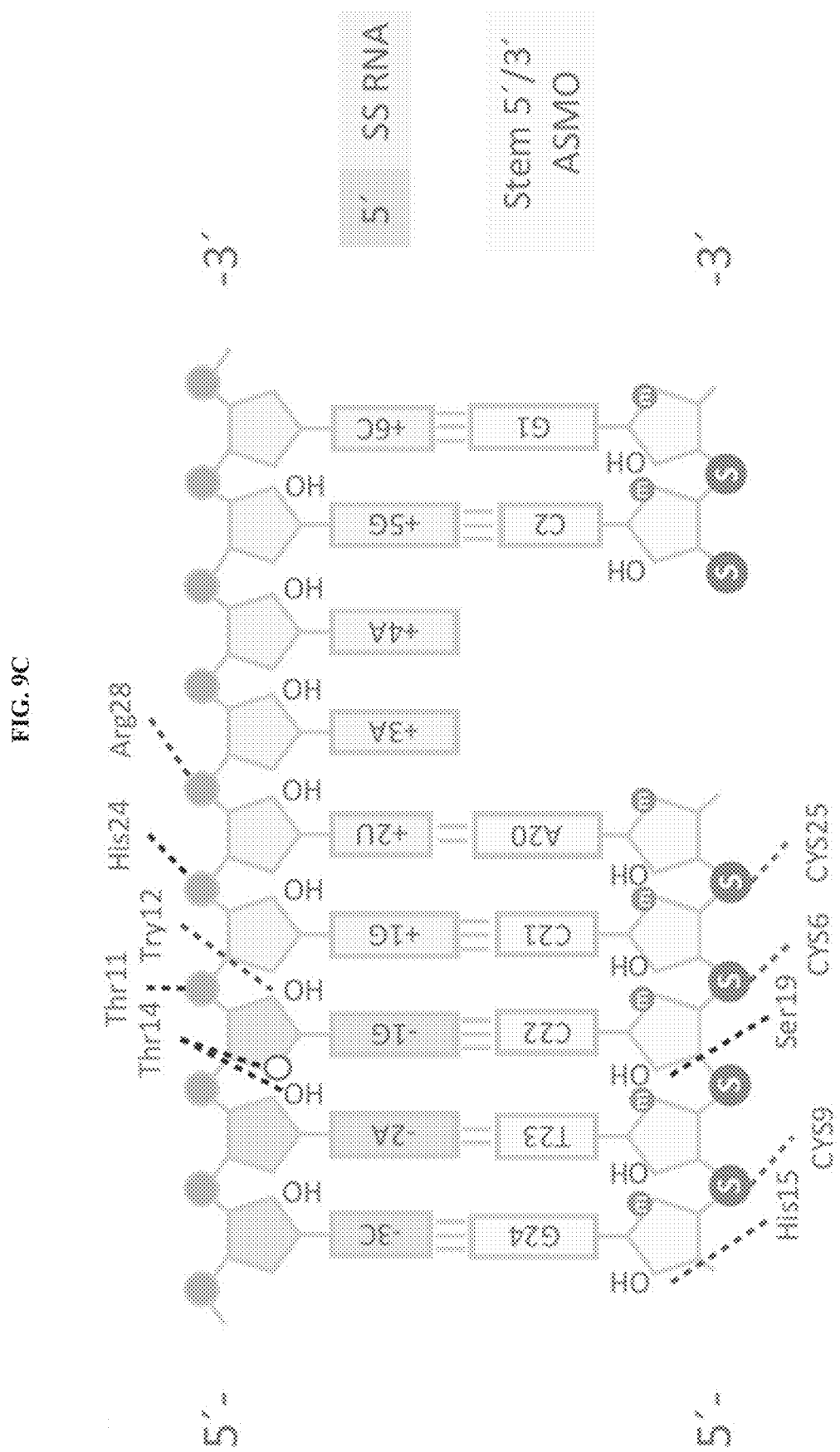
FIG. 9C illustrates schematic representation of the 5'-splice site recognition. Red dotted lines: hydrogen bonds made by amino acid side chains of U1-C Zinc Finger. Blue dotted lines: hydrogen bonds made by main chain atoms of U1-C Zinc Finger. Green dotted lines: disulfide bonds made by amino acid side chains of the U1-C zinc finger. Orange dotted lines: disulfide bonds made by atoms in the main chain of the U1-C zinc finger. The 5'SS nucleotides are encoded by nuclei as in FIG. 9B.
Figure 11:
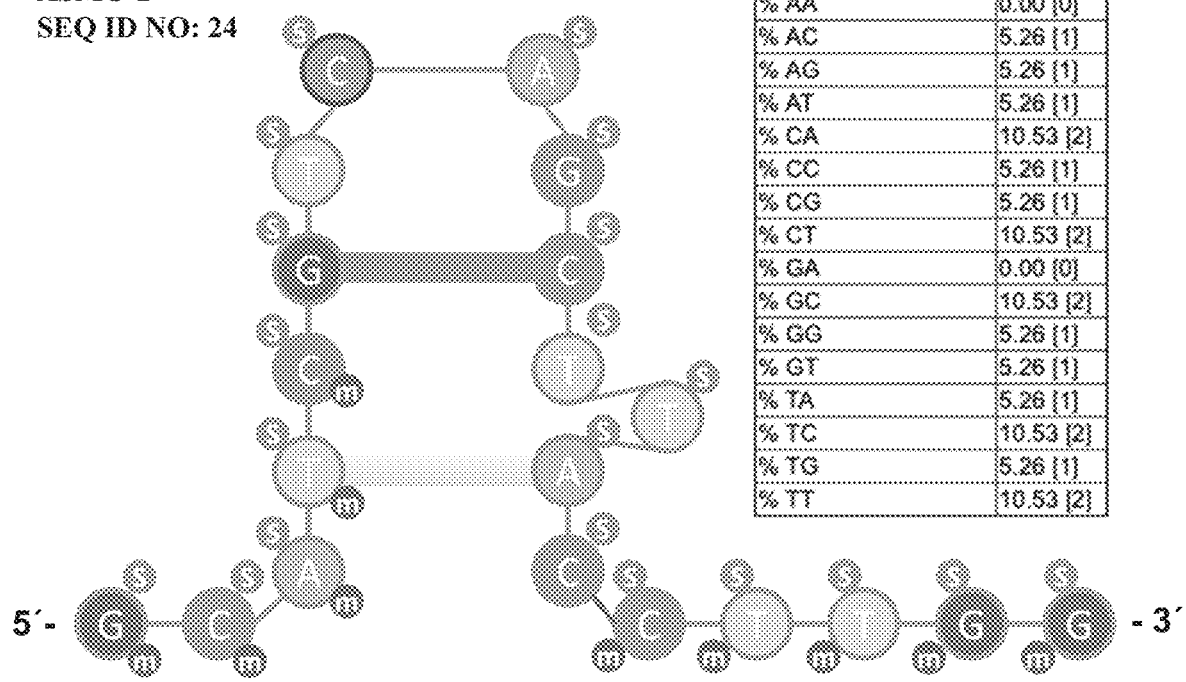
FIG. 11 illustrates an example engineered polynucleotide (ASMO2) comprising a modified antisense modulated oligonucleotide with phosphorothioate-type internucleotide bonds and 2'-methyl (2' O-ME) substitutions for sugar molecules. The ASMO2 engineered polynucleotide can be complementary and bind to U1 snRNA for modulating the expression and activity of the target sequence encoding the target gene. Figure discloses SEQ ID NO: 24.
Figure 11:
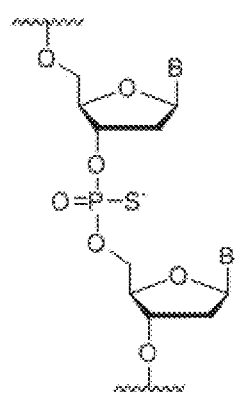
Figure 11:
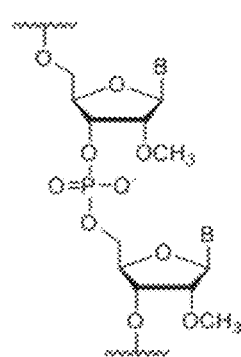

In some embodiments described herein, a targeting moiety comprises free 5' and 3' ends that interact with a conserved site of a constitutive splice donor. This interaction can silence the U1 snRNA RNA-binding domain. In some embodiments, the targeting moiety comprises 2' modified nucleotides that increase affinity to pre-mRNA targets.

In some embodiments, binding of a targeting moiety to a pre-mRNA is stabilized by hydrogen bonds and electrostatic interactions between U1-C and the pre-mRNA backbone around a splice junction region for the pre-mRNA. In such embodiments, U1-C may not make specific base contacts with the pre-mRNA. 2' nucleotide modifications can favor hydrogen bonding between a targeting moiety and U1-C. Accordingly binding of a targeting moiety (free 5' and 3' ends) to a pre-mRNA duplex enables recognition and stabilization of the targeting interaction by U1-C U1-C can stabilize the spliceosome central nucleus. U1-C enhances the affinities of incompatible 5'-splices and stabilizes the central core of the spliceosome machinery through an interaction bridge between U1-70 KD and the Sm ring.

In some embodiments, a targeting moiety can interact with the zinc finger of U1-C. phosphorothioate internucleotide linkages in the targeting moiety favor interaction of a targeting moiety and the zinc finger.

In some embodiments, a recruiting moiety forms hydrogen bridges to stem-loop II of U1-A. Such interactions can modulate polyadenylation and acetylation signaling by U1-A because stem-loop II of U1-A may not be silenced by the recruiting moiety.

In some embodiments described herein, the engineered polynucleotide does not comprise any intramolecular disulfide bond.

In some embodiments of the engineered polynucleotide described herein, when associated with the engineered polynucleotide and the spliceosomal moiety, the RNA (e.g., the mRNA, such as the pre-mRNA) exhibits substantially no base pairing with an RNA binding domain (RBD) of U1 snRNA.

In some embodiments of the engineered polynucleotide described herein, when associated with the engineered polynucleotide and the spliceosomal moiety, the RNA (e.g., the mRNA, such as the pre-mRNA) exhibits substantially no base-specific interaction with U1-C protein.

In some embodiments of the engineered polynucleotide described herein, the engineered polynucleotide is configured to specifically interact with zinc-finger of U1-C protein, e.g., comprising an amino acid sequence of: YYCDYCDTYLTHDSPSVRKTHCTGRKHRDNVKF (SEQ ID NO: 9). In some embodiments, a 5'-targeting moiety of the engineered polynucleotide is configured to specifically interact with zinc-finger of U1-C protein. In some embodiments, (e.g., the 5'-targeting moiety of) the engineered polynucleotide is configured to covalently interact (e.g., via disulfide bonding) with zinc-finger of U1-C protein. In some embodiments, (e.g., the 5'-targeting moiety of) the engineered polynucleotide is configured to non-covalently interact (e.g., via hydrogen bonding) with zinc-finger of U1-C protein.

In some embodiments, the engineered polynucleotide (e.g., ASMO1 or ASMO2 descried herein) comprises a nucleotide sequence complementary to U1 snRNA. In some embodiments of the engineered polynucleotide described herein, the engineered polynucleotide comprises a nucleotide sequence complementary to a partial sequence of Stem-Loop II (SL2) of U1 snRNA. In some embodiments, a side of a stem-loop structure of the engineered polynucleotide comprises a nucleotide sequence complementary to a partial sequence of Stem-Loop II (SL2) of U1 snRNA. In some embodiments, the partial sequence comprises the sequence corresponding to 5'-GGCCU-3' of SL2 of U1 snRNA. In some embodiments, the partial sequence does not comprise the sequence corresponding to 5'-CACGUUA-3' of SL2 of U1 snRNA.

In some embodiments of the engineered polynucleotide described herein, the engineered polynucleotide exhibits substantially no base pairing with an anchoring sequence of SL2 of U1 snRNA. In some embodiments, the anchoring sequence comprises the sequence corresponding to 5'-CACGUUA-3'. In some embodiments, an internal loop of the engineered polynucleotide exhibits substantially no base pairing with the anchoring sequence of the SL2 of U1 snRNA. In some embodiments, a lower stem of the engineered polynucleotide exhibits substantially no base pairing with the anchoring sequence of the SL2 of U1 snRNA.

In some embodiments of the engineered polynucleotide described herein, the engineered polynucleotide exhibits substantially no base pairing with H helix of U1 snRNA.

In some embodiments, the engineered polynucleotide does not comprise any intramolecular disulfide bond. In some embodiments, the engineered polynucleotide, when recruiting the spliceosomal moiety described to the target sequence such as target pre-mRNA, the engineered polynucleotide does not exhibit base pairing with an RNA binding domain (RBD) of the spliceosomal moiety such as U1 snRNA. FIG. 4 illustrates such lack of base pairing between the engineered polynucleotide and the RBD of the spliceosomal moiety, where the RBD site of U1 snRNA has the following sequence: 3'-GUCCAUUCAUA-5' (SEQ ID NO: 10) and forms base pairing with the target sequence. In some instances, when the engineered polynucleotide and the spliceosomal moiety are bound, the engineered polynucleotide exhibits substantially no base-specific interaction with U1-C spliceosomal moiety. In some embodiments, the engineered polynucleotide is configured to specifically interact with zinc-finger of U1-C protein or U1-1 spliceosomal moiety. FIG. 10C illustrates a representative sequence of U1-C snRNP containing 145 amino acids, with the highlighted 36 amino acids (YYCDYCDTYLTHDSPSVRKTHCTGRKHRDNVKF (SEQ ID NO: 9)) comprising the zinc-finger domain.

In some embodiments, the engineered polynucleotide is configured to covalently interact (e.g., via disulfide bonding) with zinc-finger of U1-C protein or U1-1 spliceosomal moiety. In some embodiments, the engineered polynucleotide is configured to non-covalently interact (e.g., via hydrogen bonding) with zinc-finger of U1-C protein or U1-1 spliceosomal moiety. In some embodiments, the engineered polynucleotide (e.g., ASMO1 or ASMO2 descried herein) comprises a nucleotide sequence complementary to U1 snRNA. In some embodiments, the engineered polynucleotide comprises a nucleotide sequence complementary to a partial sequence of Stem-Loop II (SL2) of U1 snRNA. In some embodiments, a side of a stem-loop secondary structure of the engineered polynucleotide comprises a nucleotide sequence complementary to a partial sequence of Stem-Loop II (SL2) of U1 snRNA. In some embodiments, the partial sequence comprises the sequence corresponding to 5'-GGCCU-3' of SL2 of U1 snRNA. In some embodiments, the partial sequence does not comprise the sequence corresponding to 5'-CACGUUA-3' of SL2 of U1 snRNA. In some embodiments, the engineered polynucleotide exhibits substantially no base pairing with an anchoring sequence of SL2 of U1 snRNA. In some cases, the internal loop of said engineered polynucleotide exhibits substantially no base pairing with said anchoring sequence of said SL2 of U1 snRNA. In some aspects, the lower stem of said engineered polynucleotide exhibits substantially no base pairing with said anchoring sequence of said SL2 of U1 snRNA. In some aspects, the anchoring sequence comprises the sequence corresponding to 5'-CACGUUA-3'. In some cases, the engineered polynucleotide exhibits substantially no base pairing with H helix of U1 snRNA, where the engineered polynucleotide does not comprise any intramolecular disulfide bond. For example, FIG. 2A illustrates the lack of intramolecular disulfide bond due to the presence of chemical modification with phosphorothioate-type internucleotide bonds. Stabilization of the U1 snRNP complex can be observed through the strong ionic attraction of the Zinc Finger of U1-C, induced by disulfide bridges with thiol of the engineered polynucleotide (ASMO) targeting moieties at 5'- or/and 3'-end. The pre-mRNA/engineered polynucleotide (ASMO) duplex bond can be stabilized by hydrogen bonds and electrostatic interactions between U1-C and the backbone of the pre-mRNA around the seam joint, but U1-C does not make base-specific contacts with pre-mRNA. The structure demonstrates that the selection of nucleotides of 5'-splices by U1 snRNP is achieved predominantly through the interaction between Stem 5'/3' with pre-mRNA. Meanwhile, U1-C adjusts relative affinities of incompatible sites of 5'-splices and stabilizes the central core of spliceosome machinery by the interaction bridge between U1-70 KDa and the Sm ring (see FIGS. 7-9). Of the U1 snRNP specific proteins, U1-70 k and U1-C have important roles in aiding recognition of the pre-mRNA transcript. U1-70 k has an N-terminus that while highly conserved is predicted to be unstructured (residues –2-60), an RNA binding domain (or RBD) that mediates its interaction with a stem-loop of U1 snRNA (residues 92-202), and a C-terminus rich in repeats of arginine and serine residues (an RS 'domain') as well as R-(D/E) residues. Although this C-terminal domain is not conserved the RS 'domain' is important for interaction with non-snRNP splicing factors such as ASF/SF2. Serines in this region are subjected to post-translational modification (phosphorylation) and are important to splicing activity. U1-C consists of an N-terminal zinc-finger domain and a C-terminal region rich in repeats of RG residues. Arginines in this region of U1-C are subjected to post-translational modification (methylation). In contrast to U1-70 k, U1-C does not bind to free U1 snRNA but requires the prior binding of the Sm proteins and U1-70 k. Mutations in the zinc-finger region of U1-C have a significant effect on recognition of the 5' splice site by the U1 snRNP, indicating that this protein has a direct role to play in this activity. The assembly and function of U1 snRNP has been greatly enhanced initially by cryo electron microscopy studies and more recently by elucidation of its three-dimensional structure by X-ray crystallography. Previously, crystal structures of four of seven Sm proteins led to the modeling of the remaining three (Sm-F, Sm-E and Sm-G) and the proposal that together they would interact to form a seven-membered ring. The crystal structure of a completely recombinant human U1 snRNP reveals that Sm proteins do form a heptameric ring, composed of a single copy of each Sm protein, and passing through its center is the Sm site of U1 snRNA. In the crystal structure, U1-C is in a position to recognize the duplex formed when the 5' end of U1 snRNA base-pairs to the 5' splice site. The finding that the N-terminus of U1-70 k extends 180 A from the RBD and wraps around one face of the Sm ring, crossing Sm-D2 and Sm-D3/B, could therefore ensure the correct structure and positioning of U1-C for interaction with the U1 snRNA:5' splice site duplex (FIG. 9).

Figure 3A:
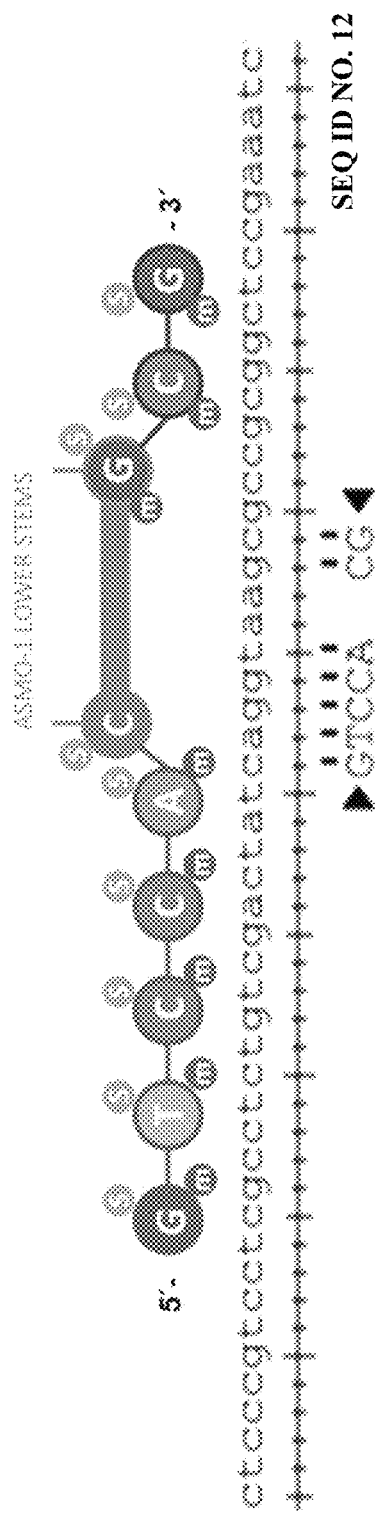
Figure 3B:
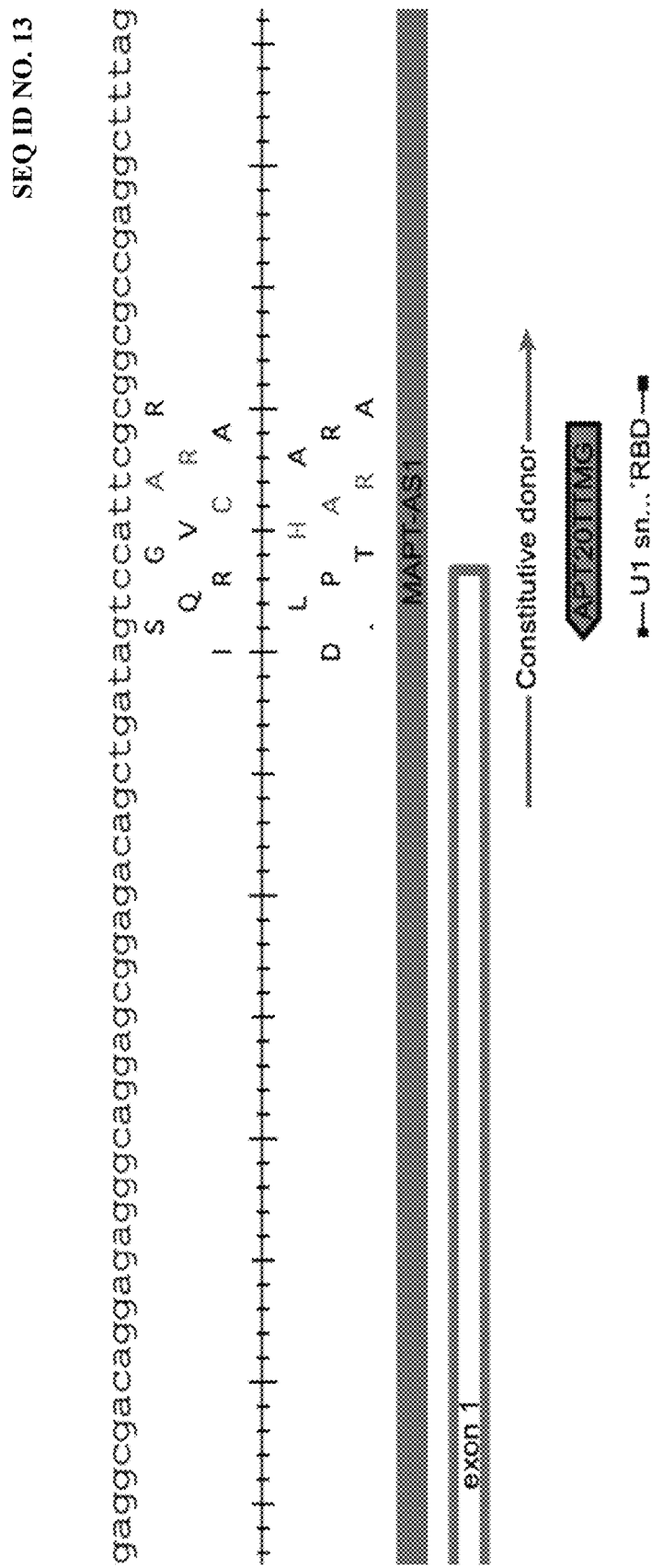
Figure 4:
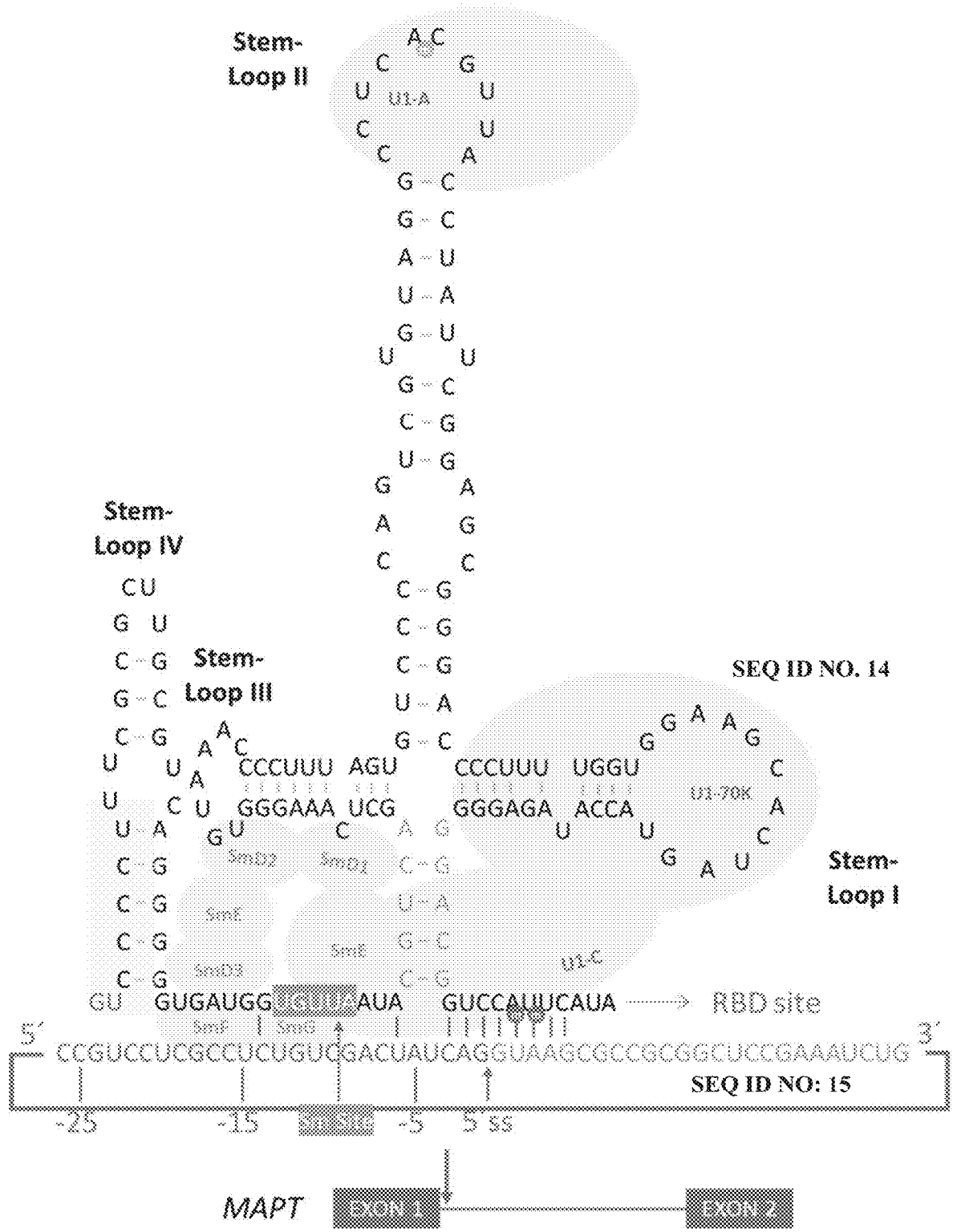
FIG. 4 illustrates a diagram of a human U1 snRNP. U1 snRNP is composed of one U1 snRNA, seven common Sm proteins and three U1 snRNP-specific proteins (U1-70K, U1A and U1C). Secondary structure of U1 snRNA consists of four stem-loops (SL) and an H helix highlighted. Nucleotides forming H helix are shown. In addition, U1 snRNA sequences relevant to RNA:protein or RNA:5'ss interactions are given as well. The loop portion of SL1 is drawn according to crystal structure. It is closed by a trans WC/Hoogsteen base pair formed between A29 and A36. Protein components of U1 snRNP, their sizes and their approximate locations are shown as well. The Sm ring formed by the Sm proteins shown as green circles bind to the Sm site, which is boxed. U1-70K shown in red recognizes SL1. U1A shown in yellow binds SL2. U1C shown in blue is recruited to U1 snRNP through protein:protein interactions with U1-70 K and Sm proteins. Note signifies interactions between U1C and Sm ring. Figure discloses SEQ ID NOS 14-15, respectively, in order of appearance.
Figure 5C:
FIG. 5C. U1 small nuclear ribonucleoprotein A and 70 kDa.
Figure 5B:
FIG. 5B. U1 snRNA stem-loops 1 and 2 (55-MER).
Figure 5A:
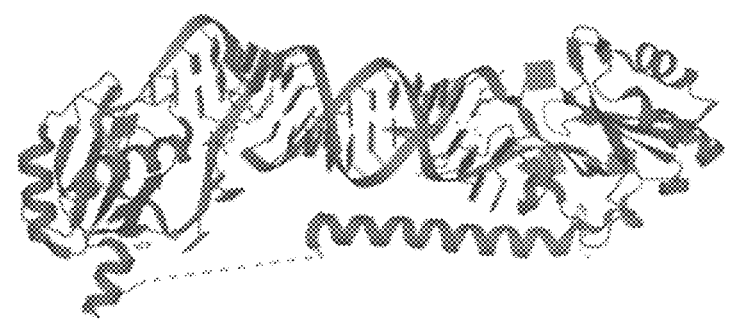
FIG. 5A. U1-70 k in complex with U1 snRNA stem-loops and U1-A RRM in complex with stem-loop 2.
Figure 6:
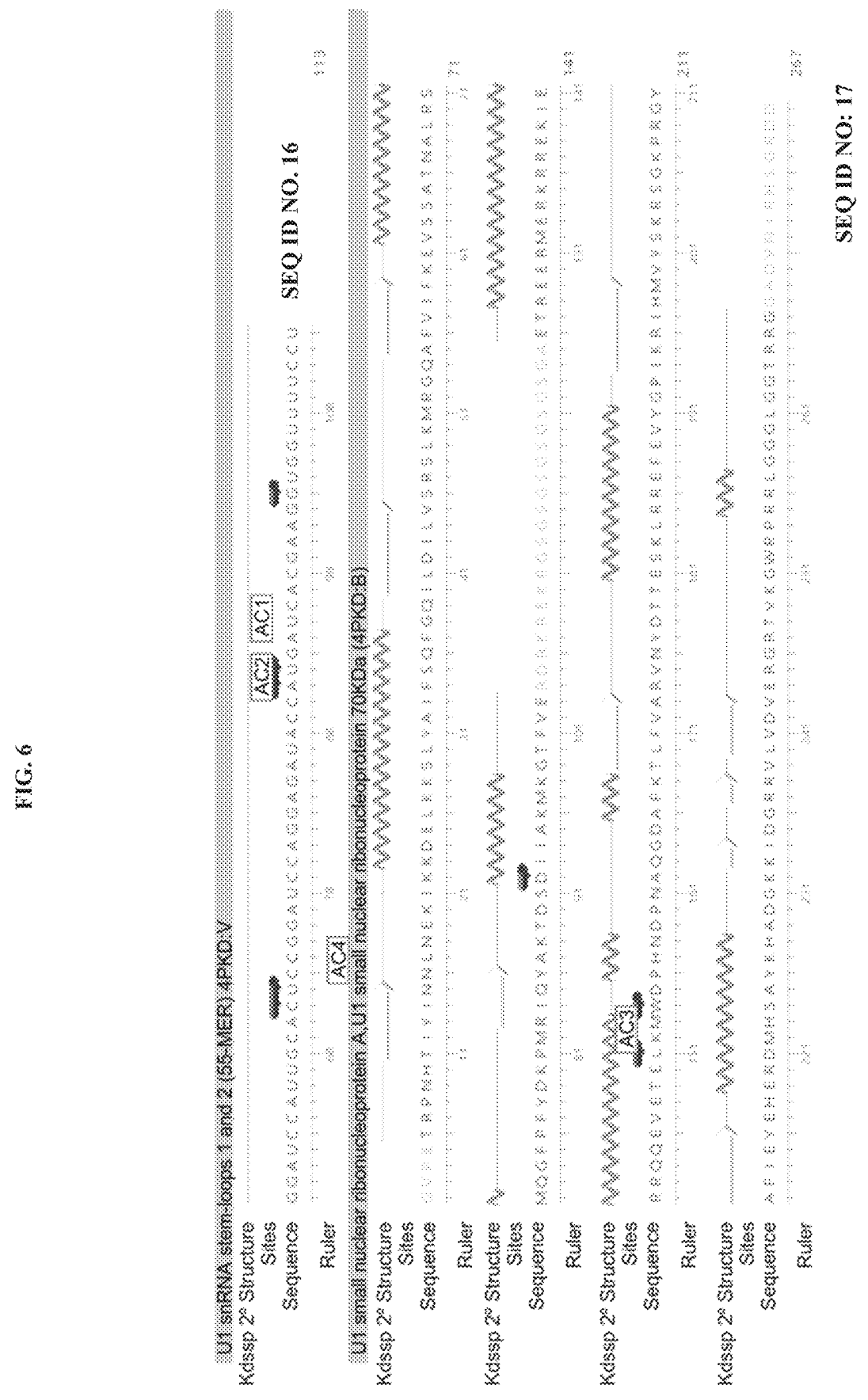

In some embodiments, the engineered polynucleotide, when associated with the spliceosomal moiety described herein, the pre-mRNA exhibits substantially no base pairing with an RNA binding domain (RBD) of U1 snRNA. In some cases, the engineered polynucleotide, when associated with the spliceosomal moiety, the pre-mRNA exhibits substantially no base-specific interaction with U1-C protein. FIG. 4 illustrates that in the absence of the engineered polynucleotide, the RBD of the U1 snRNA binds in the conserved regions of constitutive donor. Meanwhile, in the presence of the engineered polynucleotide the stem 5'/3' blocked the RBD interaction of the U1 snRNA with the pre-mRNA (FIG. 3 and FIG. 6).

In some embodiments, the engineered polynucleotide is configured to specifically interact with zinc-finger of U1-C protein. In some embodiments, a 5'-targeting moiety of said engineered polynucleotide is configured to specifically interact with zinc-finger of U1-C protein. In some embodiments, the engineered polynucleotide is configured to covalently interact (e.g., via disulfide bonding) with zinc-finger of U1-C protein. In some embodiments, the engineered polynucleotide is configured to non-covalently interact (e.g., via hydrogen bonding) with zinc-finger of U1-C protein. The formation of the pre-mRNA/engineered polynucleotide (ASMO) duplex that interacts with amino acid residues from the U1-C zinc finger stabilizes the 5; region (FIG. 9). Then, favorable molecular dynamics for formation by disulfide bonds formed by atoms in the main and side chain of the U1-C zinc finger with Stem 5' of the engineered polynucleotide can be observed. A strong ionic bond can also form as ASMO presents interaction with all the cysteines present in the U1-C zinc finger (FIG. 9 and FIG. 10). Additional example interaction between U1-C and pre-mRNA in the presence or in the absence of the engineered polynucleotide described herein is shown in Table 5.

TABLE 5

Example interaction between U1-C and pre-mRNA mediated by the presence of the engineered polynucleotide

| Domain | In presence of engineered polynucleotide | in absence of engineered polynucleotide |
| --- | --- | --- |
| Constitutive Donor 5' | The binding of the 5'/3' Stem allows the interaction with the conserved site of the constitutive donor, by silencing the U1 snRNA RNA-binding domain (RBD) | The presence of mutations in the RBD domain of U1-snRNA can induce a crypto splice or lack of recognition of the 5' region |

TABLE 5-continued

Example interaction between U1-C and pre-mRNA mediated by the presence of the engineered polynucleotide

| Domain | In presence of engineered polynucleotide | in absence of engineered polynucleotide |
|---|---|---|
| Duplex recognition 5' by U1-C | The pre-mRNA/engineered polynucleotide duplex bond is stabilized by hydrogen bonds and electrostatic interactions between U1-C and the pre-mRNA backbone around the junction region, but U1-C does not make specific base contacts with pre-mRNA. It is important to note that the 2'-OME group favors the interaction of hydrogen bonds with U1-C | Unfavorable molecular dynamics due to the low ionic attraction of the U1-C Zinc finger. It may induce a crypto splice or instability in the formation of the U1 complex in the 5' region |
| Stabilization of the 5'duplex by U1-C | The pre-mRNA/engineered polynucleotide duplex bond is stabilized by hydrogen bonds and electrostatic interactions between U1-C and the pre-mRNA backbone around the junction region, but U1-C does not make specific base contacts with pre-mRNA The 2'-OME group favors the interaction of hydrogen bonds with U1-C | Unfavorable molecular dynamics due to the low ionic attraction of the U1-C Zinc finger. It may induce a crypto splice or instability in the formation of the U1 complex in the 5' region |
| Stabilization of the spliceosome central nucleus | U1-C adjusts high-precision relative affinities of incompatible 5'-splices and stabilizes the central core of spliceosome machinery through the interaction bridge between U1-70KDa and the Sm ring | U1-C sits on SmD3 and its binding is stabilized by the N-terminus of U1-70k |
| Stem-loop | Hydrogen bridges of Stem-Loop II with specific Hairpin-2 (a.k.a., upper stem, see FIG. 2B) base and internal loop, associated with the modulation of the polyadenylation and acetylation signal by U1-A. It is noted that the anchoring domain of U1-A in Stem-Loop II, is not silenced by Hairpin-2, inducing the modulation of levels of gene | SNRPA binds stem loop II of U1 snRNA. In a snRNP-free form (SF-A) may be involved in coupled pre-mRNA splicing and polyadenylation process. May bind preferentially to the 5'-UGCAC-3' motif on RNAs. The loss of U1-A self-regulation can induce premature poly (A) signal, |
| Domain | In presence of engineered polynucleotide expression and acetylation. The presence of 2'-OME groups induces a change in the molecular dynamics of the medium facilitating the conformational alteration of U1-snRNA and approximation of Stem-loop II to engineered polynucleotide. | In absence of engineered polynucleotide dysregulation of gene expression and inadequate acetylation. |

In some embodiments, the engineered polynucleotide (e.g., ASMO1 or ASMO2 descried herein) comprises a nucleotide sequence complementary to U1 snRNA. In some aspects, the engineered polynucleotide comprises a nucleotide sequence complementary to a partial sequence of Stem-Loop II (SL2) of U1 snRNA. In other aspects, described herein is a side of a stem-loop structure of said engineered polynucleotide comprises a nucleotide sequence complementary to a partial sequence of Stem-Loop II (SL2) of U1 snRNA. In some instances, the partial sequence comprises the sequence corresponding to 5'-GGCCU-3' of SL2 of U1 snRNA, where the partial sequence does not comprise the sequence corresponding to 5'-CACGUUA-3' of SL2 of U1 snRNA and where the engineered polynucleotide exhibits substantially no base pairing with an anchoring sequence of SL2 of U1 snRNA. In some aspects, the engineered polynucleotide comprises an internal loop of said engineered polynucleotide exhibits substantially no base pairing with said anchoring sequence of said SL2 of U1 snRNA. In some embodiments, the engineered polynucleotide comprises a lower stem of said engineered polynucleotide exhibiting substantially no base pairing with said anchoring sequence of said SL2 of U1 snRNA. In some embodiments, the anchoring sequence comprises the sequence corresponding to 5'-CACGUUA-3', where then engineered polynucleotide exhibits substantially no base pairing with H helix of U1 snRNA.

Set(s) of Engineered Polynucleotides

Described herein, in some embodiments, include a set of engineered polynucleotides each independently described herein. For example, the polynucleotides of the set may independently comprise: (i) one or more targeting moiety (such as described herein) configured to bind a ribonucleic acid (RNA) (such as described herein) (e.g., a messenger ribonucleic acid (mRNA), such as a pre-messenger ribonucleic acid (pre-mRNA)) at a target sequence (such as described herein), and (ii) a recruiting moiety (such as described herein) configured to recruit a post-transcriptional regulating moiety (e.g., a spliceosomal moiety) (such as described herein), wherein the set of engineered polynucleotides are configured to specifically bind the RNA (e.g., the mRNA, such as the pre-mRNA) at a plurality of target sequences comprising the target sequence (such as described herein).

Vectors

In some embodiments described herein include a vector or a plasmid comprising a nucleic acid sequence encoding an engineered polynucleotide as described herein.

In some embodiments described herein include a plurality of vectors or a plurality of plasmids comprising a plurality of nucleic acid sequences each encoding an engineered polynucleotide as described herein. In some embodiments, the plurality of vectors or the plurality of plasmids comprise the plurality of nucleic acid sequences encoding more than one engineered polynucleotide as described herein. In some embodiments, the plurality of vectors or the plurality of plasmids comprise the plurality of nucleic acid sequences encoding a plurality of engineered polynucleotides (each independently described herein).

Pharmaceutical Composition(s)

Described herein, in some embodiments, is a pharmaceutical composition comprising the engineered polynucleotide described herein, or a plasmid, a vector, or an isolated DNA encoding the sequence thereof. Pharmaceutical composition, as used herein, refers to a mixture of at least one engineered polynucleotide or a vector encoding the at least one engineered polynucleotide, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. Optionally, the compositions include two or more pharmaceutical composition as discussed herein. In practicing the methods of treatment or use provided herein, therapeutically effective amounts of pharmaceutical compositions described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the pharmaceutical composition used and other factors. The pharmaceutical compositions can be used singly or in combination with one or more pharmaceutical compositions as components of mixtures. The pharmaceutical commotions described herein comprise the engineered polynucleotide, the compositions, the cells contacted with the engineered polynucleotide or contacted with the composition comprising the engineered polynucleotide, or a combination thereof.

The pharmaceutical formulations described herein are administered to a subject by appropriate administration routes, including but not limited to, intravenous, intraarterial, oral, parenteral, buccal, topical, transdermal, rectal, intramuscular, subcutaneous, intraosseous, transmucosal, inhalation, or intraperitoneal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a pharmaceutical composition are manufactured in a conventional manner, such as, by way of example only, by means of conventional mixing, dissolving, granulating, dragee-making, levigating, emulsifying, encapsulating, entrapping or compression processes.

Kit(s)

Described herein, in some embodiments, are kits for using the engineered polynucleotide, the compositions, or the pharmaceutical compositions described herein. In some embodiments, the kits disclosed herein may be used to treat a disease or condition in a subject. In some embodiments, the kit comprises an assemblage of materials or components apart from the engineered polynucleotide, the composition, or the pharmaceutical composition. In some embodiments, the kit comprises the components for assaying and selecting for suitable oligonucleotide for treating a disease or a condition. In some embodiments, the kit comprises components for performing assays such as enzyme-linked immunosorbent assay (ELISA), single-molecular array (Simoa), PCR, or qPCR. The exact nature of the components configured in the kit depends on its intended purpose. For example, some embodiments are configured for the purpose of treating a disease or condition disclosed herein in a subject. In some embodiments, the kit is configured particularly for the purpose of treating mammalian subjects. In some embodiments, the kit is configured particularly for the purpose of treating human subjects.

Instructions for use may be included in the kit. In some embodiments, the kit comprises instructions for administering the composition to a subject in need thereof. In some embodiments, the kit comprises instructions for further engineering the engineered polynucleotide. In some embodiments, the kit comprises instructions thawing or otherwise restoring biological activity of the engineered polynucleotide, which may have been cryopreserved or lyophilized during storage or transportation. In some embodiments, the kit comprises instructions for measuring efficacy for its intended purpose (e.g., therapeutic efficacy if used for treating a subject).

Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit may be provided to the practitioner stored in any convenient and suitable ways that preserve their operability and utility. For example, the engineered polynucleotide, the composition, or the pharmaceutical composition may be in dissolved, dehydrated, or lyophilized form. The components are typically contained in suitable packaging material(s).

Methods

Described herein are methods for utilizing an engineered polynucleotide (such as described herein), such as a method for altering a ribonucleic acid (RNA) (e.g., a messenger ribonucleic acid (mRNA), such as a pre-messenger ribonucleic acid (pre-mRNA)) in a cell. The method may comprise contacting the cell with the engineered polynucleotide (such as described herein) that comprises one or more targeting moiety and a recruiting moiety. The one or more targeting moiety may bind to the RNA (e.g., the mRNA, such as the pre-mRNA) (such as described herein) at a target sequence (such as described herein) therein, and the recruiting moiety recruits a post-transcriptional regulating moiety (e.g., a spliceosomal moiety) (such as described herein) within proximity of the target sequence of the RNA (e.g., the mRNA, such as the pre-mRNA) to alter the RNA (e.g., the mRNA, such as the pre-mRNA) in the cell, thereby yielding one or more altered RNA (e.g., one or more altered mRNA, such as one or more altered pre-mRNA). In some embodiments, the method alters an expression or activity of the target gene. In some embodiments, prior to the contacting, the cell exhibits an aberrant messenger ribonucleic acid (mRNA) or protein corresponding to the target gene. In some embodiments, a targeting moiety of the one or more targeting moiety is sufficiently identical or complementary to a consensus sequence in the target sequence of a target gene (e.g., microtubule associated protein tau (MAPT)).

Described herein include a method for altering a ribonucleic acid (RNA) (e.g., a messenger ribonucleic acid (mRNA), such as a pre-messenger ribonucleic acid (pre-mRNA)) at a plurality of locations in a cell. The method may comprise contacting the cell with a set of engineered polynucleotides (such as each independently described herein). An engineered polynucleotide may comprise one or more targeting moiety and a recruiting moiety. The one or more targeting moiety may bind to the RNA (e.g., the mRNA, such as the pre-mRNA) (such as described herein) at a plurality of target sequences (such as described herein) therein. Each recruiting moiety may recruit a post-transcriptional regulating moiety (e.g., a spliceosomal moiety) (such as described herein) within proximity of a target sequence of the RNA (e.g., the mRNA, such as the pre-mRNA) to alter the RNA (e.g., the mRNA, such as the pre-mRNA) in the cell, thereby yielding one or more altered RNA (e.g., one or more altered mRNA, such as one or more altered pre-mRNA). In some embodiments, the method alters an expression or activity of the target gene by altering (e.g., cleaving or/and chemically modifying) the RNA (e.g., the mRNA, such as the pre-mRNA) at the plurality of locations. In some embodiments, prior to the contacting, the cell exhibits an aberrant messenger ribonucleic acid (mRNA) or protein corresponding to the target gene. In some embodiments, one or each targeting moiety of the one or more targeting moiety is sufficiently identical or complementary to a consensus sequence in the target sequence of a target gene (e.g., microtubule associated protein tau (MAPT)).

In some embodiments, the method comprises delivering the engineered polynucleotide into a cell. In some embodiments, the method comprises delivering a polynucleotide encoding the engineered polynucleotide into a cell and subsequently expressing the engineered polynucleotide for modulating the expression or the activity of a gene encoded by the target sequence described herein. In some embodiments, the method comprises using the engineered polynucleotide for treating a disease or condition in a subject in need thereof. The disease or condition may be associated with an aberrant expression or activity of a target gene encoded by the RNA (e.g., the mRNA, such as the pre-mRNA). In some embodiments, the RNA (e.g., the mRNA, such as the pre-mRNA) corresponds to a target gene (e.g., microtubule associated protein tau (MAPT)).

FIG. 1 illustrates a schematic diagram for identifying splice donor and acceptor for designing the nucleotide sequence of the engineered polynucleotide, where the engineered polynucleotides or the methods described herein present an improvement over the currently available approaches for modulating expression or activity of a gene for treating a disease or condition. In some embodiments, the methods described herein modulate the expression or activity of a gene by the engineered polynucleotide targeting the transcript of the gene that causes a disease or condition. In some embodiments, the methods described herein comprise administering the engineered polynucleotide described herein to a subject in need thereof. In some cases, the methods described herein comprise utilizing the engineered polynucleotide to recruit a regulating moiety to modulate the expression or activity of the gene that causes the disease or condition, thereby treating the disease or condition. In some aspects, the methods described herein comprise utilizing the engineered polynucleotide to stabilize the assembly of the regulating moiety to modulate the expression or activity of the gene that causes the disease or condition, thereby treating the disease or condition.

Described herein, in some embodiments, are methods of delivering the engineered polynucleotides described herein to a cell. In some embodiments, the method comprises delivering directly or indirectly engineered polynucleotides to the cell. In some embodiments, the method comprises contacting the cell with a composition comprising the engineered polynucleotide described herein. In some embodiments, the method comprises expressing the engineered polynucleotide described herein in the cell. In some embodiments, the engineered polynucleotide or vector encoding the engineered polynucleotide can be delivered into the cell via any of the transfection methods described herein. In some embodiments, the engineered polynucleotide can be delivered into the cell via the use of expression vectors. In the context of an expression vector, the vector can be readily introduced into the cell described herein by any method in the art. For example, the expression vector can be transferred into the cell by physical, chemical, or biological means.

Physical methods for introducing the engineered polynucleotide or vector encoding the engineered polynucleotide into the cell can include calcium phosphate precipitation, lipofection, particle bombardment, microinjection, gene gun, electroporation, and the like. Methods for producing cells comprising vectors and/or exogenous nucleic acids are suitable for methods herein. One method for the introduction of engineered polynucleotide or vector encoding the engineered polynucleotide into a host cell is calcium phosphate transfection.

Chemical means for introducing the engineered polynucleotide or vector encoding the engineered polynucleotide into the cell can include colloidal dispersion systems, such as macromolecule complexes, nanocapsules, microspheres, beads, and lipid-based systems including oil-in-water emulsions, micelles, mixed micelles, spherical nucleic acid (SNA), liposomes, or lipid nanoparticles. An example colloidal system for use as a delivery vehicle in vitro and in vivo is a liposome (e.g., an artificial membrane vesicle). Other methods of state-of-the-art targeted delivery of nucleic acids are available, such as delivery of engineered polynucleotide or vector encoding the engineered polynucleotide with targeted nanoparticles.

In the case where a non-viral delivery system is utilized, an example delivery vehicle is a liposome. The use of lipid formulations is contemplated for the introduction of the engineered polynucleotide or vector encoding the engineered polynucleotide into a cell (in vitro, ex vivo, or in vivo). In another aspect, the engineered polynucleotide or vector encoding the engineered polynucleotide can be associated with a lipid. The engineered polynucleotide or vector encoding the engineered polynucleotide associated with a lipid can be encapsulated in the aqueous interior of a liposome, interspersed within the lipid bilayer of a liposome, attached to a liposome via a linking molecule that is associated with both the liposome and the engineered polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, in some embodiments, they are present in a bilayer structure, as micelles, or with a "collapsed" structure. Alternately, they are simply be interspersed in a solution, possibly forming aggregates that are not uniform in size or shape. Lipids are fatty substances which are, in some embodiments, naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use are obtained from commercial sources. Stock solutions of lipids in chloroform or chloroform/methanol are often stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes are often characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, compositions that have different structures in solution than the normal vesicular structure are also encompassed. For example, the lipids, in some embodiments, assume a micellar structure or merely exist as nonuniform aggregates of lipid molecules. Also contemplated are lipofectamine-nucleic acid complexes.

In some cases, non-viral delivery method comprises lipofection, nucleofection, microinjection, biolistics, virosomes, liposomes, immunoliposomes, exosomes, polycation or lipid:cargo conjugates (or aggregates), naked polypeptide (e.g., recombinant polypeptides), naked DNA, artificial virions, and agent-enhanced uptake of polypeptide or DNA. In some embodiments, the delivery method comprises conjugating or encapsulating the compositions or the engineered polynucleotides described herein with at least one polymer such as natural polymer or synthetic materials. The polymer can be biocompatible or biodegradable. Non-limiting examples of suitable biocompatible, biodegradable synthetic polymers can include aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, and poly(anhydrides). Such synthetic polymers can be homopolymers or copolymers (e.g., random, block, segmented, graft) of a plurality of different monomers, e.g., two or more of lactic acid, lactide, glycolic acid, glycolide, epsilon-caprolactone, trimethylene carbonate, p-dioxanone, etc. In an example, the scaffold can be comprised of a polymer comprising glycolic acid and lactic acid, such as those with a ratio of glycolic acid to lactic acid of 90/10 or 5/95. Non-limiting examples of naturally occurring biocompatible, biodegradable polymers can include glycoproteins, proteoglycans, polysaccharides, glycosamineoglycan (GAG) and fragment(s) derived from these components, elastin, laminins, decrorin, fibrinogen/fibrin, fibronectins, osteopontin, tenascins, hyaluronic acid, collagen, chondroitin sulfate, heparin, heparan sulfate, ORC, carboxymethyl cellulose, and chitin.

In some cases, the engineered polynucleotide or vector encoding the engineered polynucleotide described herein can be packaged and delivered to the cell via extracellular vesicles. The extracellular vesicles can be any membrane-bound particles. In some embodiments, the extracellular vesicles can be any membrane-bound particles secreted by at least one cell. In some instances, the extracellular vesicles can be any membrane-bound particles synthesized in vitro. In some instances, the extracellular vesicles can be any membrane-bound particles synthesized without a cell. In some cases, the extracellular vesicles can be exosomes, microvesicles, retrovirus-like particles, apoptotic bodies, apoptosomes, oncosomes, exophers, enveloped viruses, exomeres, or other very large extracellular vesicles.

Described herein, in some aspects, are methods for modulating or altering expression or activity of a gene encoded by a target sequence in a cell. In some embodiments, the target sequence is a pre-messenger ribonucleic acid (pre-mRNA) in a cell. In some embodiments, the method comprises contacting the cell with an engineered polynucleotide comprising one or more targeting moieties and a recruiting moiety. In some embodiments, the one or more targeting moieties bind to said pre-mRNA at a target sequence therein. In some embodiments, the recruiting moiety recruits a post-transcriptional regulating moiety (e.g., a spliceosomal moiety) within proximity of said target sequence of said pre-mRNA to alter said pre-mRNA in said cell, thereby yielding one or more altered pre-mRNA. In some embodiments, the pre-mRNA corresponds to a target gene such as microtubule associated protein tau (MAPT). In some embodiments, the method, when the engineered polynucleotide binds and recruits the spliceosomal moiety to the target sequence, increases an expression or activity of the target gene. In some embodiments, the method, when the engineered polynucleotide binds and recruits the spliceosomal moiety to the target sequence, decreases an expression or activity of the target gene. In some embodiments, the method, when the engineered polynucleotide binds and recruits the spliceosomal moiety to the target sequence, corrects aberrant messenger ribonucleic acid (mRNA) or protein corresponding to said target gene.

In some embodiments, the method comprises contacting or delivering two or more engineered polynucleotides into a single cell, where the engineered polynucleotides each comprise one or more targeting moieties configured to bind to two or more target sequences. The two or more target sequences can be located on the same strand of the pre-mRNA encoding a target gene. The two or more target sequences can be located on different strands of pre-mRNA encoding the same target gene. The two or more target sequences can be located on different strands of pre-mRNA, where each strand of the pre-mRNA can encode different target gene. In some embodiments, the method comprises two or more engineered polynucleotides configured to specifically bind said pre-mRNA at a plurality of target sequences comprising said target sequence.

Disclosed herein, in some embodiments, are methods of treating a disease or condition by modulating expression or activity of a target gene in a cell, thereby treating the disease or condition. In some embodiments, the method comprises treating a disease or condition by correcting aberrant messenger ribonucleic acid (mRNA) or protein corresponding to said target gene. In some embodiments, the disease or condition is associated with increased expression or activity of any one of the target gene described herein. In some embodiments, the disease or condition is associated with decreased expression or activity of any one of the target gene described herein. In some embodiments, the disease or condition is associated with splicing of aberrant messenger ribonucleic acid (mRNA) or protein corresponding to of any one of the target gene described herein.

In some embodiments, the engineered polynucleotide or pharmaceutical composition comprising the engineered polynucleotide can be administered to the subject alone (e.g., standalone treatment). In some embodiments, the engineered polynucleotide or pharmaceutical composition comprising the engineered polynucleotide is administered in combination with an additional agent. In some cases, the additional agent as used herein is administered alone. The engineered polynucleotide or pharmaceutical composition comprising the engineered polynucleotide and the additional agent can be administered together or sequentially. The combination therapies can be administered within the same day, or can be administered one or more days, weeks, months, or years apart.

In some embodiments, the engineered polynucleotide or pharmaceutical composition comprising the engineered polynucleotide is a first-line treatment for the disease or condition. In some embodiments, the engineered polynucleotide or pharmaceutical composition comprising the engineered polynucleotide is a second-line, third-line, or fourth-line treatment. In some embodiments, the engineered polynucleotide or pharmaceutical composition comprising the engineered polynucleotide comprises at least one, two, three, four, five, six, seven, eight, nine, 10, 20, 30 or more oligonucleotide. In general, method disclosed herein comprises administering the engineered polynucleotide or pharmaceutical composition comprising the engineered polynucleotide by oral administration. However, in some instances, method comprises administering the engineered polynucleotide or pharmaceutical composition comprising the engineered polynucleotide by intraperitoneal injection. In some instances, the method comprises administering the engineered polynucleotide or pharmaceutical composition comprising the engineered polynucleotide by intravenous ("i.v.") administration. It is conceivable that one can also administer the engineered polynucleotide or pharmaceutical composition comprising the engineered polynucleotide disclosed herein by other routes such as subcutaneous injection, intramuscular injection, intradermal injection, transdermal injection percutaneous administration, intranasal administration, intralymphatic injection, rectal administration intragastric administration, or any other suitable parenteral administration. In some embodiments, routes for local delivery closer to site of injury or inflammation are preferred over systemic routes. Routes, dosage, time points, and duration of administrating therapeutics can be adjusted. In some embodiments, administration of therapeutics is prior to, or after, onset of either, or both, acute and chronic symptoms of the disease or condition.

Suitable dose and dosage administrated to a subject is determined by factors including, but no limited to, the particular the engineered polynucleotide, composition, or pharmaceutical composition, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject being treated.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as example(s).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Splicing in Neurodegenerative Diseases

Alzheimer's disease (AD) and other tauopathies represent neurodegenerative disorders. AD is characterized by the presence of amyloid-β plaques and hyperphosphorylated Tau aggregation in neurofibrillary tangles, neuropil threads, and neuritic plaques in the brain. Progressive loss of white matter in regions displaying tau pathology is also observed (Kneynsberg et al., 2017). Furthermore, literature data have shown that AD is also characterized by U1 snRNP nuclei depletion, accumulation, and aggregation in the cytoplasm along with splicing disorders (Bai et al., 2013, 2014, 2018; Zhu et al., 2020). Besides, the basic-acidic dipeptide domain of U1-70K was demonstrated to interact with Tau from AD brains, and both U1-70K and Tau co-localize to neurofibrillary tangles in late-onset sporadic and familial cases of AD (Bishof et al., 2018).

In a study integrating data from human postmortem brain tissue and *Drosophila melanogaster* models, Hsieh and collaborators showed that AD Tau neurofibrillary tangle pathology disrupts spliceosome activity leading to transcriptome failure and ultimately CNS dysfunction and neurodegeneration. They hypothesize that Tau has involved in spliceosome cytoplasmic sequestration and disrupting snRNP assembly and/or stability. They showed also that some spliceosome components (including U1-70K) are physically associated with Tau in human brains with AD pathology, and in *Drosophila*, genetic manipulation of these factors enhances Tau neurotoxicity. They confirmed an increasement of cryptic splicing load in human postmortem brains with Tau pathology (Hsieh et al., 2019).

REFERENCES

Bai, B., Chen, P. C., Hales, C. M., Wu, Z., Pagala, V., High, A. A., Levey, A. I., Lah, J. J., & Peng, J. (2014). Integrated Approaches for Analyzing U1-70K Cleavagein Alzheimer's Disease. Journal of Proteome Research, 13(11), 4526. https://doi.org/10.1021/PR5003593

Bai, B., Hales, C. M., Chen, P. C., Gozal, Y., Dammer, E. B., Fritz, J. J., Wang, X., Xia, Q., Duong, D. M., Street, C., Cantero, G., Cheng, D., Jones, D. R., Wu, Z., Li, Y., Diner, I., Heilman, C. J., Rees, H. D., Wu, H., . . . Peng, J. (2013). U1 small nuclear ribonucleoprotein complex and RNA splicing alterations in Alzheimer's disease. Proceedings of the National Academy of Sciences of the United States of America, 110(41), 16562-16567. https://doi.org/10.1073/pnas.1310249110

Bai, B., Wang, S., Chen, Y., Jia, J., Tian, X., Liu, C., Xia, Y., & Xie, H. (2018). Effects of RNA Splicing Inhibitors on Amyloid PrecursorProtein Expression. ACS Omega, 3(3), 2798. https://doi.org/10.1021/ACSOMEGA.7B02073

Bishof, I., Dammer, E. B., Duong, D. M., Kundinger, S. R., Gearing, M., Lah, J. J., Levey, A. I., & Seyfried, N. T. (2018). RNA-binding proteins with basic-acidic dipeptide (BAD) domains self-assemble and aggregate in Alzheimer's disease. The Journal of Biological Chemistry, 293(28), 11047. https://doi.org/10.1074/JBC.RA118.001747

Hsieh, Y. C., Guo, C., Yalamanchili, H. K., Abreha, M., Al-Ouran, R., Li, Y., Dammer, E. B., Lah, J. J., Levey, A. I., Bennett, D. A., De Jager, P. L., Seyfried, N. T., Liu, Z., & Shulman, J. M. (2019). Tau-Mediated Disruption of the Spliceosome Triggers Cryptic RNA Splicing and Neurodegeneration in Alzheimer's Disease. Cell Reports, 29(2), 301-316.e10. https://doi.org/10.1016/J.CELREP.2019.08.104

Kneynsberg, A., Combs, B., Christensen, K., Morfini, G., & Kanaan, N. M. (2017). Axonal degeneration in tauopathies: Disease relevance and underlying mechanisms. Frontiers in Neuroscience, 11(OCT), 1-14. https://doi.org/10.3389/fnins.2017.00572

Zhu, W., Wei, X., Wang, Y., Li, J., Peng, L., Zhang, K., & Bai, B. (2020). Effects of U1 Small Nuclear Ribonucleoprotein Inhibition on the Expression of Genes Involved in Alzheimer's Disease. ACS Omega, 5(39), 25306-25311. https://doi.org/10.1021/acs omega.0c03568

EXAMPLES

The following illustrative examples are representative of embodiments of the stimulation, systems, and methods described herein and are not meant to be limiting in any way.

Example 1. Modulating Expression of Target Gene with Engineered Polynucleotide

Cells obtained from a cell like (e.g., HEK293 cell line) are cultured and maintained in cell culture medium. The cells can then be contacted with the engineered polynucleotide or a vector encoding the engineered polynucleotide for delivery of the engineered polynucleotide or a vector encoding the engineered polynucleotide into the cells by any one of the delivery method described herein. After the engineered polynucleotide is delivered into the cells, the cells can be cultured for a period of time to allow the engineered polynucleotide to modulate the expression or activity of the target gene. Cells can then be harvested and lysed for measurement of the expression or activity of the target gene. For example, the cells can be harvested and lyzed and examined for the abundance of pre-mRNA, mRNA, or protein of the target gene modulated by the engineered polynucleotide. In other cases, the cells can be fixed and prepared for microscopic examination. For example, the cells can be examined under microscope for the presence or changes of the abundance of the inclusion body or amyloid plaque associated with any one of the target gene described herein (e.g., tau plaques encoded by MAPT target gene).

Example 2. Treating a Neurological Disease by Editing RNA

A subject is diagnosed with Alzheimer's disease stemmed from an aberrant splicing of tau protein encoded by target gene MAPT. The subject is prescribed a dosing regimen of a pharmaceutical composition comprising a chemically modified engineered polynucleotide disclosed herein for recruiting and stabilizing at least one regulating moiety to the target MAPT pre-mRNA. The chemically modified engineered polynucleotide, upon binding to the MAPT pre-mRNA recruits and stabilizes at least one regulating moiety for correctly splicing the MAPT pre-mRNA. In some embodiments, the chemically modified engineered polynucleotide increases the specificity or efficiency of recruiting and stabilizing the at least one regulating moiety RNA editing entity. The modulation of the MAPT pre-mRNA by the engineered polynucleotide decreases the amount of tau plaques in the subject, thereby treating or decreasing the symptoms of Alzheimer's in the subject.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

Example 3. Spliceosome Modulation by Engineered Polynucleotides

The effects of the chemically modified engineered polynucleotides described herein on splicing will be determined by RNA-Seq.

The RNA-Seq protocol will consist of culture, for sixteen days, of excitatory neurons derived from iPSCs (Induced Pluripotent Stem Cells) from healthy patients (HDC—Healthy Donor Cell) and from patients with Alzheimer's disease (ADC—Alzheimer's disease Donor Cell). After six days of culture, HDC and ADC neurons will be treated for 10 days with two distinct concentrations of an engineered polynucleotide comprising a targeting moiety and a recruiting moiety (e.g. ASMO-1, ASMO-2). Negative controls for both HDC and ADC will consist of 10 days of culture in a medium with no compound treatment. After the sixteen days of cell culture and treatment, RNA extraction, library preparation, and RNA sequencing will be carried out, targeting 100 million reads per condition. This experiment will be performed with three replicates and only one repeat.

Bioinformatics analysis will be performed with RNA seq generated raw data and will be consisted of the following steps: (i) quality control of raw read data; (ii) mapping on Human reference genome; (iii) Transcripts quantification and differential expression analysis to determine differentially expressed genes; (iv) Gene Ontology enrichment analysis (v) Analyses of Key pathway (like pathways related with TAU and Alzheimer's disease); (vi) Comparison of the differentially expressed genes from RNA-seq and the targets candidates for ASMO-1 predicted in silico.

The RNA seq data analysis of HDC and ADC negative controls will identify gene expression differences and associated pathways between healthy and Alzheimer's disease cells. It is expected that these differences observed in HDC and ADC control will highlight important hallmarks and biomarkers of Alzheimer's disease.

Furthermore, in the tested treatment conditions, the RNA seq data will demonstrate that ASMO-1 (for example) enhances splicing of predicted target candidates such as MAPT pre-mRNA through differential gene expression analysis, evidencing rescue of the expression levels of these candidates in AD treated cells back to healthy levels comparable to HDC control. Abnormally unregulated genes in ADC controls in relation to HDC will be downregulated in AD-treated cells, and vice versa. Additionally, these beneficial expression modulations by ASMO-1 in treated AD cells (expected to be represented by, for example, the TAU expression modulation) will trigger an indirect cascade of downstream effects making the gene expression pattern, as a whole, more similar to the expression pattern of HD untreated cell and less similar to AD untreated cells and their hallmark pathways (NFT accumulation, amyloid β cleavage, amyloid β degradation, APOE-cholesterol pathway, etc).

In the context of pharmaceutical safety, we expect that RNA seq data analysis of HDC treated with ASMO-1 ensure that no harmful gene expression profiles are exhibited by the treatment in at least one of the concentrations evaluated.

What is claimed is:

1. An engineered polynucleotide comprising:
   a) a first nucleotide sequence complementary to a splice site of a pre-messenger ribonucleic acid (pre-mRNA),
   b) a recruiting nucleotide sequence comprising: (i) a nucleotide sequence complementary to at least 4 nucleotides of the Stem-Loop II (SL2) of an U1 snRNA, and/or (ii) a nucleotide sequence comprising a phosphorothioate internucleotide linkage that binds to a U1-C zinc finger, and
   c) a second nucleotide sequence complementary to a sequence 5' or 3' to said splice site of the pre-mRNA, wherein said splice site and said sequence 5' or 3' to said splice site are separated by no more than five nucleotides;
   wherein said recruiting nucleotide sequence comprises an apical loop, an upper stem adjacent to said apical loop, a lower stem, and an internal loop situated between said upper stem and said lower stem.

2. The engineered polynucleotide of claim 1, wherein
   a) said upper stem is formed by hybridization of two complementary upper stem sequences and said lower stem is formed by hybridization of two complementary lower stem sequences and wherein each of said two complementary upper stem sequences and/or each of said two complementary lower stem sequences is no more than 5 nucleotides in length;
   b) said internal loop is composed of two nucleic acid sequences and each of said two nucleic acid sequences is no more than 5 nucleotides in length; and
   c) said apical loop is no more than 8 nucleotides in length.

3. The engineered polynucleotide of claim 1, wherein said pre-mRNA does not base pair with the RNA binding domain (RBD) of said U1 snRNA when said first nucleotide sequence is hybridized to said splice site or when said second nucleotide is hybridized to said sequence 5' or 3' to said splice site.

4. The engineered polynucleotide of claim 1, wherein the first nucleotide sequence comprises a phosphorothioate internucleotide linkage that binds with said U1-C zinc-finger protein.

5. The engineered polynucleotide of claim 1, wherein said at least 4 nucleotides of the SL2 of said U1 snRNA comprises 5'-GGCCU-3'.

6. The engineered polynucleotide of claim 1, wherein said recruiting nucleotide sequence that is at least 90% identical to, or complementary to, any one of SEQ ID NOs: 1-4.

7. The engineered polynucleotide of claim 1, wherein said engineered polynucleotide comprises a 2'-modified nucleotide.

8. The engineered polynucleotide of claim 1, wherein at least 50% of the nucleotides of said engineered polynucleotide are 2'-modified nucleotides.

9. The engineered polynucleotide of claim 7, wherein said 2'-modified nucleotide comprises a 2'-methoxy, 2'-methoxymethyl, 2'-methoxyethyl, 2' fluoro, or 2'-aminoethyl nucleotide.

10. The engineered polynucleotide of claim 1, wherein said engineered polynucleotide comprises nucleotides connected by internucleotide linkages and at least one of said internucleotide linkages does not comprise a phosphate.

11. The engineered polynucleotide of claim 10, wherein at least one of said internucleotide linkages comprises a phosphorothioate.

12. The engineered polynucleotide of claim 10, wherein at least 50% of said internucleotide linkages comprise a phosphorothioate.

13. The engineered polynucleotide of claim 1, wherein said engineered polynucleotide is 10 to 40 nucleotides in length.

14. The engineered polynucleotide of claim 1, wherein said engineered polynucleotide is 24 nucleotides or 20 nucleotides in length.

15. The engineered polynucleotide of claim 1, wherein a spliceosomal moiety initiates a splicing process of said pre-mRNA when said first nucleotide sequence and/or said second nucleotide sequence is associated with said pre-mRNA.

16. A method for altering a pre-messenger ribonucleic acid (pre-mRNA) in a cell, the method comprising contacting said cell with the engineered polynucleotide of claim 1, wherein said first nucleotide sequence hybridizes with said pre-mRNA at said splice site, and said second nucleotide sequence hybridizes with said pre-mRNA at said sequence 5' or 3' to said splice site, and said recruiting nucleotide sequence hybridizes to the SL2 of said U1 snRNA and/or binds to said U1-C zinc finger, wherein said U1 snRNA and the U1-C zinc finger are components of a spliceosome, to splice said pre-mRNA in said cell, thereby altering the pre-mRNA.

17. The method of claim 16, wherein said pre-mRNA is encoded by a target gene.

18. The method of claim 17, wherein said target gene comprises microtubule associated protein tau (MAPT).

19. The method of claim 17, wherein the method alters an expression or activity of said target gene.

20. The method of claim 17, wherein, prior to said contacting, said cell comprises an aberrant messenger ribonucleic acid (mRNA) or protein corresponding to said target gene.

21. A set of engineered polynucleotides each independently comprising: (i) one or more nucleotide sequences complementary to a splice site and a sequence 5' or 3' to the splice site of a pre-messenger ribonucleic acid (pre-mRNA) and (ii) a recruiting nucleotide sequence comprising a sequence complementary to at least 4 nucleotides of a sequence of Stem-Loop II (SL2) of an U1 snRNA and/or a sequence comprising a phosphorothioate internucleotide linkage that binds to a U1-C protein zinc finger, wherein said set of engineered polynucleotides specifically bind said pre-mRNA at a plurality of target sequences.

22. The engineered polynucleotide of claim 1, wherein the engineered polynucleotide stabilizes an interaction of said pre-mRNA with a spliceosome component.

23. The engineered polynucleotide of claim 1, wherein said splice site comprises 5'-GU-3'.

24. An engineered polynucleotide comprising:
a) a first targeting moiety configured to specifically bind a pre-messenger ribonucleic acid (pre-mRNA) at a first targeted sequence therein, wherein the first targeting moiety comprises a sequence identical or complementary to 5'-GTCCA-3',
b) a recruiting moiety comprising a sequence that is at least 90% similar or complementary to SEQ ID NO. 1 and is configured to recruit a spliceosomal moiety that comprises U1 snRNA and a U1-C protein, and
c) a second targeting moiety configured to specifically bind the pre-mRNA at a second targeted sequence therein, wherein the second targeting moiety comprises a sequence identical or complementary to 5'-CG-3';
wherein said recruiting moiety comprises an apical loop, an upper stem adjacent to said apical loop, a lower stem, and an internal loop situated between said upper stem and said lower stem.

25. The engineered polynucleotide of claim 1, wherein said recruiting nucleotide sequence is complementary to, and/or able to hybridize or bind to one or more additional U1 snRNP components comprising U1-70K, U1-A, or Sm.

26. The engineered polynucleotide of claim 1, wherein said engineered polynucleotide is 40 or more nucleotides in length.

27. The engineered polynucleotide of claim 10, wherein said internucleotide linkages comprises a methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, or methyleneoxymethylimino.

28. The engineered polynucleotide of claim 1, wherein said engineered polynucleotide comprises nucleotides connected by internucleotide linkages, and at least one of said internucleotide linkages comprises a sulfur (S); selenium (Se); BR3, wherein each R is independently selected from the group consisting of hydrogen, alkyl, and aryl; Carbon (C); or NR2, wherein each R is independently selected from the group consisting of a hydrogen, alkyl, and aryl.

* * * * *

SEQUENCE LISTING

```
Sequence total quantity: 26
SEQ ID NO: 1              moltype = DNA  length = 17
FEATURE                   Location/Qualifiers
source                    1..17
                          mol_type = other DNA
                          organism = synthetic construct
SEQUENCE: 1
ctaacctttc aggccag                                                    17

SEQ ID NO: 2              moltype = RNA  length = 17
FEATURE                   Location/Qualifiers
source                    1..17
                          mol_type = other RNA
                          organism = synthetic construct
SEQUENCE: 2
ctaacctttc aggccag                                                    17
```

```
SEQ ID NO: 3              moltype = DNA  length = 13
FEATURE                   Location/Qualifiers
source                    1..13
                          mol_type = other DNA
                          organism = synthetic construct
SEQUENCE: 3
atcgtcagct tac                                                          13

SEQ ID NO: 4              moltype = RNA  length = 13
FEATURE                   Location/Qualifiers
source                    1..13
                          mol_type = other RNA
                          organism = synthetic construct
SEQUENCE: 4
atcgtcagct tac                                                          13

SEQ ID NO: 5              moltype = DNA  length = 24
FEATURE                   Location/Qualifiers
source                    1..24
                          mol_type = other DNA
                          organism = synthetic construct
SEQUENCE: 5
gtccactaac ctttcaggcc agcg                                              24

SEQ ID NO: 6              moltype = RNA  length = 24
FEATURE                   Location/Qualifiers
source                    1..24
                          mol_type = other RNA
                          organism = synthetic construct
SEQUENCE: 6
gtccactaac ctttcaggcc agcg                                              24

SEQ ID NO: 7              moltype = DNA  length = 20
FEATURE                   Location/Qualifiers
source                    1..20
                          mol_type = other DNA
                          organism = synthetic construct
SEQUENCE: 7
gcatcgtcag cttaccttgg                                                   20

SEQ ID NO: 8              moltype = RNA  length = 20
FEATURE                   Location/Qualifiers
source                    1..20
                          mol_type = other RNA
                          organism = synthetic construct
SEQUENCE: 8
gcatcgtcag cttaccttgg                                                   20

SEQ ID NO: 9              moltype = AA   length = 33
FEATURE                   Location/Qualifiers
source                    1..33
                          mol_type = protein
                          organism = synthetic construct
SEQUENCE: 9
YYCDYCDTYL THDSPSVRKT HCTGRKHRDN VKF                                    33

SEQ ID NO: 10             moltype = RNA  length = 11
FEATURE                   Location/Qualifiers
source                    1..11
                          mol_type = unassigned RNA
                          organism = unidentified
SEQUENCE: 10
atacttacct g                                                            11

SEQ ID NO: 11             moltype = RNA  length = 12
FEATURE                   Location/Qualifiers
source                    1..12
                          mol_type = unassigned RNA
                          organism = unidentified
SEQUENCE: 11
ggcctcacgt tc                                                           12

SEQ ID NO: 12             moltype = DNA  length = 52
FEATURE                   Location/Qualifiers
source                    1..52
                          mol_type = unassigned DNA
                          organism = unidentified
```

-continued

```
SEQUENCE: 12
ctcccgtcct cgcctctgtc gactatcagg taagcgccgc ggctccgaaa tc            52

SEQ ID NO: 13            moltype = DNA    length = 64
FEATURE                  Location/Qualifiers
source                   1..64
                         mol_type = other DNA
                         organism = synthetic construct
SEQUENCE: 13
gaggcgacag gagagggcag gagcggagac agctgatagt ccattcgcgg cgccgaggct    60
ttag                                                                 64

SEQ ID NO: 14            moltype = RNA    length = 164
FEATURE                  Location/Qualifiers
source                   1..164
                         mol_type = unassigned RNA
                         organism = unidentified
modified_base            6
                         mod_base = OTHER
                         note = 2'-O-methyl uridine
modified_base            7
                         mod_base = OTHER
                         note = 2'-O-methyl adenosine
modified_base            70
                         mod_base = OTHER
                         note = 2'-O-methyl Adenosine
SEQUENCE: 14
atacttacct ggcagggag ataccatgat cacgaaggtg gttttcccag ggcgaggctt     60
atccattgca ctccggatgt gctgaccct gcgatttccc caaatgtggg aaactcgact    120
gcataatttg tggtagtggg ggactgcgtt cgcgctttcc cctg                    164

SEQ ID NO: 15            moltype = RNA    length = 51
FEATURE                  Location/Qualifiers
source                   1..51
                         mol_type = genomic RNA
                         organism = Homo sapiens
SEQUENCE: 15
ccgtcctcgc ctctgtcgac tatcaggtaa gcgccgcggc tccgaaatct g             51

SEQ ID NO: 16            moltype = RNA    length = 55
FEATURE                  Location/Qualifiers
source                   1..55
                         mol_type = unassigned RNA
                         organism = unidentified
SEQUENCE: 16
ggatccattg cactccggat ccaggagata ccatgatcac gaaggtggtt ttcct         55

SEQ ID NO: 17            moltype = AA     length = 279
FEATURE                  Location/Qualifiers
source                   1..279
                         mol_type = protein
                         organism = unidentified
SEQUENCE: 17
GVPETRPNHT IYINNLNEKI KKDELKKSLY AIFSQFGQIL DILVSRSLKM RGQAFVIFKE    60
VSSATNALRS MQGFPFYDKP MRIQYAKTDS DIIAKMKGTF VERDRKREKR GSGSGSGSGS   120
GSGAETREER MERKRREKIE RRQQEVETEL KMWDPHNDPN AQGDAFKTLF VARVNYDTTE   180
SKLRREFEVY GPIKRIHMVY SKRSGKPRGY AFIEYEHERD MHSAYKHADG KKIDGRRVLV   240
DVERGRTVKG WRPRRLGGGL GGTRRGGADV NIRHSGRDD                          279

SEQ ID NO: 18            moltype = RNA    length = 51
FEATURE                  Location/Qualifiers
source                   1..51
                         mol_type = unassigned RNA
                         organism = unidentified
SEQUENCE: 18
ccgtcctcgc ctctgtcgac tatcaggtaa gcgccgcggc tccgaaatct g             51

SEQ ID NO: 19            moltype = RNA    length = 55
FEATURE                  Location/Qualifiers
source                   1..55
                         mol_type = unassigned RNA
                         organism = unidentified
SEQUENCE: 19
ggatccattg cactccggat ccaggagata ccatgatcac gaaggtggtt ttcct         55
```

```
SEQ ID NO: 20            moltype = AA   length = 279
FEATURE                  Location/Qualifiers
source                   1..279
                         mol_type = protein
                         organism = unidentified
SEQUENCE: 20
GVPETRPNHT IYINNLNEKI KKDELKKSLY AIFSQFGQIL DILVSRSLKM RGQAFVIFKE    60
VSSATNALRS MQGFPPYDKP MRIQYAKTDS DIIAKMKGTF VERDRKREKR GSGSGSGSGS   120
GSGAETREER MERKRREKIE RRQQEVETEL KMWDPHNDPN AQGDAFKTLF VARVNYDTTE   180
SKLRREFEVY GPIKRIHMVY SKRSGKPRGY AFIEYEHERD MHSAYKHADG KKIDGRRVLV   240
DVERGRTVKG WRPRRLGGGL GGTRRGGADV NIRHSGRDD                         279

SEQ ID NO: 21            moltype = AA   length = 145
FEATURE                  Location/Qualifiers
source                   1..145
                         mol_type = protein
                         organism = unidentified
SEQUENCE: 21
MPKYYCDYCD TYLTHDSPSV RKTHCTGRKH RDNVKFYYQK WMEEQAQHLI DATTAAFKAG    60
KITNNPFAGG PGGAPPKPAG VSIPPPNMGA PPRPGMPGMP YMPPLMNPMM GMRPPPIMNP   120
MAMMGPPPPL GTIPGVRPGI MNGPK                                        145

SEQ ID NO: 22            moltype = DNA   length = 24
FEATURE                  Location/Qualifiers
source                   1..24
                         mol_type = other DNA
                         organism = synthetic construct
modified_base            1
                         mod_base = OTHER
                         note = 2'-O-methyl Phosphorothioate Guanosine
modified_base            2
                         mod_base = OTHER
                         note = 2'-O-methyl Phosphorothioate Thymidine
modified_base            3
                         mod_base = OTHER
                         note = 2'-O-methyl Phosphorothioate Cytosine
modified_base            4
                         mod_base = OTHER
                         note = 2'-O-methyl Phosphorothioate Cytosine
modified_base            5
                         mod_base = OTHER
                         note = 2'-O-methyl Phosphorothioate (Thiol) adenosine
modified_base            6
                         mod_base = OTHER
                         note = Phosphorothioate Cytosine
modified_base            7
                         mod_base = OTHER
                         note = Phosphorothioate Thymidine
modified_base            8
                         mod_base = OTHER
                         note = Phosphorothioate Adenosine
modified_base            9
                         mod_base = OTHER
                         note = Phosphorothioate Adenosine
modified_base            10
                         mod_base = OTHER
                         note = Phosphorothioate Cytosine
modified_base            11
                         mod_base = OTHER
                         note = Phosphorothioate Cytosine
modified_base            12
                         mod_base = OTHER
                         note = Phosphorothioate Thymidine
modified_base            13
                         mod_base = OTHER
                         note = Phosphorothioate Thymidine
modified_base            14
                         mod_base = OTHER
                         note = Phosphorothioate Thymidine
modified_base            15
                         mod_base = OTHER
                         note = Phosphorothioate Cytosine
modified_base            16
                         mod_base = OTHER
                         note = Phosphorothioate Adenosine
modified_base            17
                         mod_base = OTHER
                         note = Phosphorothioate Guanosine
```

```
modified_base          18
                       mod_base = OTHER
                       note = Phosphorothioate Guanosine
modified_base          19
                       mod_base = OTHER
                       note = Phosphorothioate Cytosine
modified_base          20
                       mod_base = OTHER
                       note = 2'-O-methyl Phosphorothioate Cytosine
modified_base          21
                       mod_base = OTHER
                       note = 2'-O-methyl Phosphorothioate Adenosine
modified_base          22
                       mod_base = OTHER
                       note = 2'-O-methyl Phosphorothioate Guanosine
modified_base          23
                       mod_base = OTHER
                       note = 2'-O-methyl Phosphorothioate Cytosine
modified_base          24
                       mod_base = OTHER
                       note = 2'-O-methyl Phosphorothioate Guanosine
SEQUENCE: 22
gtccactaac ctttcaggcc agcg                                          24

SEQ ID NO: 23          moltype = RNA  length = 20
FEATURE                Location/Qualifiers
source                 1..20
                       mol_type = other RNA
                       organism = synthetic construct
modified_base          11
                       mod_base = OTHER
                       note = 2'-O-methyl Adenosine
SEQUENCE: 23
tatccattgc actccggatg                                               20

SEQ ID NO: 24          moltype = DNA  length = 20
FEATURE                Location/Qualifiers
source                 1..20
                       mol_type = other DNA
                       organism = synthetic construct
modified_base          1
                       mod_base = OTHER
                       note = 2'-O-methyl Phosphorothioate Guanosine
modified_base          2
                       mod_base = OTHER
                       note = 2'-O-methyl Phosphorothioate Cytosine
modified_base          3
                       mod_base = OTHER
                       note = 2'-O-methyl Phosphorothioate Adenosine
modified_base          4
                       mod_base = OTHER
                       note = 2'-O-methyl Phosphorothioate Thymidine
modified_base          5
                       mod_base = OTHER
                       note = 2'-O-methyl Phosphorothioate Cytosine
modified_base          6
                       mod_base = OTHER
                       note = Phosphorothioate Guanosine
modified_base          7
                       mod_base = OTHER
                       note = Phosphorothioate Thymidine
modified_base          8
                       mod_base = OTHER
                       note = Phosphorothioate Cytosine
modified_base          9
                       mod_base = OTHER
                       note = Phosphorothioate Adenosine
modified_base          10
                       mod_base = OTHER
                       note = Phosphorothioate Guanosine
modified_base          11
                       mod_base = OTHER
                       note = Phosphorothioate Cytosine
modified_base          12
                       mod_base = OTHER
                       note = Phosphorothioate Thymidine
modified_base          13
                       mod_base = OTHER
                       note = Phosphorothioate Thymidine
```

|               |                                                      |
|---------------|------------------------------------------------------|
| modified_base | 14                                                   |
|               | mod_base = OTHER                                     |
|               | note = Phosphorothioate Adenosine                    |
| modified_base | 15                                                   |
|               | mod_base = OTHER                                     |
|               | note = Phosphorothioate Cytosine                     |
| modified_base | 16                                                   |
|               | mod_base = OTHER                                     |
|               | note = 2'-O-methyl Phosphorothioate Cytosine         |
| modified_base | 17                                                   |
|               | mod_base = OTHER                                     |
|               | note = 2'-O-methyl Phosphorothioate Thymidine        |
| modified_base | 18                                                   |
|               | mod_base = OTHER                                     |
|               | note = 2'-O-methyl Phosphorothioate Thymidine        |
| modified_base | 19                                                   |
|               | mod_base = OTHER                                     |
|               | note = 2'-O-methyl Phosphorothioate Guanosine        |
| modified_base | 20                                                   |
|               | mod_base = OTHER                                     |
|               | note = 2'-O-methyl Phosphorothioate Guanosine        |

SEQUENCE: 24
gcatcgtcag cttaccttgg                                            20

|               |                                                      |
|---------------|------------------------------------------------------|
| SEQ ID NO: 25 | moltype = DNA  length = 24                           |
| FEATURE       | Location/Qualifiers                                  |
| source        | 1..24                                                |
|               | mol_type = other DNA                                 |
|               | organism = synthetic construct                       |
| modified_base | 1                                                    |
|               | mod_base = OTHER                                     |
|               | note = 2'-O-methyl Phosphorothioate Guanosine        |
| modified_base | 2                                                    |
|               | mod_base = OTHER                                     |
|               | note = 2'-O-methyl Phosphorothioate Thymidine        |
| modified_base | 3                                                    |
|               | mod_base = OTHER                                     |
|               | note = 2'-O-methyl Phosphorothioate Cytosine         |
| modified_base | 4                                                    |
|               | mod_base = OTHER                                     |
|               | note = 2'-O-methyl Phosphorothioate (Thiol) cytosine |
| modified_base | 5                                                    |
|               | mod_base = OTHER                                     |
|               | note = 2'-O-methyl Phosphorothioate Adenosine        |
| modified_base | 6                                                    |
|               | mod_base = OTHER                                     |
|               | note = Phosphorothioate Cytosine                     |
| modified_base | 7                                                    |
|               | mod_base = OTHER                                     |
|               | note = Phosphorothioate Thymidine                    |
| modified_base | 8                                                    |
|               | mod_base = OTHER                                     |
|               | note = Phosphorothioate Adenosine                    |
| modified_base | 9                                                    |
|               | mod_base = OTHER                                     |
|               | note = Phosphorothioate Adenosine                    |
| modified_base | 10                                                   |
|               | mod_base = OTHER                                     |
|               | note = Phosphorothioate Cytosine                     |
| modified_base | 11                                                   |
|               | mod_base = OTHER                                     |
|               | note = Phosphorothioate Cytosine                     |
| modified_base | 12                                                   |
|               | mod_base = OTHER                                     |
|               | note = Phosphorothioate Thymidine                    |
| modified_base | 13                                                   |
|               | mod_base = OTHER                                     |
|               | note = Phosphorothioate Thymidine                    |
| modified_base | 14                                                   |
|               | mod_base = OTHER                                     |
|               | note = Phosphorothioate Thymidine                    |
| modified_base | 15                                                   |
|               | mod_base = OTHER                                     |
|               | note = Phosphorothioate Cytosine                     |
| modified_base | 16                                                   |
|               | mod_base = OTHER                                     |
|               | note = Phosphorothioate Adenosine                    |

```
modified_base    17
                 mod_base = OTHER
                 note = Phosphorothioate Guanosine
modified_base    18
                 mod_base = OTHER
                 note = Phosphorothioate Guanosine
modified_base    19
                 mod_base = OTHER
                 note = Phosphorothioate Cytosine
modified_base    20
                 mod_base = OTHER
                 note = 2'-O-methyl Phosphorothioate Cytosine
modified_base    21
                 mod_base = OTHER
                 note = 2'-O-methyl Phosphorothioate Adenosine
modified_base    22
                 mod_base = OTHER
                 note = 2'-O-methyl Phosphorothioate Guanosine
modified_base    23
                 mod_base = OTHER
                 note = 2'-O-methyl Cytosine
modified_base    24
                 mod_base = OTHER
                 note = 2'-O-methyl Guanosine
SEQUENCE: 25
gtccactaac ctttcaggcc agcg                                            24

SEQ ID NO: 26      moltype = RNA  length = 16
FEATURE            Location/Qualifiers
source             1..16
                   mol_type = other RNA
                   organism = synthetic construct
misc_difference    11
                   note = a, c, u or g
SEQUENCE: 26
yyyyyyyyyy ncaggr                                                     16
```